(12) United States Patent
Numata et al.

(10) Patent No.: US 9,685,615 B2
(45) Date of Patent: Jun. 20, 2017

(54) LIGHT EMITTING MATERIAL, DELAYED FLUORESCENT EMITTER, ORGANIC LIGHT EMITTING DEVICE, AND COMPOUND

(71) Applicant: KYUSHU UNIVERSITY, NATIONAL UNIVERSITY CORPORATION, Fukuoka-shi, Fukuoka (JP)

(72) Inventors: Masaki Numata, Fukuoka (JP); Takuma Yasuda, Fukuoka (JP); Jiyoung Lee, Fukuoka (JP); Asuka Yoshizaki, Fukuoka (JP); Chihaya Adachi, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 0 days.

(21) Appl. No.: 14/901,533

(22) PCT Filed: Jul. 2, 2014

(86) PCT No.: PCT/JP2014/067611
§ 371 (c)(1),
(2) Date: Dec. 28, 2015

(87) PCT Pub. No.: WO2015/002213
PCT Pub. Date: Jan. 8, 2015

(65) Prior Publication Data
US 2016/0141516 A1    May 19, 2016

(30) Foreign Application Priority Data

Jul. 3, 2013 (JP) ................................. 2013-139975

(51) Int. Cl.

| | | |
|---|---|---|
| *C07D 405/04* | (2006.01) | |
| *C07D 405/10* | (2006.01) | |
| *C07D 405/14* | (2006.01) | |
| *C07D 413/14* | (2006.01) | |
| *H01L 51/00* | (2006.01) | |
| *C09K 11/06* | (2006.01) | |
| *C07D 409/04* | (2006.01) | |
| *C07D 409/10* | (2006.01) | |
| *C07D 491/107* | (2006.01) | |
| *C07D 495/10* | (2006.01) | |
| *C07D 519/00* | (2006.01) | |
| *C09B 11/28* | (2006.01) | |
| *C09B 15/00* | (2006.01) | |
| *C09B 17/02* | (2006.01) | |
| *C09B 19/00* | (2006.01) | |
| *C09B 21/00* | (2006.01) | |

(Continued)

(52) U.S. Cl.
CPC ........ *H01L 51/0072* (2013.01); *C07D 405/04* (2013.01); *C07D 405/10* (2013.01); *C07D 405/14* (2013.01); *C07D 409/04* (2013.01); *C07D 409/10* (2013.01); *C07D 413/14* (2013.01); *C07D 491/107* (2013.01); *C07D 495/10* (2013.01); *C07D 519/00* (2013.01); *C09B 11/28* (2013.01); *C09B 15/00* (2013.01); *C09B 17/02* (2013.01); *C09B 19/00* (2013.01); *C09B 21/00* (2013.01); *C09B 57/00* (2013.01); *C09K 11/06* (2013.01); *H01L 51/005* (2013.01); *H01L 51/0071* (2013.01); *H01L 51/0073* (2013.01); *C09K 2211/1007* (2013.01); *C09K 2211/1029* (2013.01); *C09K 2211/1033* (2013.01); *C09K 2211/1088* (2013.01); *C09K 2211/145* (2013.01); *H01L 51/5012* (2013.01)

(58) Field of Classification Search
CPC .. C07D 405/04; C07D 405/10; C07D 405/14; C07D 413/14
See application file for complete search history.

(56) References Cited

U.S. PATENT DOCUMENTS

| | | |
|---|---|---|
| 8,231,983 B2 | 7/2012 | Sugita et al. |
| 9,090,819 B2 | 7/2015 | Sugita et al. |
| 2009/0066226 A1 | 3/2009 | Sugita et al. |

(Continued)

FOREIGN PATENT DOCUMENTS

| | | | |
|---|---|---|---|
| JP | 2008037930 A | * | 2/2008 |
| JP | 2011249754 A | | 12/2011 |

(Continued)

OTHER PUBLICATIONS

International Preliminary Report on Patentability dated Jan. 5, 2016, in corresponding application No. PCT/JP2014/067611.

(Continued)

*Primary Examiner* — Kahsay Habte
(74) *Attorney, Agent, or Firm* — Browdy and Neimark, PLLC

(57) ABSTRACT

A compound represented by the following general formula is useful as a light emitting material. X represents an oxygen atom or a sulfur atom. $R^1$ to $R^8$ represent a hydrogen atom or a substituent, provided that at least one of $R^1$ to $R^8$ is a carbazolyl group, etc.

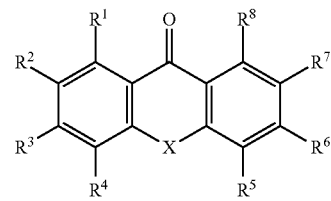

1 Claim, 23 Drawing Sheets

(51) Int. Cl.
 *C09B 57/00* (2006.01)
 *H01L 51/50* (2006.01)

(56) References Cited

U.S. PATENT DOCUMENTS

| 2012/0085997 | A1 | 4/2012 | Sugita et al. |
| 2013/0022134 | A1 | 1/2013 | Ben Artsi et al. |
| 2013/0037791 | A1 | 2/2013 | Horiuchi et al. |
| 2013/0214268 | A1 | 8/2013 | Horiuchi et al. |
| 2013/0221340 | A1 | 8/2013 | Kamatani et al. |
| 2015/0280133 | A1 | 10/2015 | Parham et al. |

FOREIGN PATENT DOCUMENTS

| JP | 201297051 A | 5/2012 |
| JP | 2012102024 A | 5/2012 |
| JP | 201316728 A | 1/2013 |
| WO | 2006114966 A1 | 11/2006 |
| WO | 2010150593 A1 | 12/2010 |
| WO | 2014067614 A | 4/2014 |

OTHER PUBLICATIONS

Wang et al, "Synthesis of "donor-bridge-acceptor" triad compounds containing the aromatic sulfur bridge" Dyes and Pigments 44 : 93-100 (2000).

Homnick et al "Modular electron donor group tuning of frontier energy levels in diarylaminofluorenone push-pull molecules" Phys. Chem. Chem. Phys., 14 : 11961-11968 (2012).

International Search Report, dated Sep. 25, 2014. In corresponding application No. PCT/JP2014/067611.

* cited by examiner

LIGHT EMITTING MATERIAL, DELAYED FLUORESCENT EMITTER, ORGANIC LIGHT EMITTING DEVICE, AND COMPOUND

TECHNICAL FIELD

The present invention relates to a compound that is useful as a light emitting material, and an organic light emitting device using the same.

BACKGROUND ART

An organic light emitting device, such as an organic electroluminescent device (organic EL device), has been actively studied for enhancing the light emission efficiency thereof. In particular, various studies for enhancing the light emitting efficiency have been made by newly developing and combining an electron transporting material, a hole transporting material, a light emitting material and the like constituting an organic electroluminescent device. There are studies relating to an organic electroluminescent device utilizing a fluorenone derivative.

Non-patent Document 1 describes the results of the studies on the solution light emission characteristics of the compound having a diarylamino group introduced to at least one of the 2- and 7-positions of fluorenone. According thereto, there is described that light emission in the visible region is observed by irradiating a hexane or acetonitrile solution of the fluorenone derivatives having the following structures with excitation light. However, Non-patent Document 1 does not describe the light emission characteristics of the compounds that have an analogous skeleton other than fluorenone.

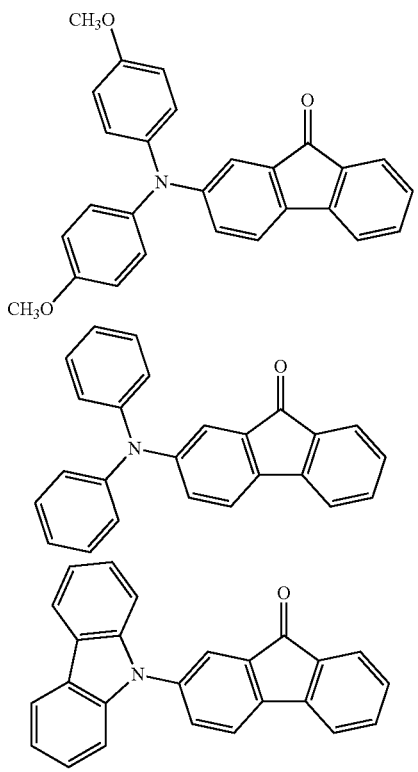

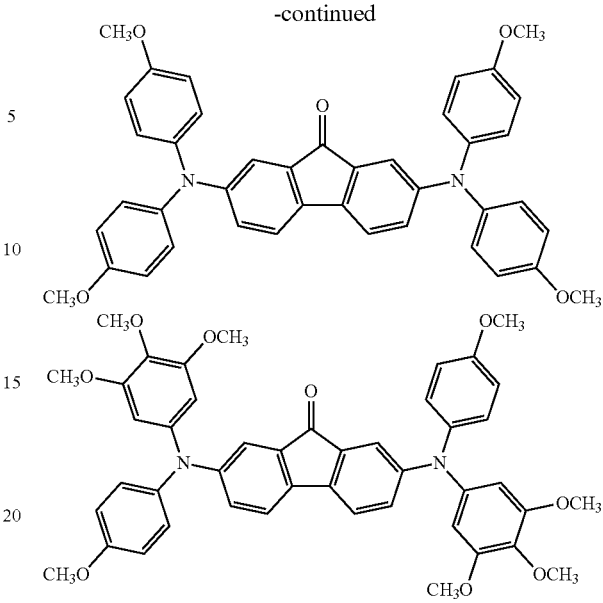

Patent Document 1 describes an example using the compound represented by the following general formula as a host material in a light emitting layer present between one pair of electrodes constituting an organic electroluminescent device, and an example using the compound in a hole barrier layer thereof. In the following general formula, $A_1$ and $A_2$ each represent a substituent. n1 and n2 each represent an integer of from 0 to 3. $X_1$ represents an oxygen atom, a sulfur atom, an alkylene group, an imino group, a carbonyl group, a sulfoxide group or a sulfonyl group. $X_2$ represents an oxygen atom, a sulfur atom, an alkylene group, an imino group, a carbonyl group, a sulfoxide group, a sulfonyl group or a simple bond.

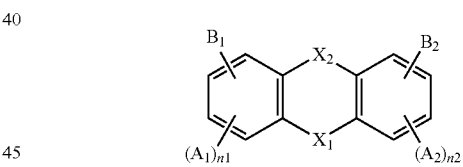

In the general formula, $B_1$ and $B_2$ each represent a compound represented by the following general formula. In the following general formula, $Z_1$ and $Z_2$ each represent an aromatic heterocyclic group, which may have a substituent, or an aromatic hydrocarbon group, and $Z_3$ represents a divalent linking group or a simple bond.

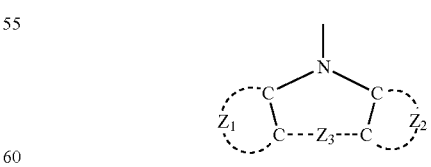

However, Patent Document 1 does not describe the light emission characteristics of the compound represented by the aforementioned general formula.

Patent Document 2 describes an example using the compound represented by the following general formula as a host material in a light emitting layer present between one pair of electrodes constituting an organic electroluminescent device, and an example using the compound in a hole barrier layer thereof. In the following general formula, $A_1$, $A_2$ and $A_3$ each represent a substituent. n1 and n2 each represent an integer of from 0 to 3. $X_1$ and $X_2$ each represent an oxygen atom, a sulfur atom, an alkylene group, an imino group, a carbonyl group, a sulfoxide group or a sulfonyl group, and $X_2$ may be a simple bond. $Z_1$, $Z_2$, $Z_3$ and $Z_4$ each represent an aromatic heterocyclic group, which may have a substituent, or an aromatic hydrocarbon group, provided that all $Z_1$, $Z_2$, $Z_3$ and $Z_4$ do not represent an aromatic hydrocarbon ring simultaneously. However, Patent Document 2 does not describe the light emission characteristics of the compound represented by the following general formula.

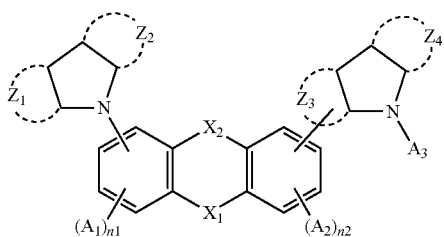

Patent Document 3 describes an example using the xanthone compound represented by the following general formula as a host material in a light emitting layer constituting an organic electroluminescent device, and an example using the compound in a hole blocking layer thereof. In the following general formula, $R_1$ to $R_8$ each represent a group that is selected independently from a hydrogen atom, an alkyl group having from 1 to 4 carbon atoms, a substituted or unsubstituted phenyl group, a substituted or unsubstituted naphthyl group, a substituted or unsubstituted phenanthryl group, a substituted or unsubstituted fluorenyl group, a substituted or unsubstituted triphenylenyl group, a substituted or unsubstituted chrysenyl group and a substituted or unsubstituted dibenzofuranyl group and a substituted or unsubstituted dibenzothienyl group. However, Patent Document 3 does not describe the light emission characteristics of the compound represented by the following general formula.

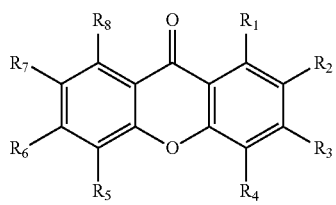

CITATION LIST

Non-Patent Document

Non-patent Document 1: Phys. Chem. Chem. Phys., 2012, 14, 11961-11968

Patent Documents

Patent Document 1: WO 2006/114966
Patent Document 2: WO 2010/150593
Patent Document 3: JP-A-2011-249754

SUMMARY OF INVENTION

Technical Problem

As described above, Non-patent Document 1 describes the capability of using the compound having a diarylamino group introduced to a fluorenone skeleton, as a light emitting material. However, the actual evaluation made by the present inventors for the light emission characteristics of the compound having a diarylamino group introduced to a fluorenone skeleton revealed that the light emission characteristics were not sufficiently satisfactory, and there was a necessity of providing a light emitting material that has further excellent light emission characteristics.

Therefore, the inventors have started various investigations on a group of compounds having a skeleton that is analogous to a fluorenone skeleton, and have firstly found the usefulness as a light emitting material of a group of compounds having a xanthone skeleton and a thioxanthone skeleton (i.e., xanthone derivatives) among many analogous skeletons, and the inventors have decided to proceed further investigations. As described above, Patent Documents 1 to 3 describe that the compound having a structure containing two benzene rings bonded through a linking group, such as a xanthone skeleton, is useful as a host material of a light emitting layer and a hole barrier material of a hole barrier layer of an organic electroluminescent device. However, there has been no investigation as to whether or not the compounds described in Patent Documents 1 to 3 have a capability of functioning as a light emitting material. The demanded properties and functions of a light emitting material are different from those of a host material and a hole transporting material, and therefore the usefulness as a light emitting material of the compounds represented by the general formulae in Patent Documents 1 to 3 is unknown.

Under the circumstances, the inventors have further performed investigations on the usefulness of a xanthone derivative as a light emitting material, and have made extensive studies for finding a compound that has excellent light emission characteristics. The inventors have also made earnest investigations for providing a general formula of a compound that is useful as a light emitting material and for generalizing the structure of an organic light emitting device having a high light emission efficiency.

Solution to Problem

As a result of earnest investigations, the inventors have found that a xanthone derivative having a particular structure has excellent properties as a light emitting material. The inventors have also found compounds that are useful as a delayed fluorescent material in the group of compounds, and have clarified that an organic light emitting device having a high light emission efficiency may be provided inexpensively. Based on the knowledge, the inventors have provided the following inventions as measures for solving the problems.

(1) A light emitting material containing a compound represented by the following general formula (1):

General Formula (1)

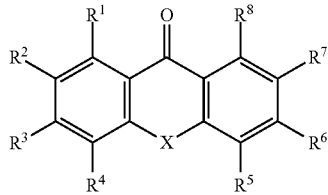

wherein in the general formula (1), X represents an oxygen atom or a sulfur atom; and $R^1$ to $R^8$ each independently represent a hydrogen atom or a substituent, provided that at least one of $R^1$ to $R^8$ each independently represent a group represented by any one of the following general formulae (2) to (6), and $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure, General Formula (2)

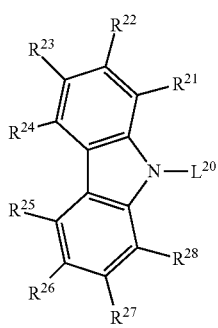

General Formula (3)

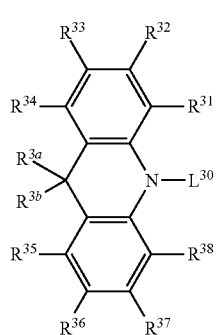

General Formula (4)

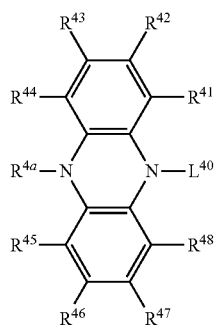

General Formula (5)

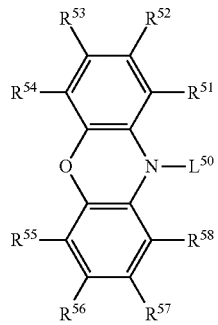

General Formula (6)

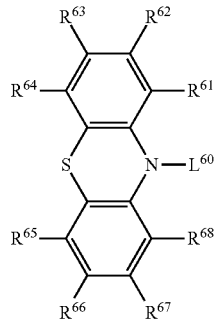

wherein in the general formulae (2) to (6), $L^{20}$, $L^{30}$, $L^{40}$, $L^{50}$ and $L^{60}$ each independently represent a single bond or a divalent linking group, and the group represented by any one of the general formulae (2) to (6) is bonded to the cyclic structure of the general formula (1) through $L^{20}$, $L^{30}$, $L^{40}$, $L^{50}$ or $L^{60}$; and $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, and $R^{61}$ to $R^{68}$ each independently represent a hydrogen atom or a substituent, provided that $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, $R^{27}$ and $R^{28}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ an and $R^{53}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, and $R^{67}$ and $R^{68}$ each may be bonded to each other to form a cyclic structure.

(2) The light emitting material according to the item (1), wherein in the general formula (1), at least one of $R^3$ and $R^6$ each represent a group represented by any one of the general formulae (2) to (6).

(3) The light emitting material according to the item (2), wherein in the general formula (1), $R^3$ and $R^6$ each represent a group represented by any one of the general formulae (2) to (6).

(4) The light emitting material according to the item (2), wherein in the general formula (1), at least one of $R^3$ and $R^6$ each represents a group represented by any one of the general formula (3).

(5) The light emitting material according to the item (2), wherein in the general formula (1), at least one of $R^3$ and $R^6$ each represents a group represented by any one of the general formula (2).

(6) The light emitting material according to any one of the items (1) to (5), wherein in the general formulae (2) to (6), at least one of $R^{21}$ to $R^{28}$, $R^{31}$ to $R^{38}$, $R^{41}$ to $R^{48}$, $R^{51}$ to $R^{58}$, and $R^{61}$ to $R^{68}$ each represents a substituent.

(7) The light emitting material according to the item (6), wherein in the general formulae (2) to (6), at least one of $R^{23}$, $R^{26}$, $R^{33}$, $R^{36}$, $R^{43}$, $R^{46}$, $R^{53}$, $R^{56}$, $R^{63}$ and $R^{66}$ each represents a substituent.

(8) The light emitting material according to the item (7), wherein the substituent is a group represented by any one of the general formulae (2) to (6).

(9) The light emitting material according to any one of the items (1) to (8), wherein in the general formulae (2) to (6), L represents a single bond.

(10) The light emitting material according to any one of the items (1) to (9), wherein in the general formula (1), X represents an oxygen atom.

(11) A delayed fluorescent emitter containing a compound represented by the following general formula (1):

General Formula (1)

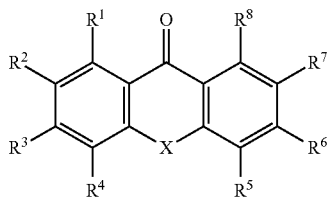

wherein in the general formula (1), X represents an oxygen atom or a sulfur atom; and $R^1$ to $R^8$ each independently represent a hydrogen atom or a substituent, provided that at least one of $R^1$ to $R^8$ each independently represent a group represented by any one of the following general formulae (2) to (6), and $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure, General Formula (2)

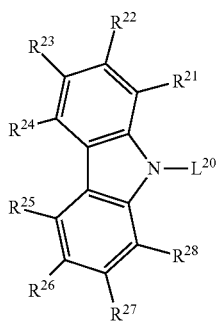

General Formula (3)

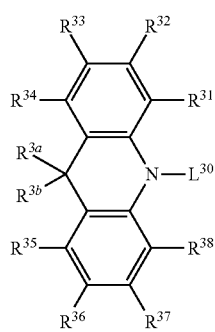

General Formula (4)

General Formula (5)

General Formula (6)

wherein in the general formulae (2) to (6), $L^{20}$, $L^{30}$, $L^{40}$, $L^{50}$ and $L^{60}$ each independently represent a single bond or a divalent linking group, and the group represented by any one of the general formulae (2) to (6) is bonded to the cyclic structure of the general formula (1) through $L^{20}$, $L^{30}$, $L^{40}$, $L^{50}$ or $L^{60}$; and $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, and $R^{61}$ to $R^{69}$ each independently represent a hydrogen atom or a substituent, provided that $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, $R^{27}$ and $R^{28}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, and $R^{67}$ and $R^{68}$ each may be bonded to each other to form a cyclic structure.

(12) An organic light emitting device containing a light emitting material according to any one of the items (1) to (10).

(13) The organic light emitting device according to the item (12), wherein the organic light emitting device emits delayed fluorescent light.

(14) The organic light emitting device according to the item (12) or (13), wherein the organic light emitting device is an organic electroluminescent device.

(15) A compound represented by the following general formula (1'):

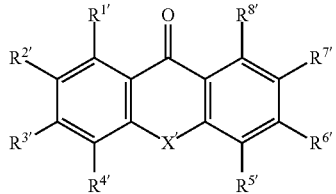

General Formula (1')

wherein in the general formula (1'), X' represents an oxygen atom or a sulfur atom; and $R^{1'}$ to $R^{8'}$ each independently represent a hydrogen atom or a substituent, provided that at least one of $R^{1'}$ to $R^{8'}$ each independently represent a group represented by any one of the following general formulae (2') to (6'), and $R^{1'}$ and $R^{2'}$, $R^{2'}$ and $R^{3'}$, $R^{3'}$ and $R^{4'}$, $R^{5'}$ and $R^{6'}$, $R^{6'}$ and $R^{7'}$, and $R^{7'}$ and $R^{8'}$ each may be bonded to each other to form a cyclic structure, and such a case is excluded that $R^{2'}$ and $R^{7'}$ each represent a group represented by the following general formula (2'), and all $R^{21'}$ to $R^{28'}$ represent hydrogen atoms,

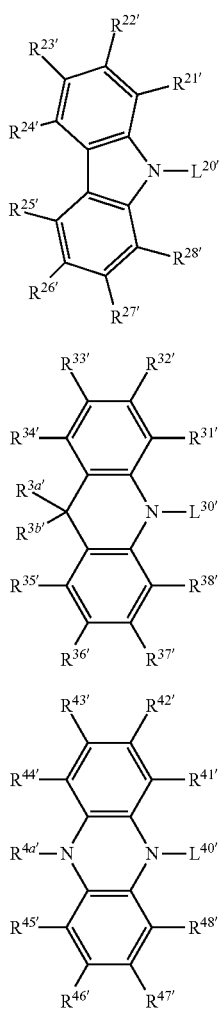

General Formula (2')

General Formula (3')

General Formula (4')

General Formula (5')

General Formula (6')

wherein in the general formulae (2') to (6'), $L^{20'}$, $L^{30'}$, $L^{40'}$, $L^{50'}$ and $L^{60'}$ each independently represent a single bond or a divalent linking group, and the group represented by any one of the general formulae (2') to (6') is bonded to the cyclic structure of the general formula (1) through $L^{20'}$, $L^{30'}$, $L^{40'}$, $L^{50'}$ or $L^{60'}$; and $R^{21'}$ to $R^{28'}$, $R^{31'}$ to $R^{38'}$, $R^{3a'}$, $R^{3b'}$, $R^{41'}$ to $R^{48'}$, $R^{4a'}$, $R^{51'}$ to $R^{58'}$, and $R^{61'}$ to $R^{68'}$ each independently represent a hydrogen atom or a substituent, provided that $R^{21'}$ and $R^{22'}$, $R^{22'}$ and $R^{23'}$, $R^{23'}$ and $R^{24'}$, $R^{24'}$ and $R^{25'}$, $R^{25'}$ and $R^{26'}$, $R^{26'}$ and $R^{27'}$, $R^{27'}$ and $R^{28'}$, $R^{31'}$ and $R^{32'}$, $R^{32'}$ and $R^{33'}$, $R^{33'}$ and $R^{34'}$, $R^{35'}$ and $R^{36'}$, $R^{36'}$ and $R^{37'}$, $R^{37'}$ and $R^{38'}$, $R^{3a'}$ and $R^{3b'}$, $R^{41'}$ and $R^{42'}$, $R^{42'}$ and $R^{43'}$, $R^{43'}$ and $R^{44'}$, $R^{45'}$ and $R^{46'}$, $R^{46'}$ and $R^{47'}$, $R^{47'}$ and $R^{48'}$, $R^{51'}$ and $R^{52'}$, $R^{52'}$ and $R^{53'}$, $R^{53'}$ and $R^{54'}$, $R^{55'}$ and $R^{56'}$, $R^{56'}$ and $R^{57'}$, $R^{57'}$ and $R^{58'}$, $R^{61'}$ and $R^{62'}$, $R^{62'}$ and $R^{63'}$, $R^{63'}$ and $R^{64'}$, $R^{65'}$ and $R^{66'}$, $R^{66'}$ and $R^{67'}$, and $R^{67'}$ and $R^{68'}$ each may be bonded to each other to form a cyclic structure.

DESCRIPTION OF EMBODIMENTS

Figure 1:
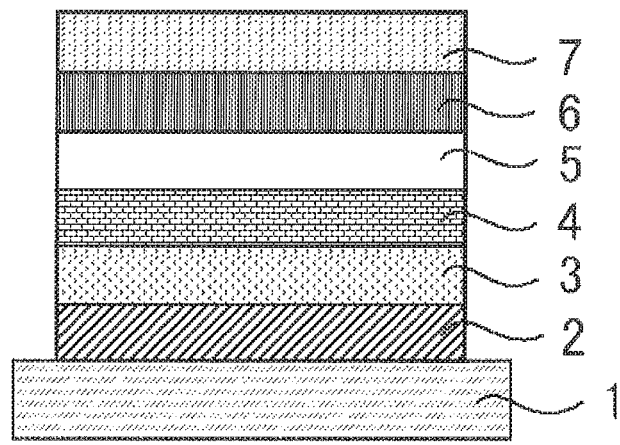
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in the compound used in the invention is not particularly limited in isotope species, and for example, all the hydrogen atoms in the molecule may be $^1$H, and all or a part of them may be $^2$H (deuterium (D))

Compound Represented by General Formula (1)

The light emitting material of the invention contains a compound represented by the following general formula (1)

General Formula (1)

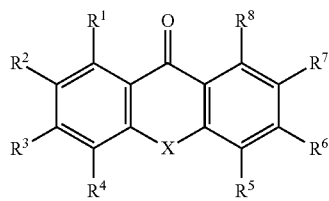

In the general formula (1), X represents an oxygen atom or a sulfur atom; and $R^1$ to $R^8$ each independently represent a hydrogen atom or a substituent, provided that at least one of $R^1$ to $R^8$ each independently represent a group represented by any one of the following general formulae (2) to (6). X may represent any of an oxygen atom and a sulfur atom, and preferably represents an oxygen atom.

The number of the groups represented by any one of the following general formulae (2) to (6) may be only 1 or may be 2 or more, and is preferably from 1 to 4, and more preferably 1 or 2. In the case where the general formula (1) contains plural groups each represented by any one of the general formulae (2) to (6), the groups may be the same as or different from each other.

In the case where the number of the group represented by any one of the following general formulae (2) to (6) is only 1, it is preferred that $R^2$ or $R^3$ represents the group represented by any one of the following general formulae (2) to (6), and it is more preferred that $R^3$ represents the group represented by any one of the following general formulae (2) to (6).

In the case where the number of the groups represented by any one of the following general formulae (2) to (6) is 2 or more, it is preferred that at least one of $R^1$ to $R^4$ and at least one of $R^5$ to $R^8$ each represent the group represented by any one of the following general formulae (2) to (6). In this case, it is preferred that the number of the groups represented by any one of the following general formulae (2) to (6) is from 1 to 3 among $R^1$ to $R^4$, and is from 1 to 3 among $R^5$ to $R^8$, and it is more preferred that the number of the groups is 1 or 2 among $R^1$ to $R^4$, and is 1 or 2 among $R^5$ to $R^8$. The number of the groups represented by any one of the general formulae (2) to (6) among $R^1$ to $R^4$ and the number of the groups represented by any one of the general formulae (2) to (6) among $R^5$ to $R^8$ may be the same as or different from each other, and is preferably the same as each other. Among $R^1$ to $R^4$, it is preferred that at least one of $R^2$ to $R^4$ each represent the group represented by any one of the general formulae (2) to (6), and it is more preferred that at least $R^3$ represents the group represented by any one of the general formulae (2) to (6). Among $R^5$ to $R^8$, it is preferred that at least one of $R^5$ to $R^7$ each represent the group represented by any one of the general formulae (2) to (6), and it is more preferred that at least $R^6$ represents the group represented by any one of the general formulae (2) to (6). The preferred compounds include the compound, in which $R^3$ and $R^6$ in the general formula (1) each represent the group represented by any one of the general formulae (2) to (6), the compound, in which $R^2$ and $R^7$ in the general formula (1) each represent the group represented by any one of the general formulae (2) to (6), and the compound, in which $R^2$, $R^3$, $R^6$ and $R^7$ in the general formula (1) each represent the group represented by any one of the general formulae (2) to (6), and the more preferred compounds include the compound, in which $R^3$ and $R^6$ each represent the group represented by any one of the general formulae (2) to (6). The plural groups each represented by any one of the general formulae (2) to (6) contained in the general formula (1) may be the same as or different from each other, and are preferably the same as each other. The compound represented by the general formula (1) preferably has a symmetric structure, i.e., $R^1$ and $R^8$, $R^2$ and $R^7$, $R^3$ and $R^6$, and $R^4$ and $R^5$ each are preferably the same as each other.

In the compound represented by the general formula (1), both $R^3$ and $R^6$ each represent the group represented by any one of the following general formulae (2) to (6). The preferred compounds include the compound represented by the general formula (1), in which at least one of $R^3$ and $R^6$ each represent the following general formula (2) or (3).

General Formula (2)

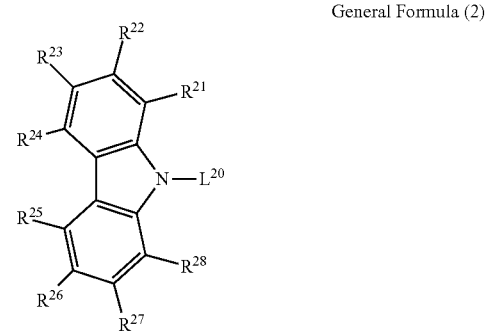

General Formula (3)

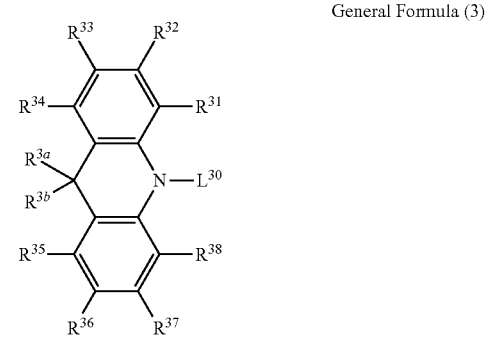

General Formula (4)

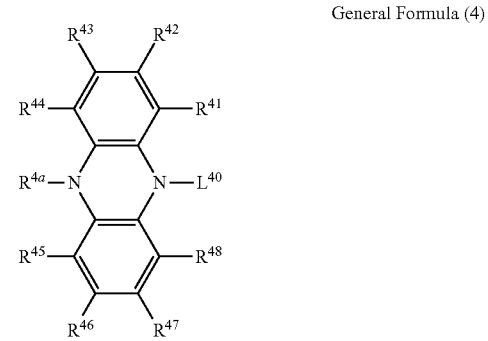

-continued

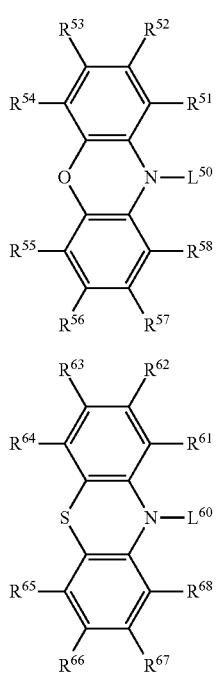

General Formula (5)

General Formula (6)

In the general formulae (2) to (6), $L^{20}$, $L^{30}$, $L^{40}$, $L^{50}$ and $L^{60}$ each independently represent a single bond or a divalent linking group; and $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, and $R^{61}$ to $R^{68}$ each independently represent a hydrogen atom or a substituent.

$L^{20}$, $L^{30}$, $L^{40}$, $L^{50}$ and $L^{60}$ each may represent a single bond or a divalent linking group, and preferably represents a single bond. In the case where at least one of $R^1$ to $R^8$ in the general formula (1) each represent the group represented by any one of the general formulae (2) to (6) having $L^{20}$, $L^{30}$, $L^{40}$, $L^{50}$ and $L^{60}$ as a linking group, the number of the linking group present in the general formula (1) may be only 1 or may be 2 or more. In the case where the general formula (1) contains plural linking groups, the linking groups may be the same as or different from each other. Examples of the divalent linking group that may be represented by $L^{20}$, $L^{30}$, $L^{40}$, $L^{50}$ and $L^{60}$ include an alkenylene group, an alkynylene group, an arylene group, a thiophenediyl group, and a linking group formed of a combination of these groups. The alkylene group and the alkenylene group each preferably have from 2 to 10 carbon atoms, more preferably from 2 to 6 carbon atoms, and further preferably from 2 to 4 carbon atoms. The arylene group preferably has from 6 to 10 carbon atoms, and more preferably 6 carbon atoms, and a p-phenylene group is further preferred. Examples of the thiophenediyl group include a 3,4-thiophenediyl group and 2,5-thiophenediyl group. Preferred examples of the linking group include a linking group represented by the general formula —(CR$^a$=CR$^b$)$_n$—. In the general formula, R$^a$ and R$^b$ each independently represent a hydrogen atom or an alkyl group. The alkyl group preferably has from 1 to 6 carbon atoms, and more preferably from 1 to 3 carbon atoms. n is preferably from 1 to 5, more preferably from 1 to 3, and further preferably 1 or 2. Examples thereof include —CH=CH— and —(CH=CH)$_2$—.

The number of a substituent in the general formulae (2) to (6) is not particularly limited. In each of the general formulae (2) to (6), all $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, and $R^{61}$ to $R^{68}$ each may be unsubstituted (i.e., a hydrogen atom), it is preferred that at least one of $R^{21}$ to $R^{28}$, $R^{31}$ to $R^{38}$, $R^{41}$ to $R^{48}$, $R^{51}$ to $R^{58}$, and $R^{61}$ to $R^{68}$ each represent a substituent, and it is more preferred that at least one of $R^{23}$, $R^{26}$, $R^{33}$, $R^{36}$, $R^{43}$, $R^{46}$, $R^{53}$, $R^{56}$, $R^{63}$ and $R^{66}$ each represents a substituent. In the case where the general formulae (2) to (6) contain plural substituents, the substituents may be the same as or different from each other.

Examples of the substituent that may be represented by $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, and $R^{61}$ to $R^{68}$ and the substituent that may be represented by $R^1$ to $R^8$ include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, an alkoxy group having from 1 to 20 carbon atoms, a substituted or unsubstituted aryl group having from 6 to 40 carbon atoms, a substituted or unsubstituted heteroaryl group having from 3 to 40 carbon atoms, and a dialkyl-substituted amino group having from 1 to 20 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms and a substituted or unsubstituted heteroaryl group having from 3 to 12 carbon atoms.

At least one of $R^{23}$, $R^{26}$, $R^{33}$, $R^{36}$, $R^{43}$, $R^{46}$, $R^{53}$, $R^{56}$, $R^{63}$ and $R^{66}$ each preferably independently represent the group represented by any one of the general formulae (2) to (6).

$R^1$ and $R^2$, $R^2$ and $R^3$, $R^3$ and $R^4$, $R^5$ and $R^6$, $R^6$ and $R^7$, and $R^7$ and $R^8$, $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, $R^{27}$ and $R^{28}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, and $R^{67}$ and $R^{68}$ each may be bonded to each other to form a cyclic structure. The cyclic structure may be an aromatic ring or an aliphatic ring, and may contain a hetero atom, and the cyclic structure may be a condensed ring containing two or more rings. The hetero atom referred herein is preferably selected from the group consisting of a nitrogen atom, an oxygen atom and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring and a cycloheptene ring.

Specific examples of the compound represented by the general formula (1) shown below. However, the compound represented by the general formula (1) capable of being used in the invention is not construed as being limited to the specific examples.

Compound 1

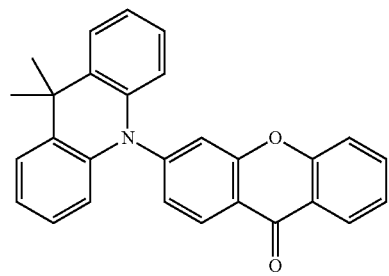

Compound 2

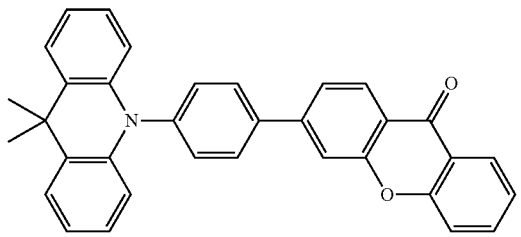

Compound 3

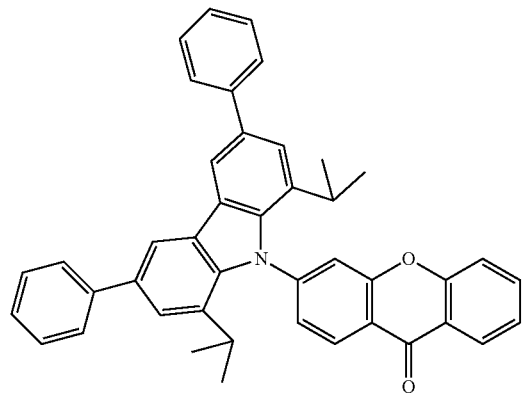

Compound 4

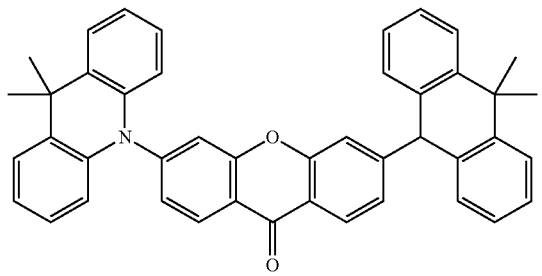

Compound 5

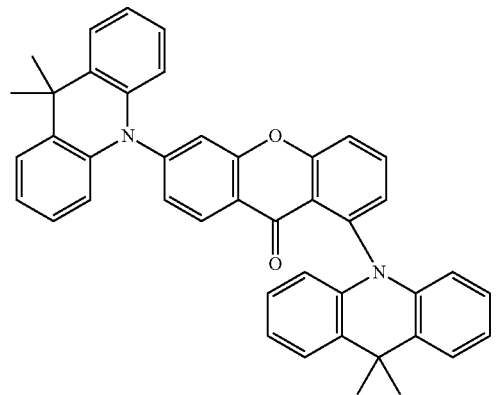

Compound 6

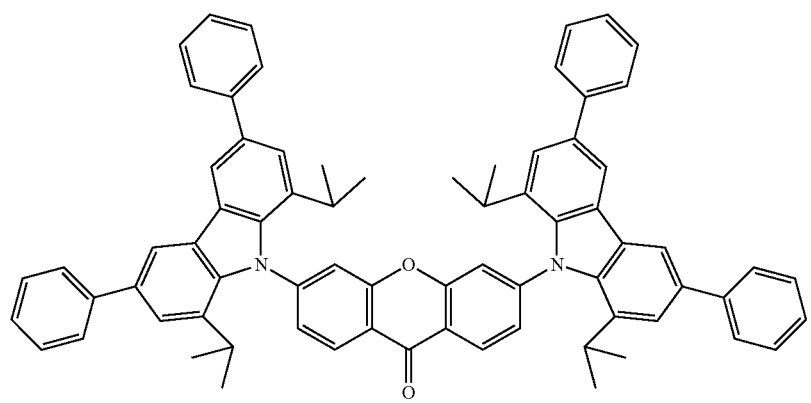

-continued
Compound 7
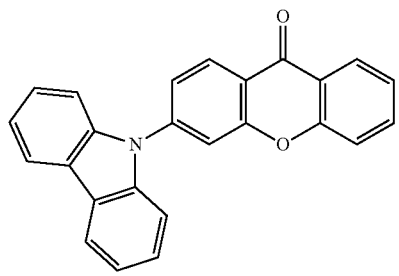
Compound 8
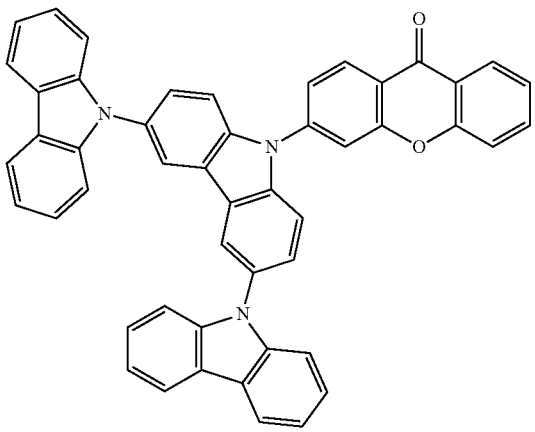
Compound 9
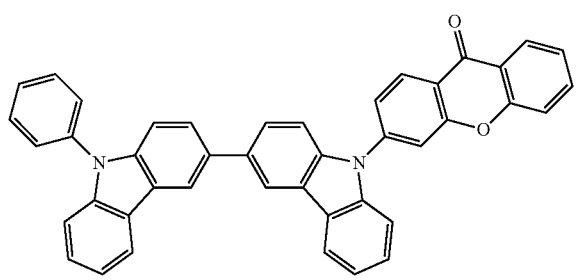
Compound 10
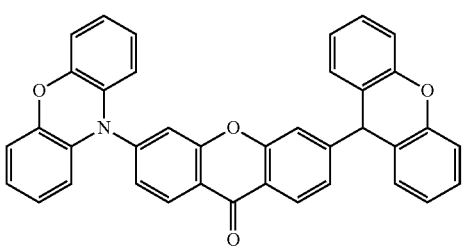
Compound 11
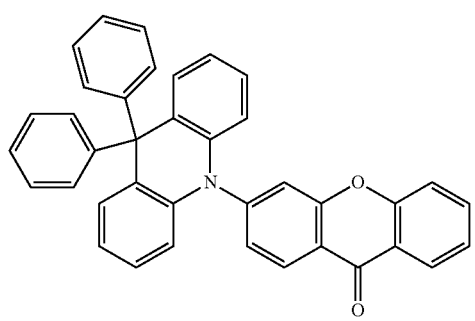
Compound 12
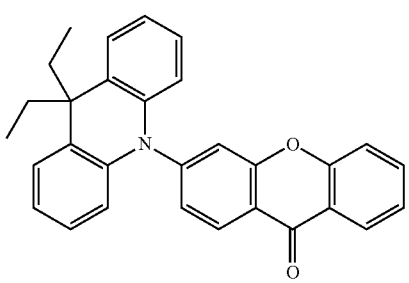
Compound 13
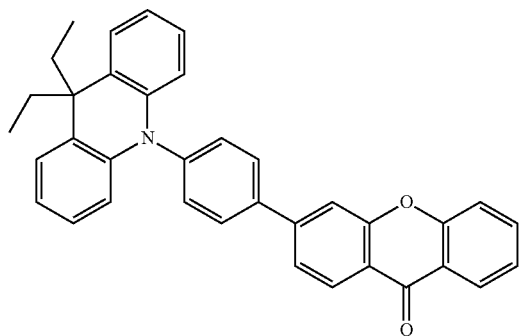
Compound 14
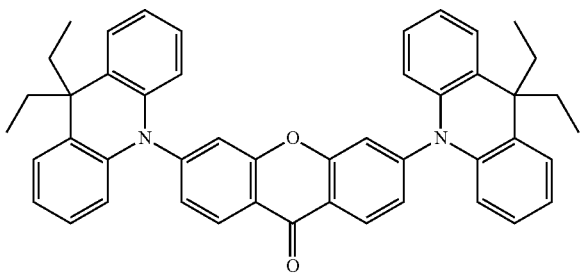

-continued
Compound 15
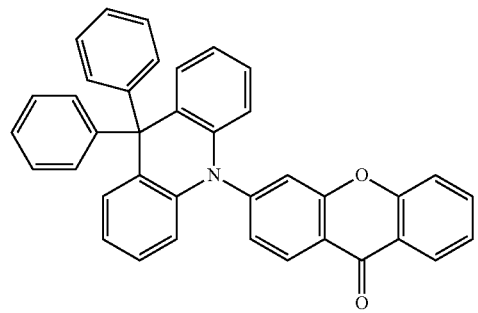
Compound 16
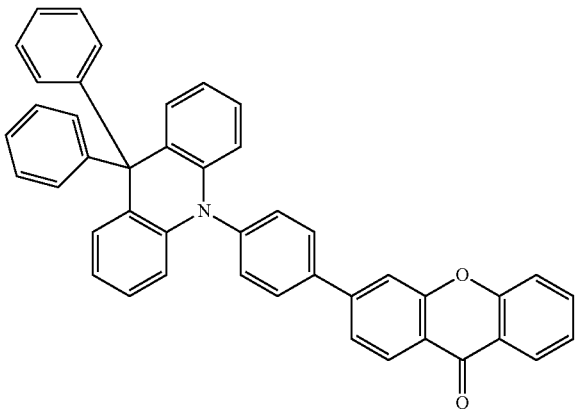
Compound 17
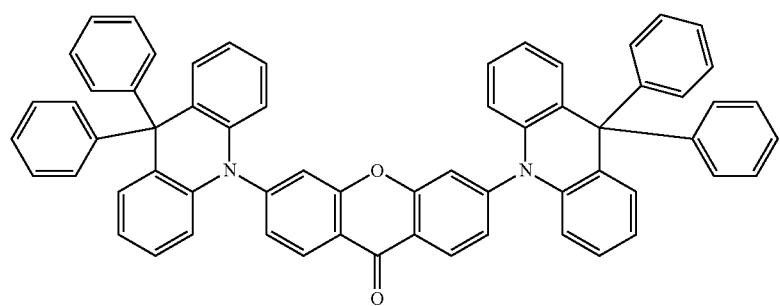
Compound 18
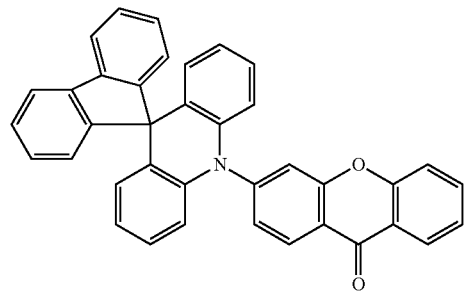
Compound 19
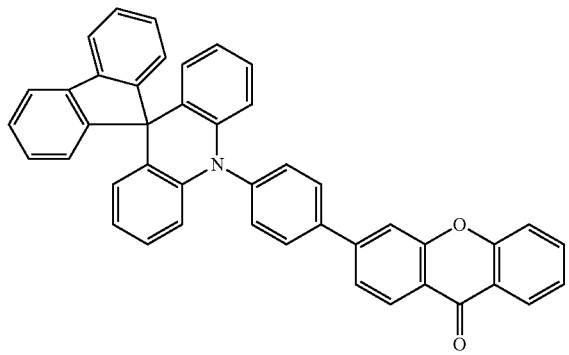
Compound 20
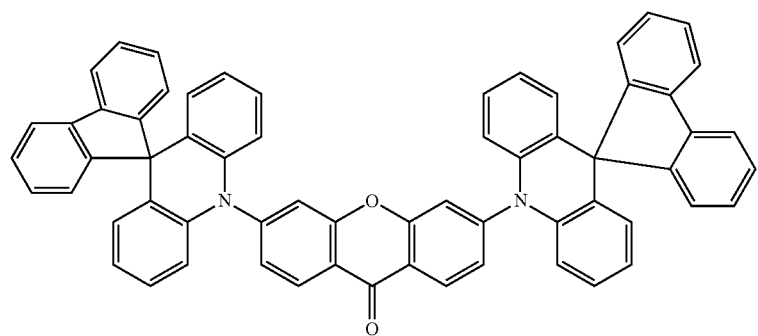

-continued
Compound 21
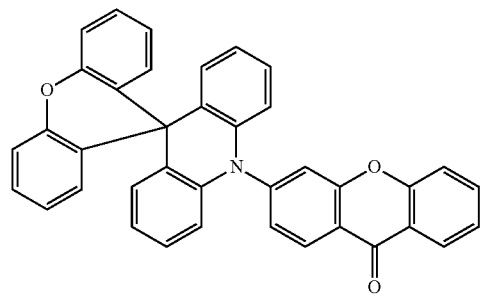
Compound 22
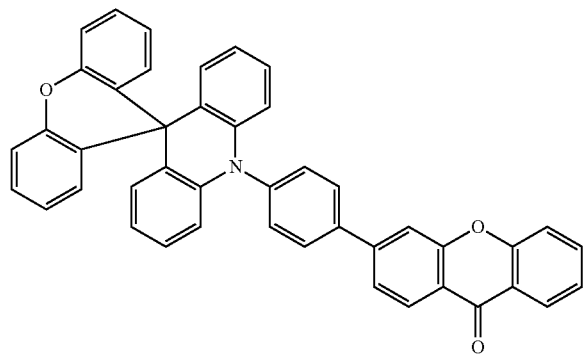
Compound 23
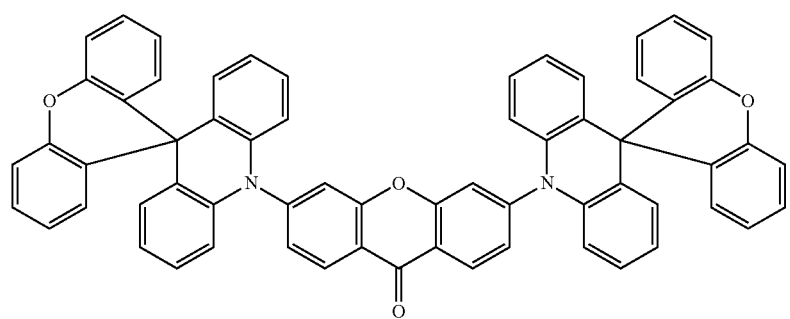
Compound 24
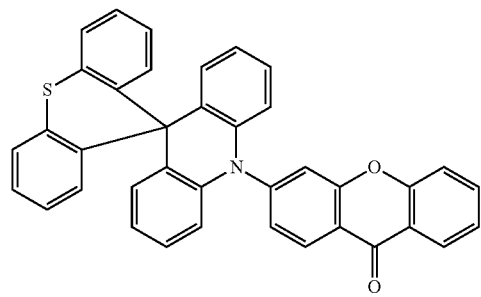
Compound 25
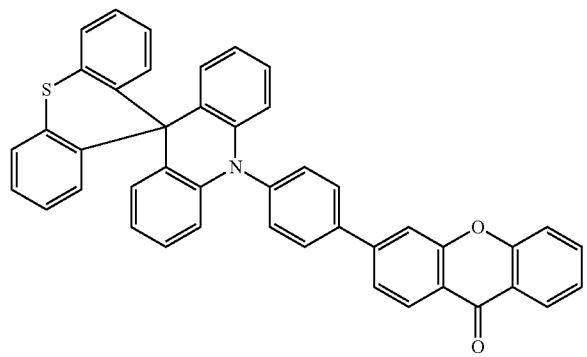
Compound 26
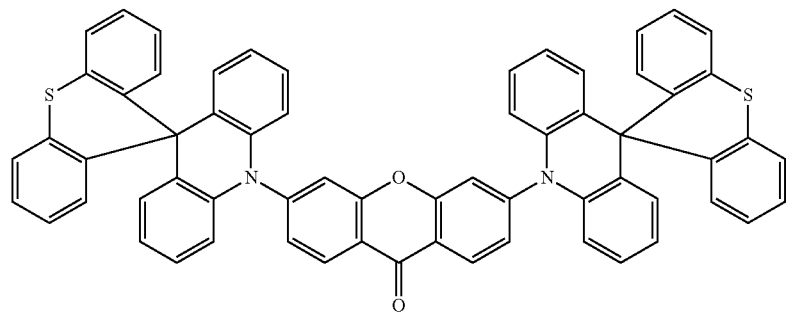

-continued
Compound 27
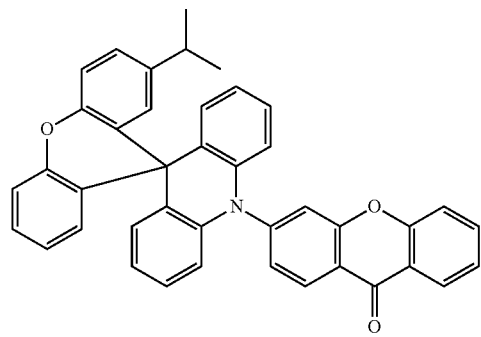
Compound 28
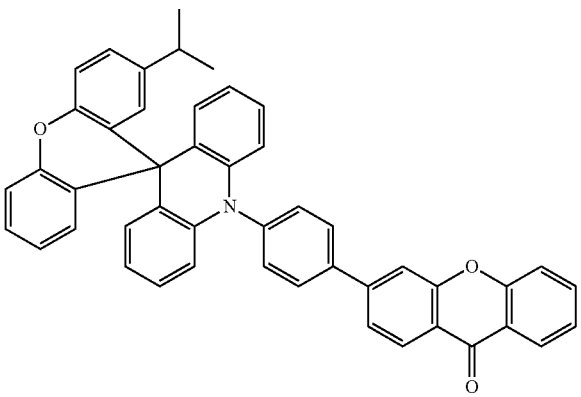
Compound 29
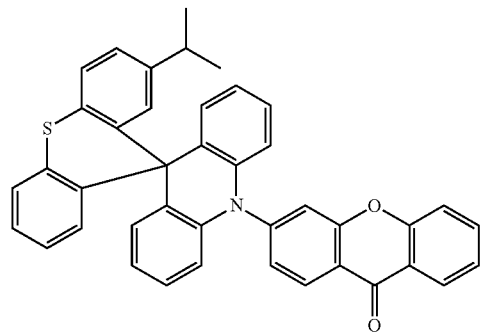
Compound 30
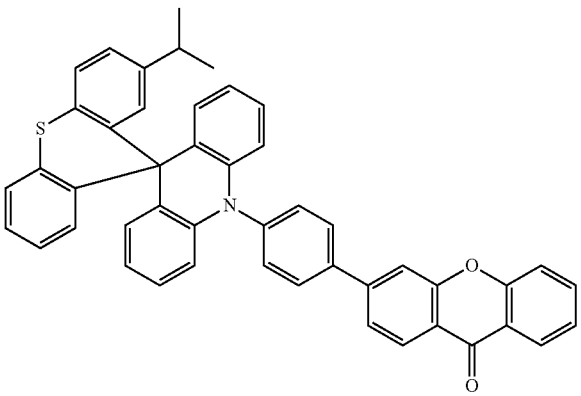
Compound 31
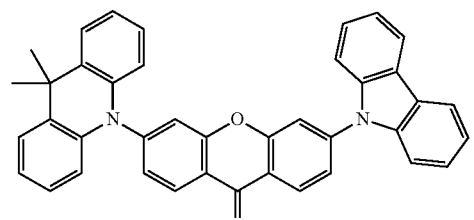
Compound 32
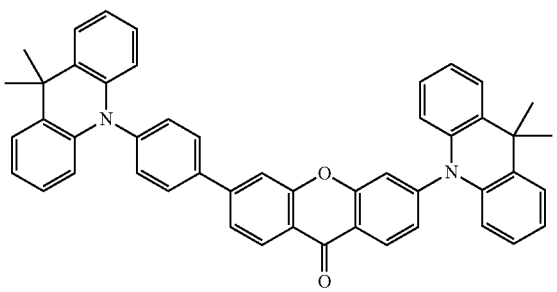
Compound 33
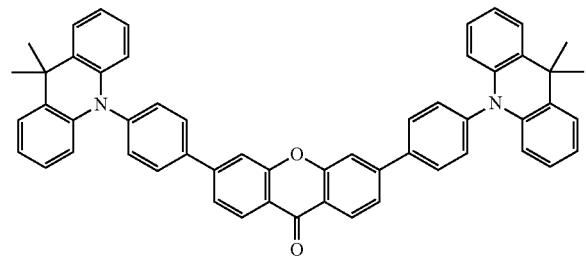
Compound 34
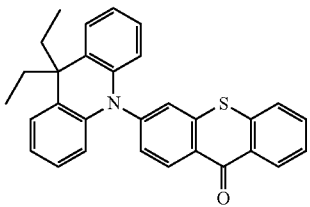

-continued
Compound 35
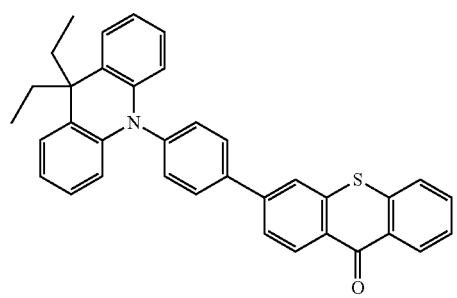
Compound 36
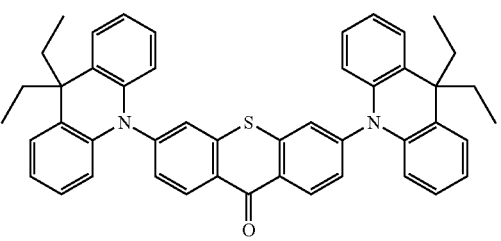
Compound 37
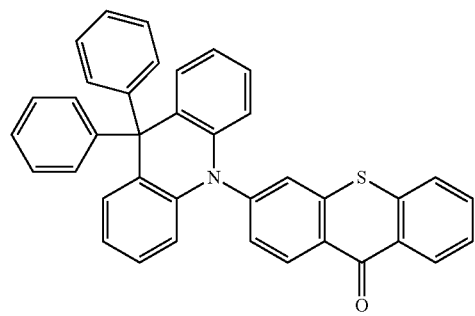
Compound 38
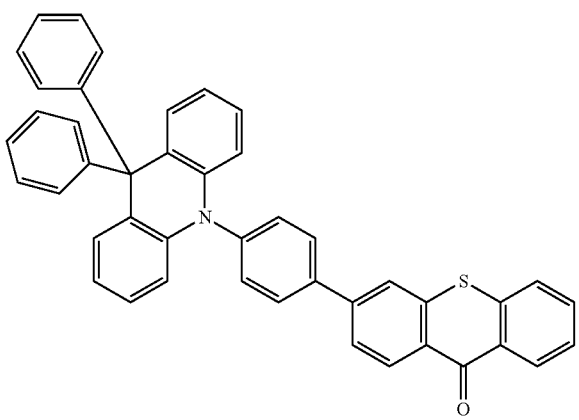
Compound 39
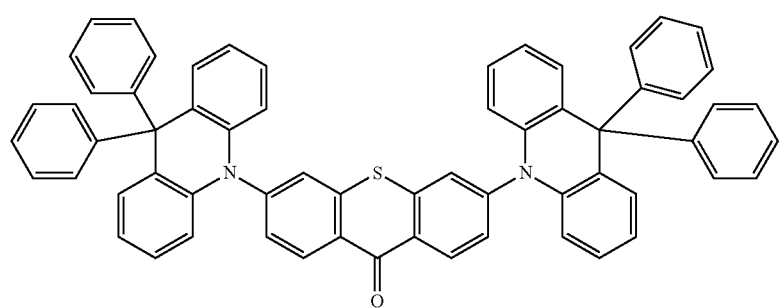
Compound 40
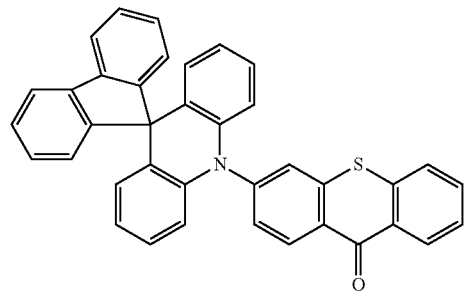
Compound 41
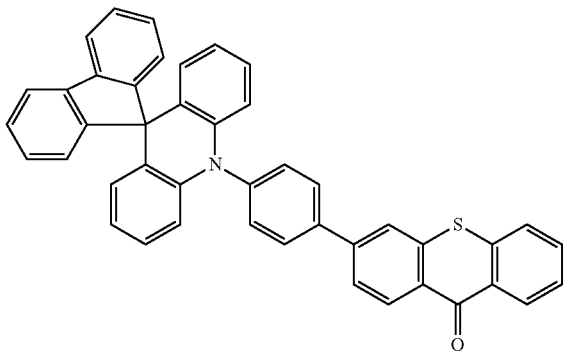

-continued
Compound 42
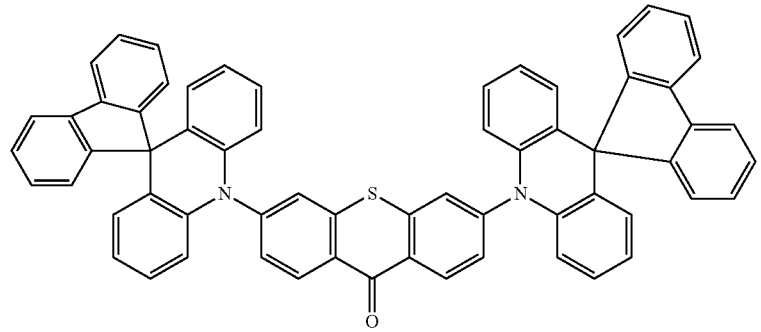
Compound 43
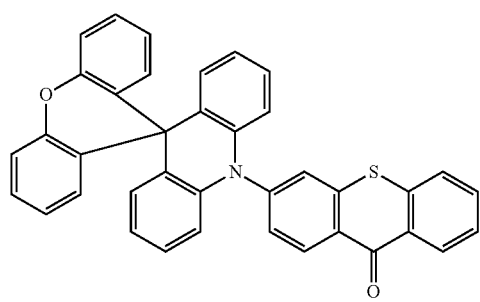
Compound 44
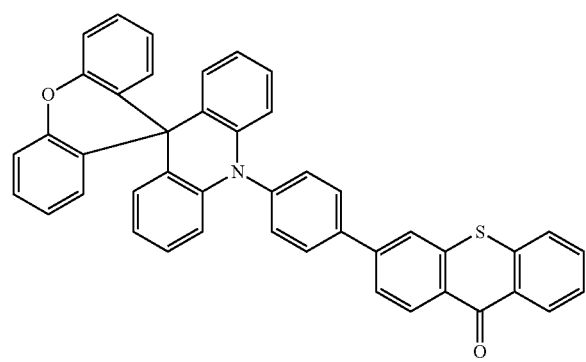
Compound 45
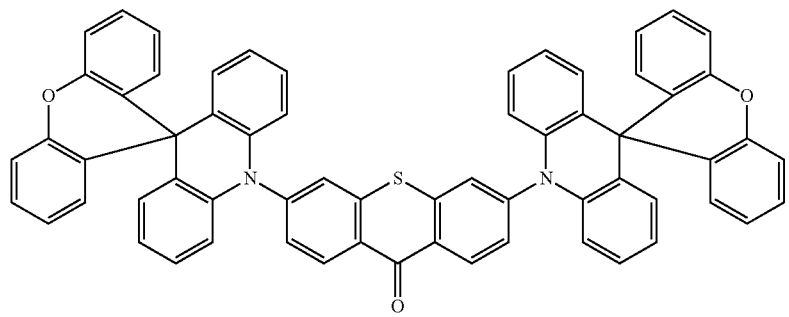
Compound 46
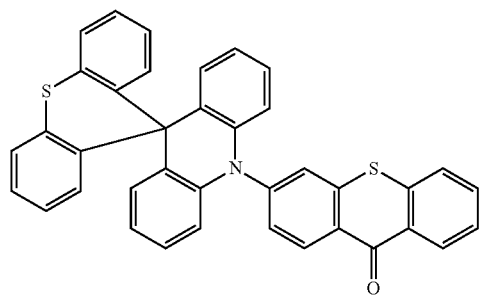
Compound 47
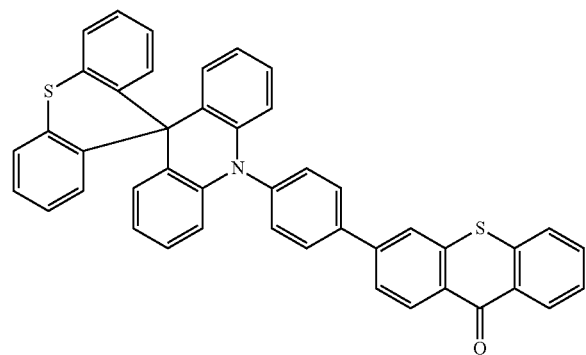

-continued
Compound 48
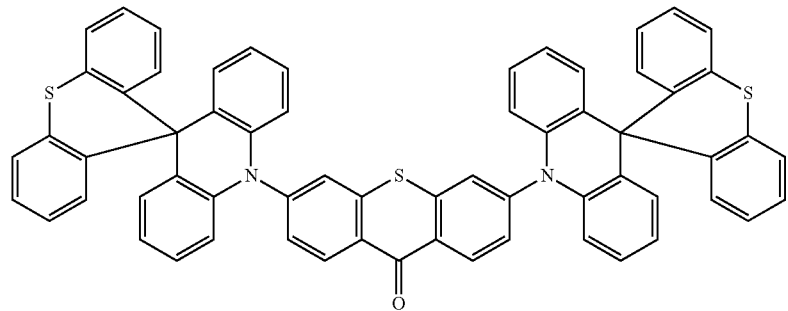
Compound 49
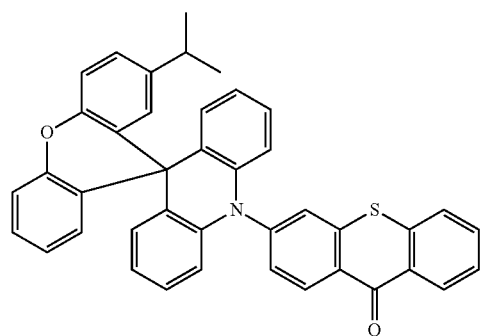
Compound 50
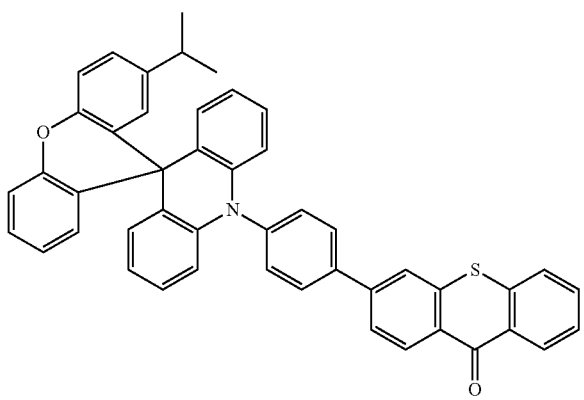
Compound 51
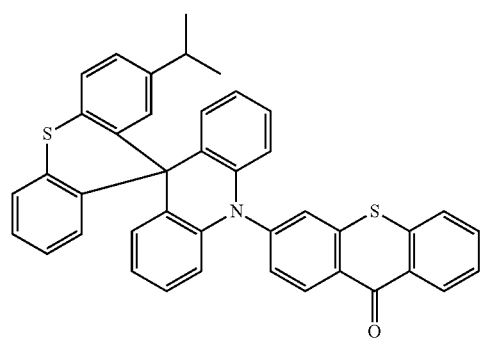
Compound 52
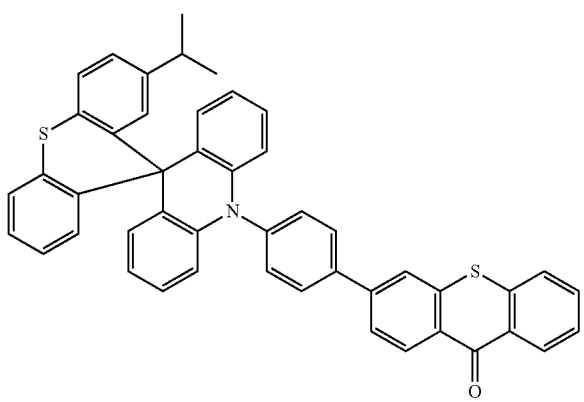
Compound 53
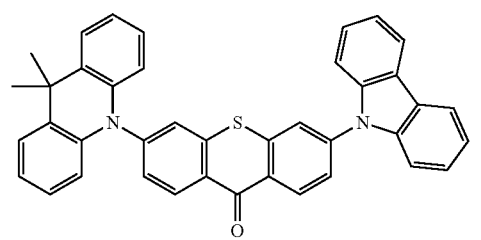
Compound 54
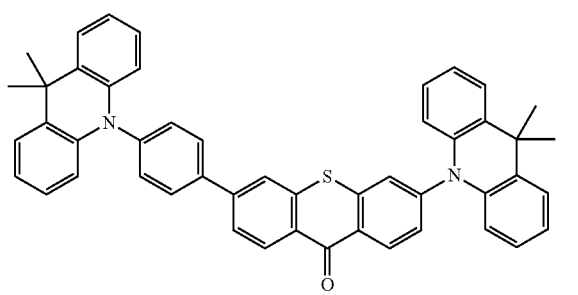

-continued

Compound 55

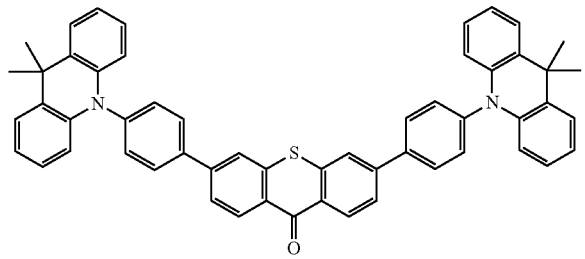

Compound 56

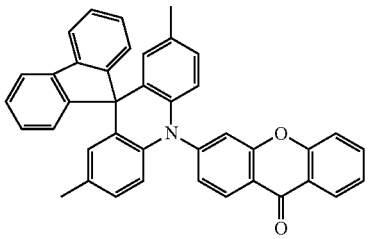

Compound 57

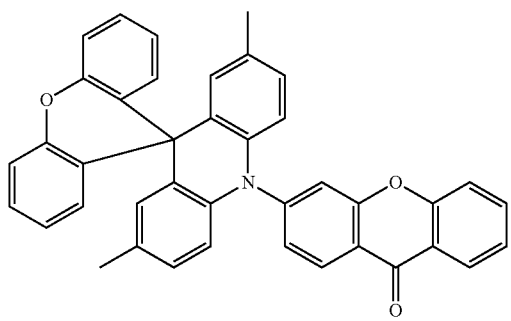

Compound 58

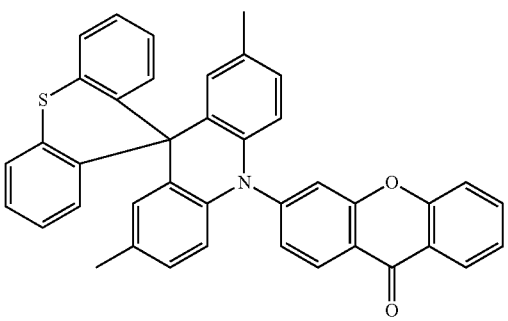

Compound 59

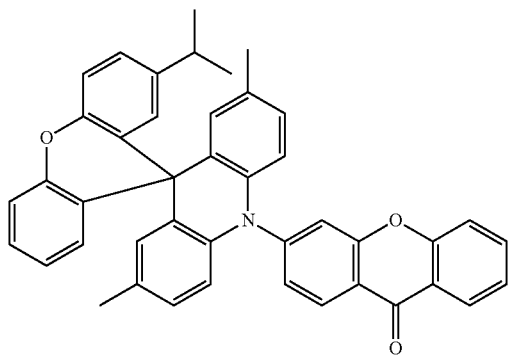

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method. The lower limit of the molecular weight is the molecular weight, of the smallest compound represented by the general formula (1)

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used as a light emitting material.

For example, it may be considered that a polymerizable group is introduced in advance to the structure represented by the general formula (1), and a polymer obtained by polymerizing the polymerizable group is used as a light emitting material. Specifically, it may be considered that a monomer that has a polymerizable functional group at any of $R^1$ to $R^8$ in the general formula (1) is prepared, and is homopolymerized or copolymerized with another monomer to prepare a polymer containing repeating units, and the polymer is used as a light emitting material. In alternative, it may be considered that the compounds represented by the general formula (1) are coupled to form a dimer or a trimer and the dimer or the trimer is used as a light emitting material.

Examples of the polymer having the repeating unit containing the structure represented by the general formula (1) include a polymer containing a structure represented by the following general formula (9) or (10)

General Formula (9)

General Formula (10)

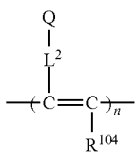

In the general formulae (9) and (10), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by $-X^{11}-L^{11}-$, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (9) and (10), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $R^1$ to $R^8$ in the structure represented by the general formula (1), any of $R^{21}$ to $R^{28}$ in the structure represented by the general formula (2), any of $R^{31}$ to $R^{38}$, $R^{3a}$ and $R^{3b}$ in the structure represented by the general formula (3), any of $R^{41}$ to $R^{48}$ and $R^{4a}$ in the structure represented by the general formula (4), any of $R^{51}$ to $R^{58}$ in the structure represented by the general formula (5), and any of $R^{61}$ to $R^{68}$ in the structure represented by the general formula (6), which structures constitute Q. Two or more of the linking groups may be boded to one group represented by Q to form a crosslinked structure or a network structure.

Specific examples of the structure of the repeating unit include structures represented by the following formulae (11) to (14).

Formula (11)

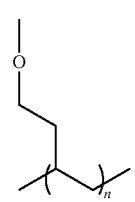

Formula (12)

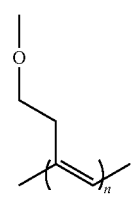

Formula (13)

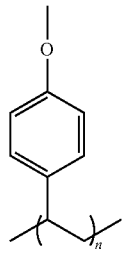

Formula (14)

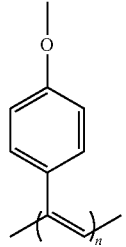

The polymer having the repeating unit containing the structure represented by any of the formulae (11) to (14) may be synthesized in such a manner that a hydroxyl group is introduced to any of $R^1$ to $R^8$ in the structure represented by the general formula (1), and the hydroxyl group as a linker is reacted with the following compound to introduce a polymerizable group thereto, followed by polymerizing the polymerizable group.

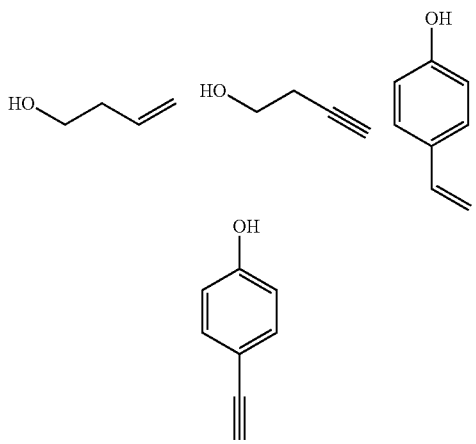

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene.

Compound Represented by General Formula (1')

In the compound represented by the general formula (1), a compound that is represented by the following general formula (1') is a novel compound.

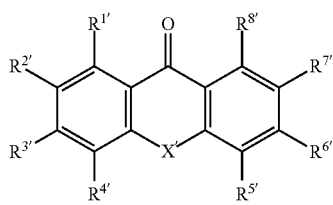

General Formula (1')

In the general formula (1'), X' represents an oxygen atom or a sulfur atom; and $R^{1'}$ to $R^{8'}$ each independently represent a hydrogen atom or a substituent, provided that at least one of $R^{1'}$ to $R^{8'}$ each independently represent a group represented by any one of the following general formulae (2') to (6'), and such a case is excluded that $R^2$ and $R'$ each represent a group represented by the following general formula (2'), and all $R^{21'}$ to $R^{28'}$ represent hydrogen atoms,

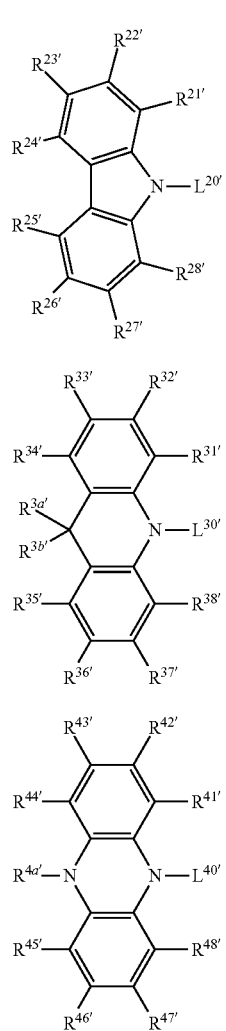

General Formula (2')

General Formula (3')

General Formula (4')

General Formula (5')

General Formula (6')

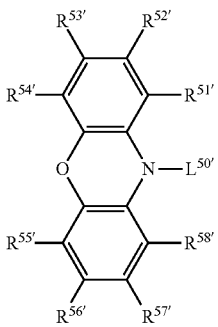

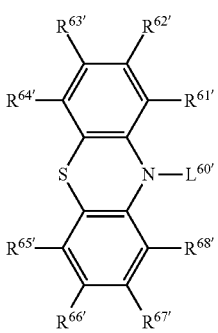

In the general formulae (2) to (6) $L^{20'}$, $L^{30'}$, $L^{40'}$, $L^{50'}$ and $L^{60'}$ and each independently represent a single bond or a divalent linking group; and $R^{21'}$ $R^{28'}$, $R^{31'}$ $R^{38'}$, $R^{3a'}$, $R^{3b'}$, $R^{41'}$ to $R^{48'}$, $R^{4a'}$, $R^{51'}$ to $R^{58'}$, and $R^{61'}$ to $R^{68'}$ each independently represent a hydrogen atom or a substituent. $R^{1'}$ and $R^{2'}$, $R^{2'}$ and $R^{3'}$, $R^{3'}$ and $R^{4'}$, $R^{5'}$ and $R^{6'}$, $R^{6'}$ and $R^{7'}$, $R^{7'}$ and $R^{8'}$, $R^{21'}$ and $R^{22'}$, $R^{22'}$ and $R^{23'}$, $R^{23'}$ and $R^{24'}$, $R^{24'}$ and $R^{25'}$, $R^{25'}$ and $R^{26'}$, $R^{26'}$ and $R^{27'}$, $R^{27'}$ and $R^{28'}$, $R^{31'}$ and $R^{32'}$, $R^{32'}$ and $R^{33'}$, $R^{33'}$ and $R^{34'}$, $R^{35'}$ and $R^{36'}$, $R^{36'}$ and $R^{37'}$, $R^{37'}$ and $R^{38'}$, $R^{3a'}$ and $R^{3b'}$, $R^{41'}$ and $R^{42'}$, $R^{42'}$ and $R^{43'}$, $R^{43'}$ and $R^{44'}$, $R^{45'}$ and $R^{46'}$, $R^{46'}$ and $R^{47'}$, $R^{47'}$ and $R^{48'}$, $R^{51'}$ and $R^{52'}$, $R^{52'}$ and $R^{53'}$, $R^{53'}$ and $R^{54'}$, $R^{55'}$ and $R^{56'}$ and $R^{57'}$, $R^{57'}$ and $R^{58'}$, $R^{61'}$ and $R^{62'}$, $R^{62'}$ and $R^{63'}$, $R^{63'}$ and $R^{64'}$, $R^{65'}$ and $R^{66'}$, $R^{66'}$ and $R^{67'}$, and $R^{67'}$ and $R^{68'}$ each may be bonded to each other to form a cyclic structure.

For the descriptions and the preferred ranges of $R^{1'}$ to $R^{8'}$, $R^{21'}$ to $R^{28'}$, $R^{31'}$ to $R^{38'}$, $R^{3a'}$, $R^{3b'}$, $R^{41'}$ to $R^{48'}$, $R^{4a'}$, $R^{51'}$ to $R^{58'}$, and $R^{61'}$ to $R^{68'}$ in the general formula (1'), reference may be made to the descriptions of the compound represented by the general formula (1), provided that such a case is excluded that $R^{2'}$ and $R^{7'}$ each represent a group represented by the general formula (2) and all $R^{21'}$ to $R^{28'}$ represent hydrogen atoms. Examples of the case where both $R^{2'}$ and $R^{7'}$ are substituted include the compound that is substituted by a. group represented by any of the general formulae (3') to (6')

Synthesis Method of Compound Represented by General Formula (1')

The compound represented by the general formula (1) may be synthesized by combining the known reactions. For example, the compound represented by the general formula (1') in which. $R^{3'}$ and $R^{6'}$ each represent a group represented by the general formula (3'), can be synthesized through reaction of the following two compounds.

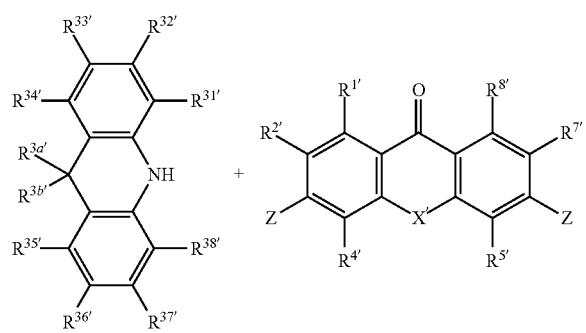

In the aforementioned reaction scheme, for the descriptions of $R^{1\prime}$ to $R^{5\prime}$, $R^{7\prime}$, $R^{8\prime}$, $R^{31\prime}$ to $R^{38\prime}$, $R^{3a\prime}$ and $R^{3b\prime}$, reference may be made to the corresponding descriptions in the general formula (1'), and Z represents a halogen atom, examples of which include a fluorine atom, a chlorine atom, a bromine atom and an iodine atom, and a chlorine atom, a bromine atom and an iodine atom are preferred.

The aforementioned reaction is an application of the known coupling reaction, and the known reaction conditions may be appropriately selected and used. For the details of the reactions, reference may be made to the synthesis examples described later. The compound represented by the general formula (1') may also be synthesized by combining the other known synthesis reactions.

Organic Light Emitting Device

The compound represented by the general formula (1) of the invention is useful as a light emitting material of an organic light emitting device. Accordingly, the compound represented by the general formula (1) of the invention may be effectively used as a light emitting material in a light emitting layer of an organic light emitting device. The compound represented by the general formula (1) includes a delayed fluorescent material emitting delayed fluorescent light (delayed fluorescent emitter). Thus, the invention provides an invention relating to a delayed fluorescent emitter having the structure represented by the general formula (1), an invention relating to the use of the compound represented by the general formula (1) as the delayed fluorescent emitter, and an invention relating to a method for emitting delayed fluorescent light with the compound represented by the general formula (1). An organic light emitting device that uses the compound as a light emitting material has features that the device emits delayed fluorescent light and has a high light emission efficiency. The principle of the features may be described as follows for an organic electroluminescent device as an example.

In an organic electroluminescent device, carriers are injected from an anode and a cathode to a light emitting material to form an excited state for the light emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy use efficiency. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light emitting material of a light emitting layer may provide an excellent organic light emitting device, such as an organic photoluminescent device (organic PL device) and an organic electroluminescent device (organic EL device). At this time, the compound represented by the general formula (1) of the invention may have a function of assisting light emission of another light emitting material contained in the light emitting layer, i.e., as a so-called assist dopant. Specifically, the compound represented by the general formula (1) of the invention contained in the light emitting layer may have a lowest excited singlet energy level that is between the lowest excited singlet energy level of the host material contained in the light emitting layer and the lowest excited singlet energy level of the another light emitting material contained in the light emitting layer.

The organic photoluminescent device has a structure containing a substrate having formed thereon at least a light emitting layer. The organic electroluminescent device has a structure containing at least an anode, a cathode and an organic layer formed between the anode and the cathode. The organic layer contains at least a light emitting layer, and may be formed only of a light emitting layer, or may have one or more organic layer in addition to the light emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, denotes a light emitting layer, 6 denotes an electron transporting layer, and 7 denotes a cathode.

The members and the layers of the organic electroluminescent device will be described below. The descriptions for the substrate and the light emitting layer may also be applied to the substrate and the light emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light Emitting Layer

The light emitting layer is a layer, in which holes and electrons injected from the anode and the cathode, respectively, are recombined to form excitons, and then the layer emits light. A light emitting material may be solely used as the light emitting layer, but the light emitting layer preferably contains a light emitting material and a host material. The light emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light emitting material are confined in the light emitting material. Accordingly, a host material is preferably used in addition to the light emitting material in the light emitting layer. The host material used may be an organic compound that has excited singlet energy and excited triplet energy, at least one of which is higher than those of the light emitting material of the invention. As a result, the singlet excitons and the triplet excitons generated in the light emitting material of the invention are capable of being confined in the molecules of the light emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light emitting device and the organic electroluminescent device of the invention, the light emission occurs in the light emitting material of the invention contained in the light emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light emitting material contained in the light emitting layer is preferably 0.1% by weight or more, and more preferably 1% by weight or more, and is preferably 50% by weight or less, more preferably 20% by weight or less, and further preferably 10% by weight or less.

The host material in the light emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light emitting layer or the hole transporting layer and between the cathode and the light emitting layer or the electron transporting layer. The injection layer may be provided depending on necessity.

Barrier Layer

The barrier layer is a layer that is capable of inhibiting charges (electrons or holes) and/or excitons present in the light emitting layer from being diffused outside the light emitting layer. The electron barrier layer may be disposed between the light emitting layer and the hole transporting layer, and inhibits electrons from passing through the light emitting layer toward the hole transporting layer. Similarly, the hole barrier layer may be disposed between the light emitting layer and the electron transporting layer, and inhibits holes from passing through the light emitting layer toward the electron transporting layer. The barrier layer may also be used for inhibiting excitons from being diffused outside the light emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light emitting layer.

Exciton Barrier Layer

The exciton barrier layer is a layer for inhibiting excitons generated through recombination of holes and electrons in the light emitting layer from being diffused to the charge transporting layer, and the use of the layer inserted enables effective confinement of excitons in the light emitting layer, and thereby enhances the light emission efficiency of the device. The exciton barrier layer may be inserted adjacent to the light emitting layer on any of the side of the anode and the side of the cathode, and on both the sides. Specifically, in the case where the exciton barrier layer is present on the side of the anode, the layer may be inserted between the hole transporting layer and the light emitting layer and adjacent to the light emitting layer, and in the case where the layer is inserted on the side of the cathode, the layer may be inserted between the light emitting layer and the cathode and adjacent to the light emitting layer. Between the anode and the exciton barrier layer that is adjacent to the light emitting layer on the side of the anode, a hole injection layer, an electron barrier layer and the like may be provided, and between the cathode and the exciton barrier layer that is adjacent to the light emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light emitting layer but also in the other layers than the light emitting layer. In this case, the compound represented by the general formula (1) used in the light emitting layer and the compound represented by the general formula (1) used in the other layers than the light emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_2$ to $R_7$ each independently represent a hydrogen atom or a substituent, and n represents an integer of from 3 to 5.

Preferred examples of a compound that may also be used as the host material of the light emitting layer are shown below.

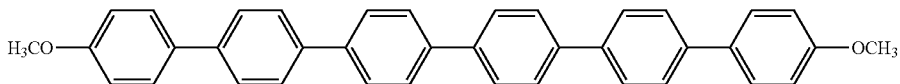

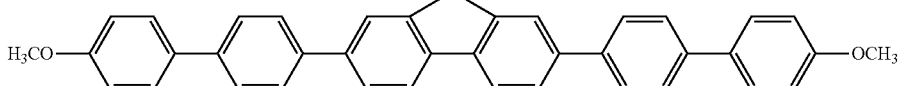

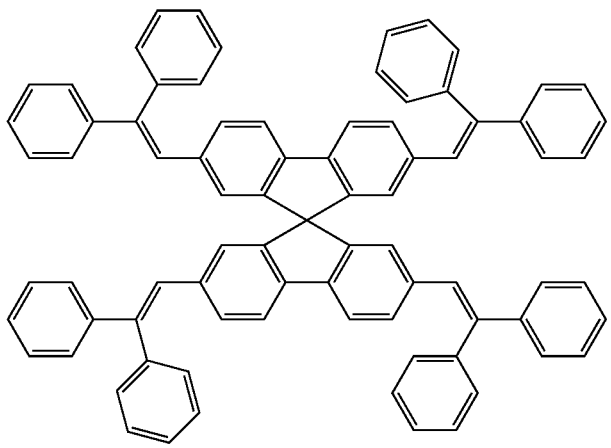

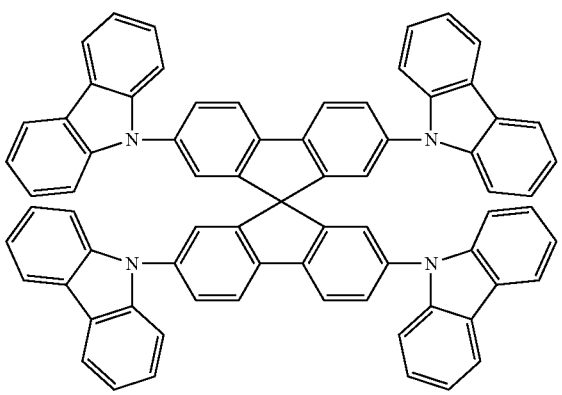

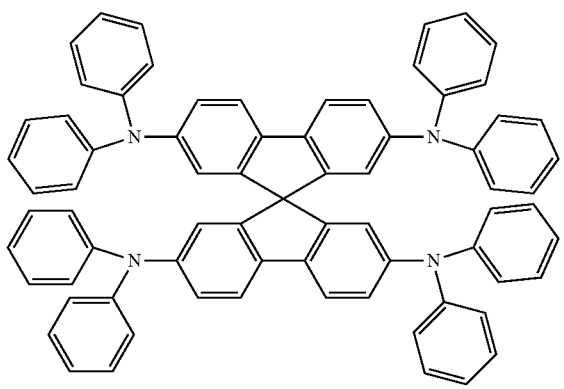

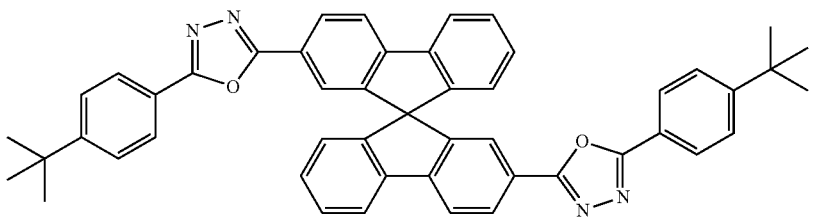

-continued
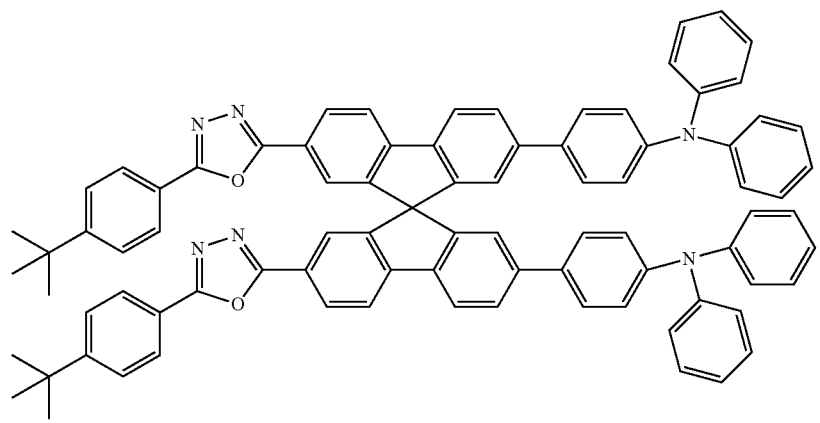
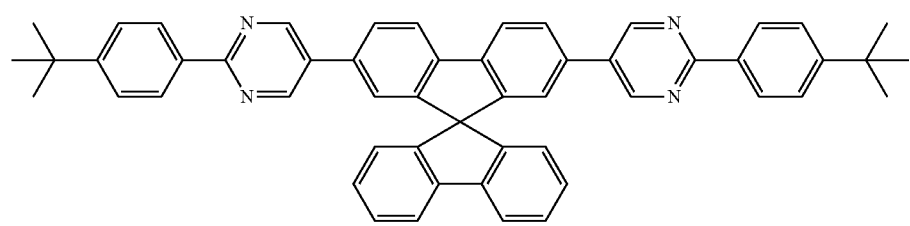
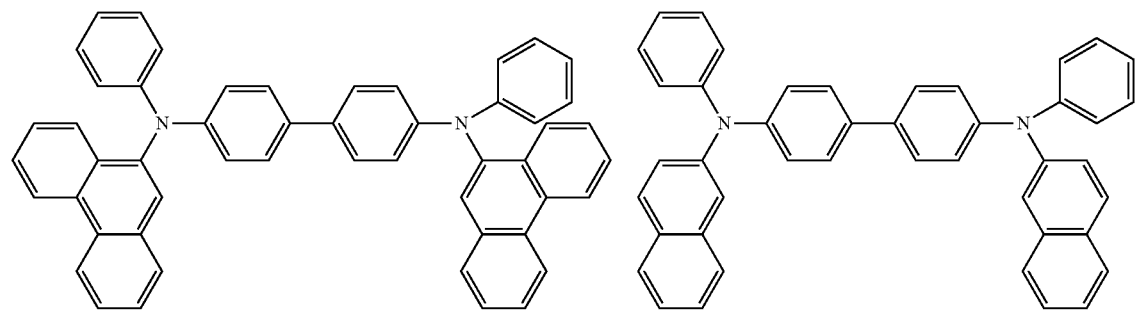
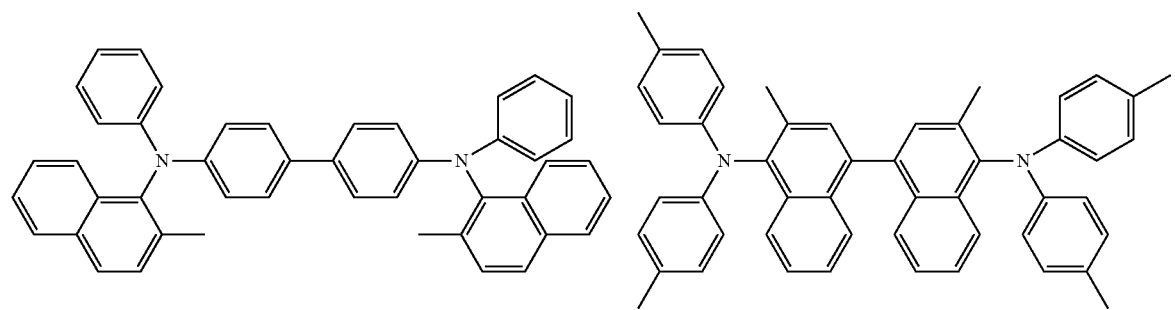

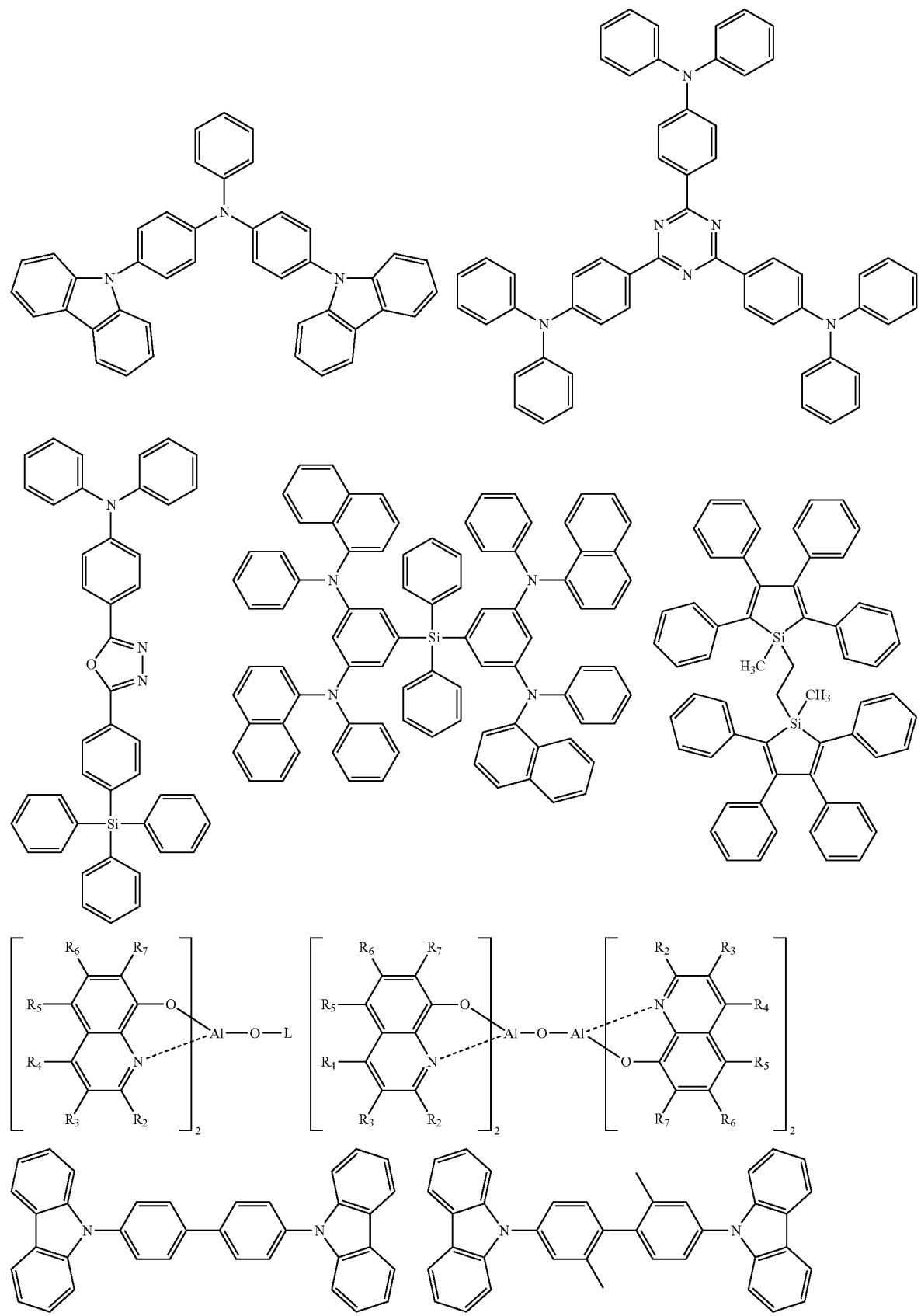

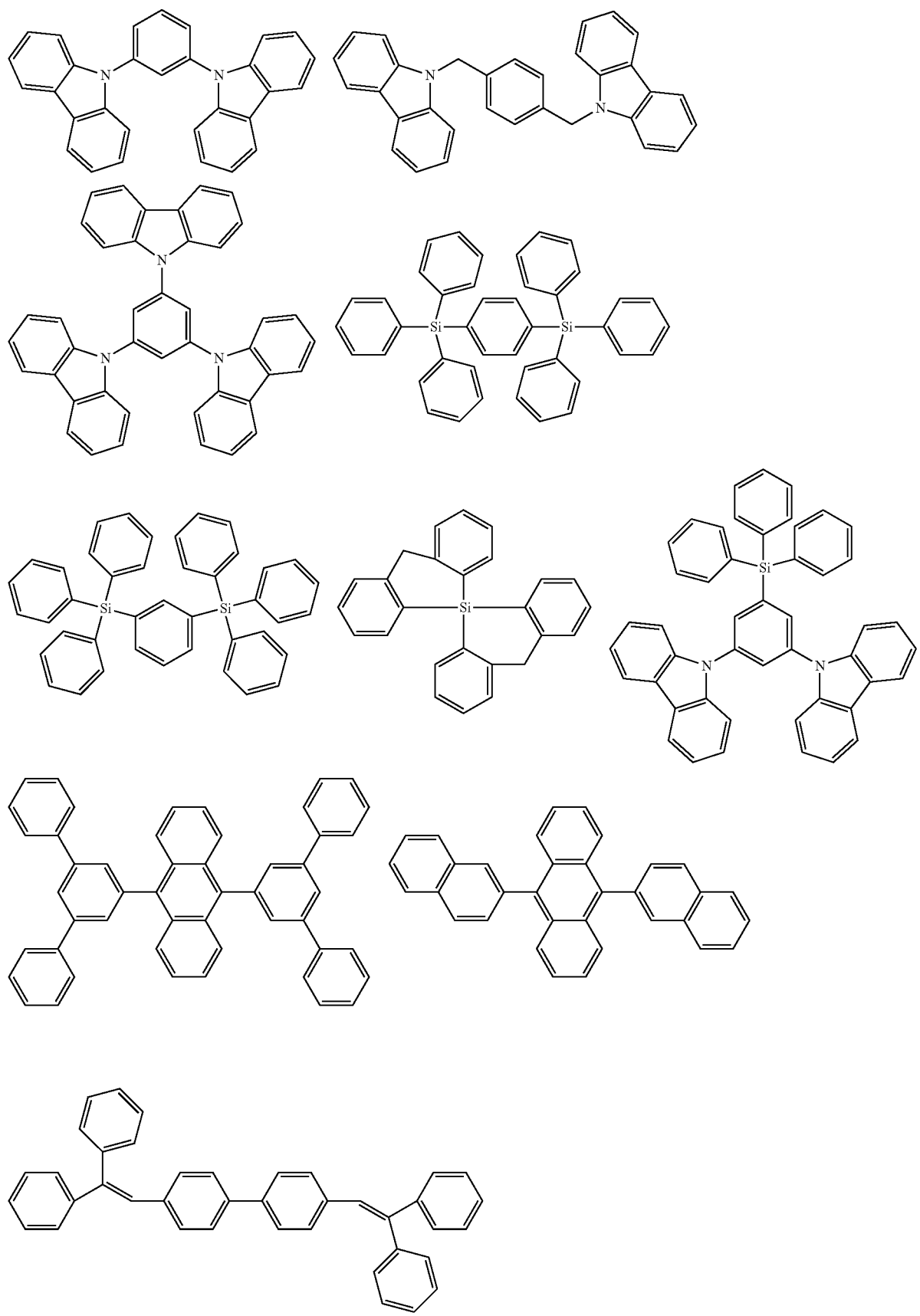

-continued
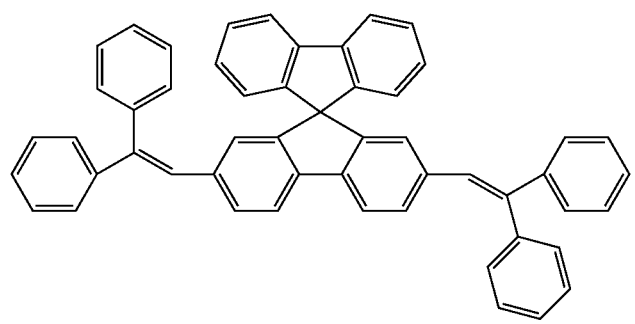
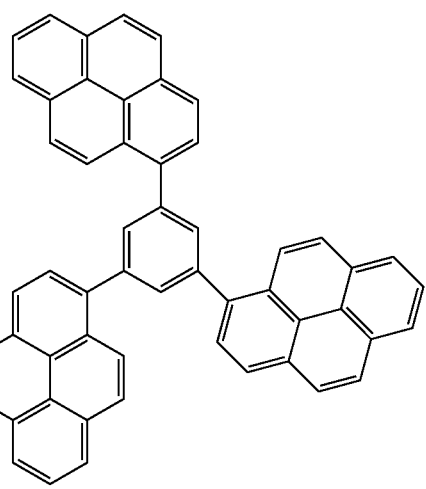
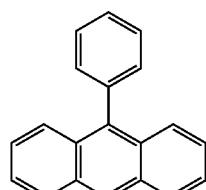
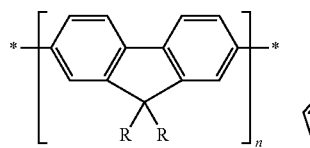
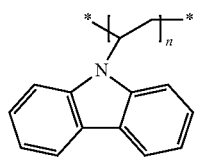
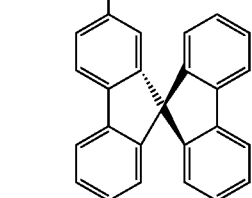
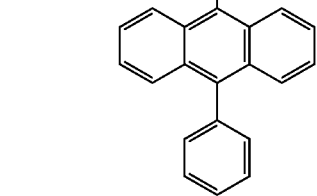
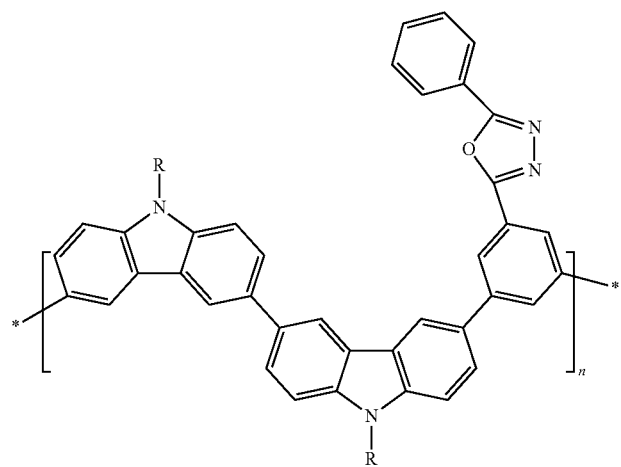
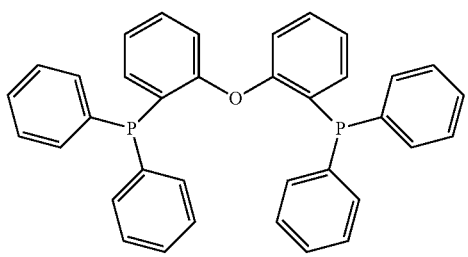

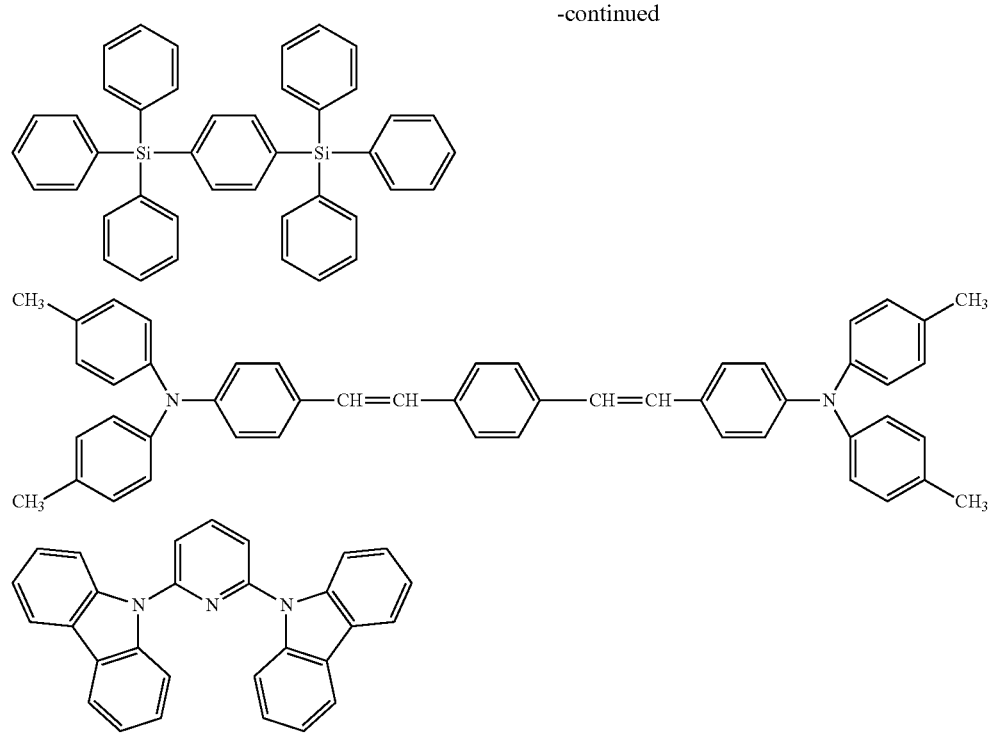
Preferred examples of a compound that may be used as the hole injection material are shown below.
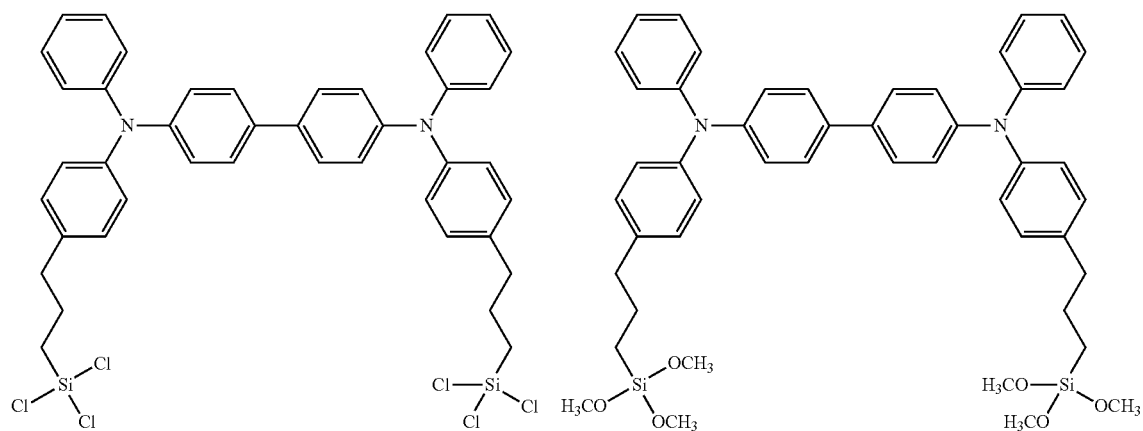
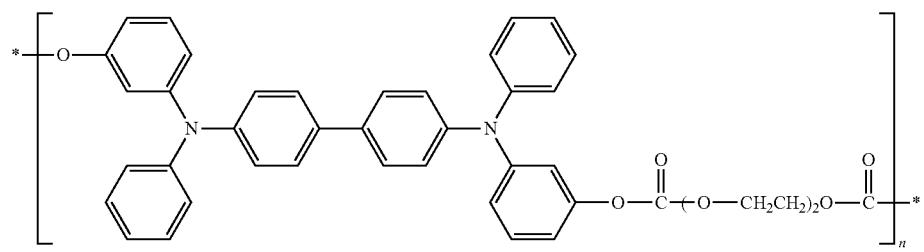

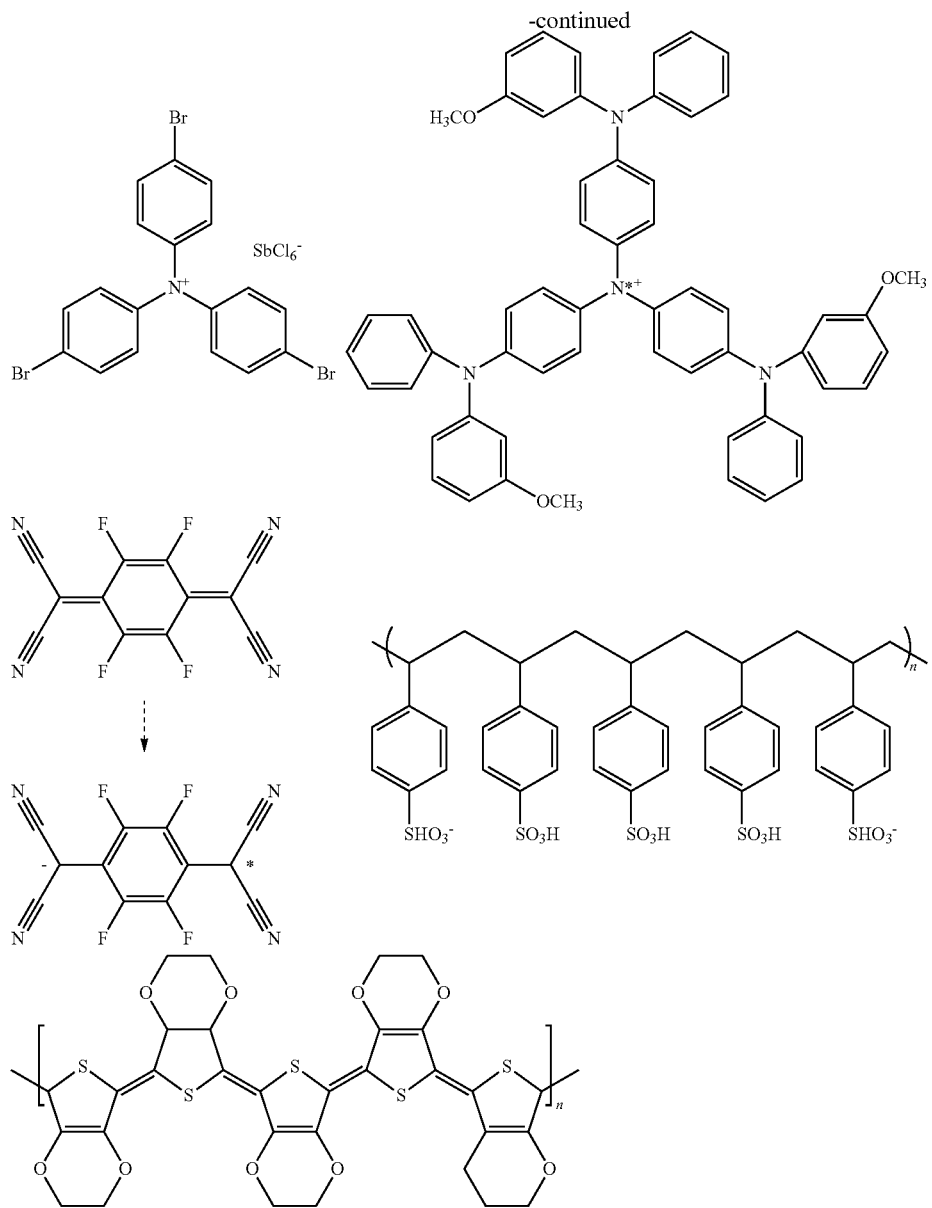
Preferred examples of a compound. that may be used as the hole transporting material are shown below.
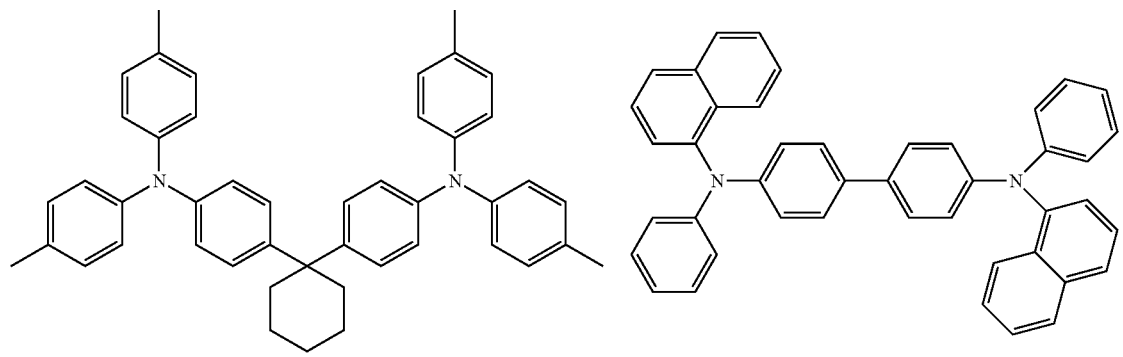

-continued
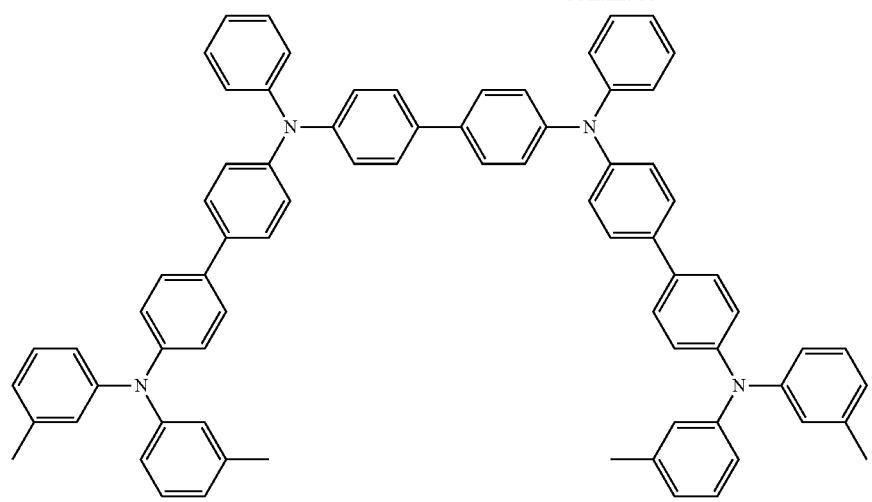
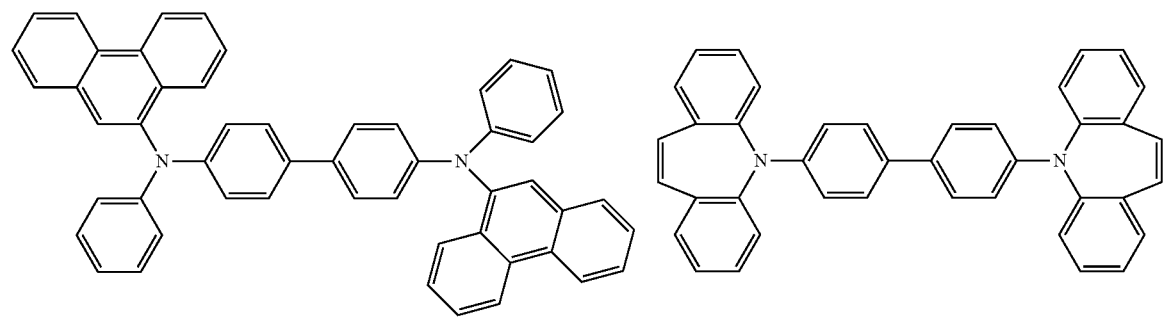
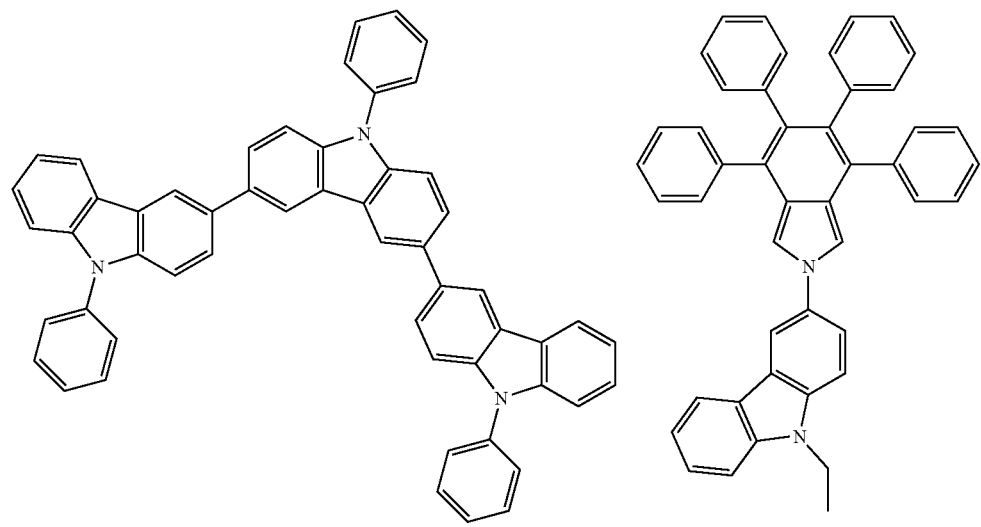

-continued
61
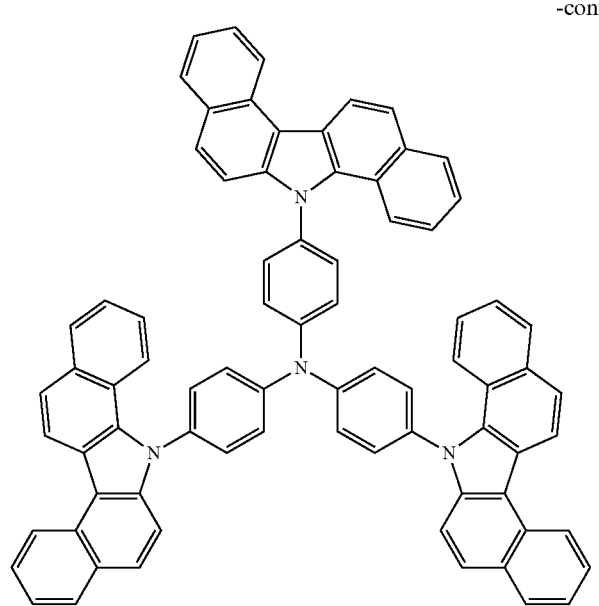
62
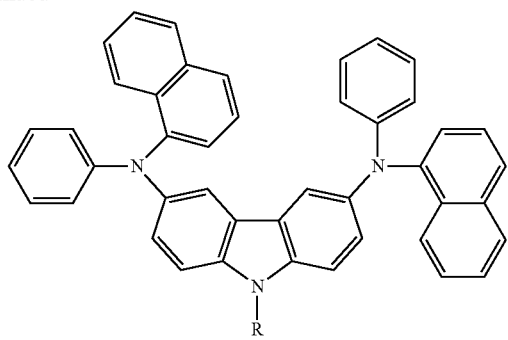
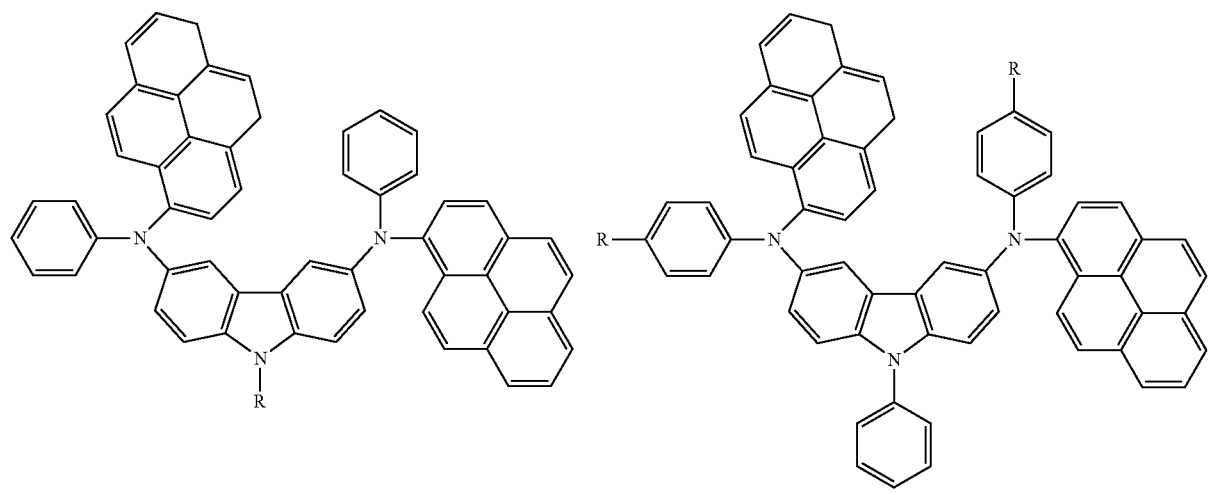
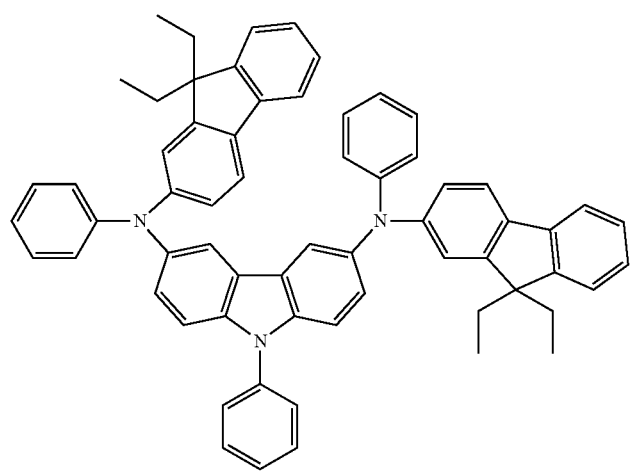

-continued
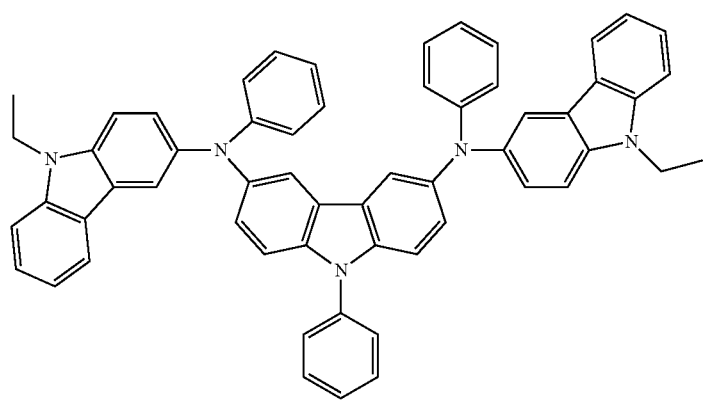
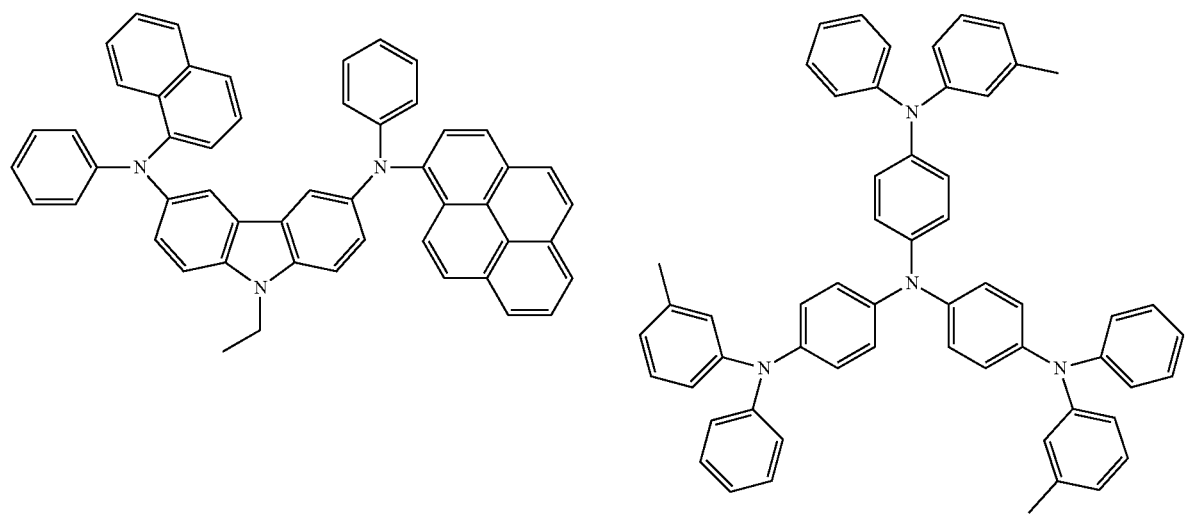
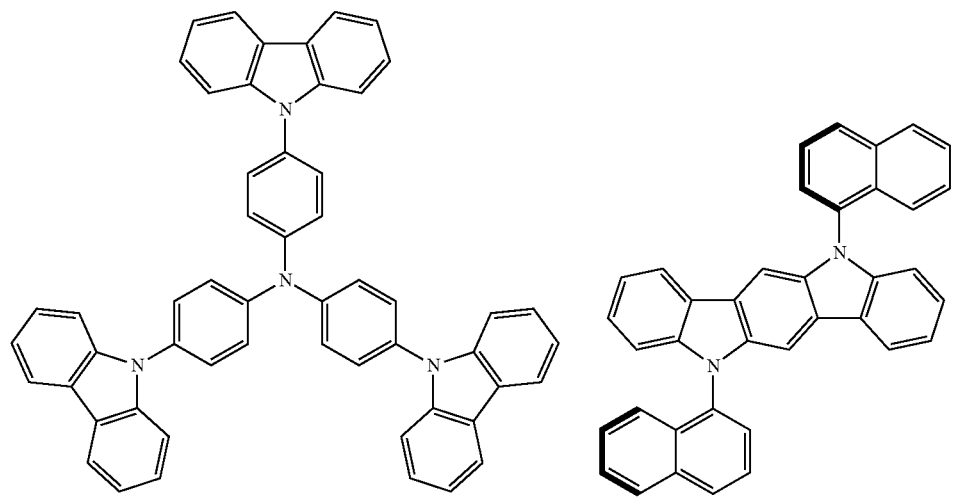

-continued
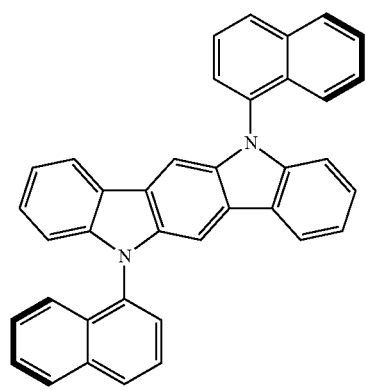
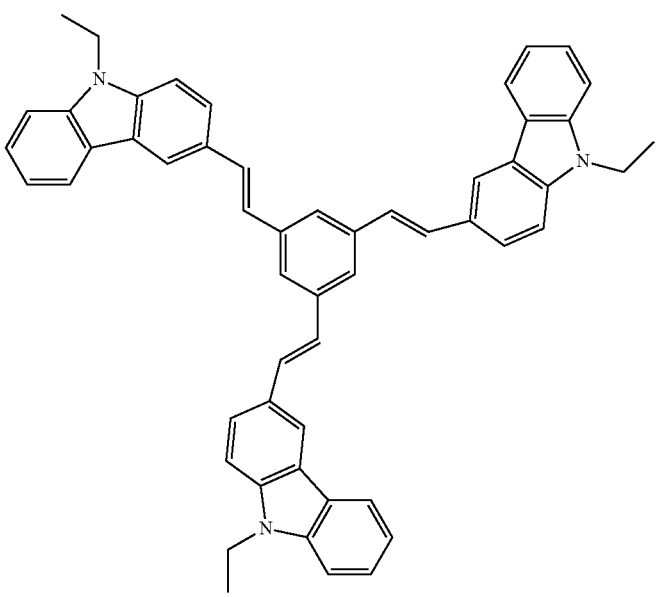
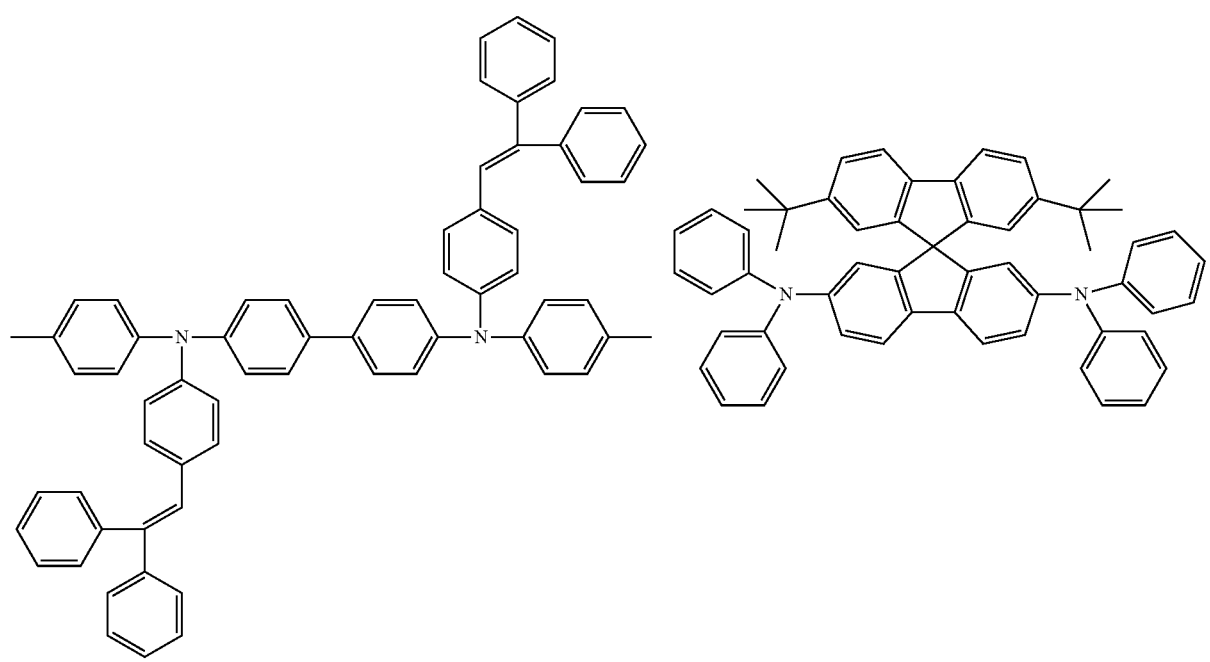
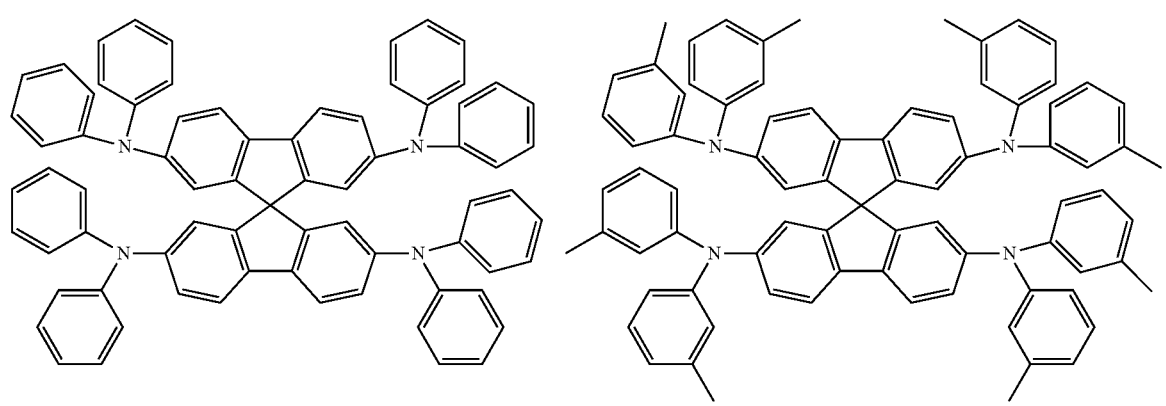

-continued
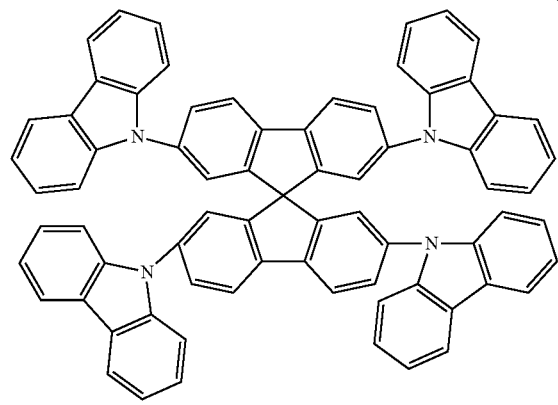
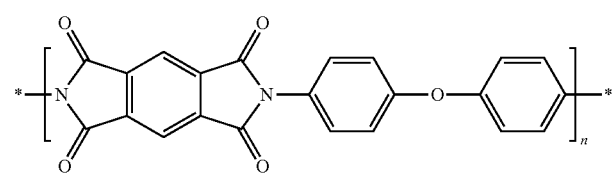
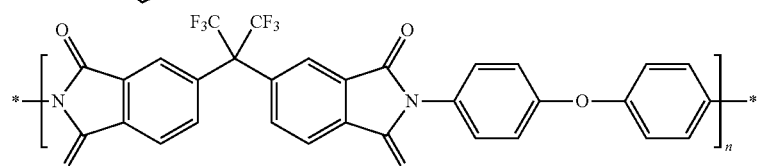
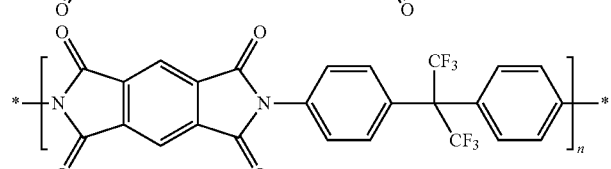
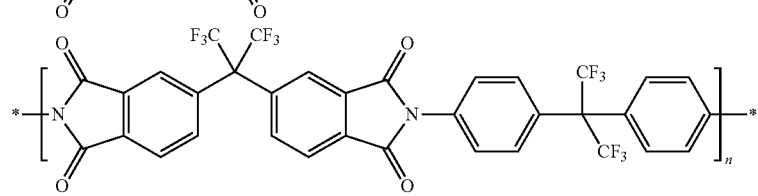
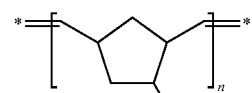
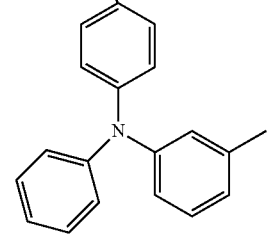
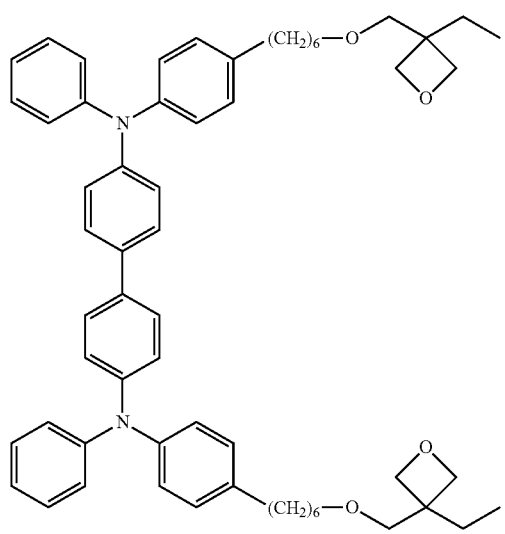
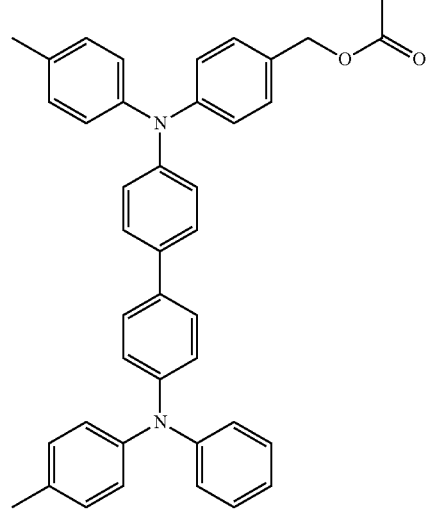

-continued
R =
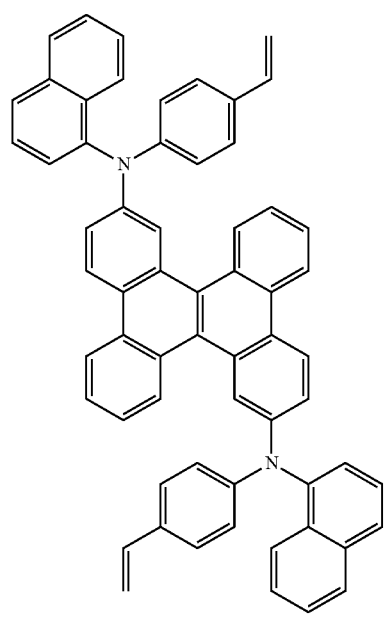
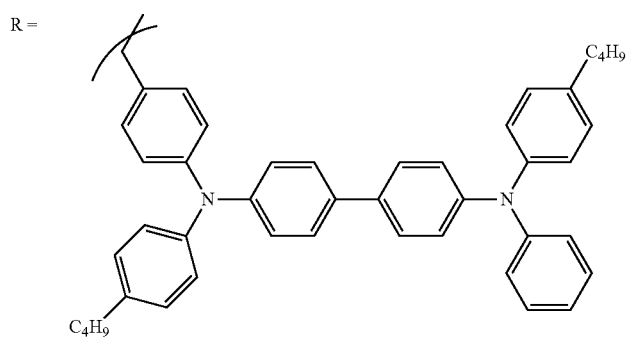
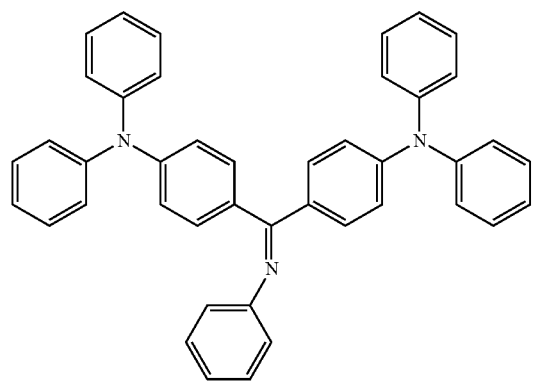
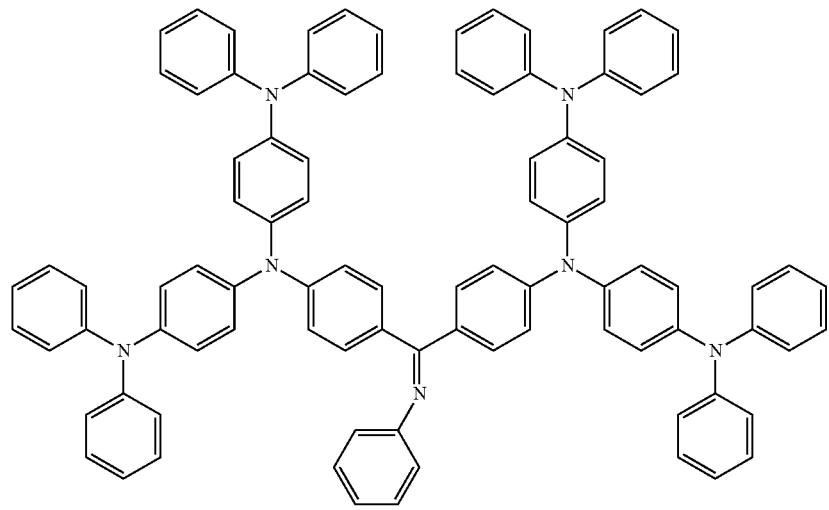

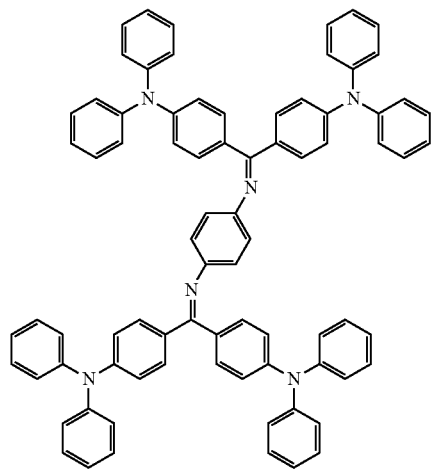
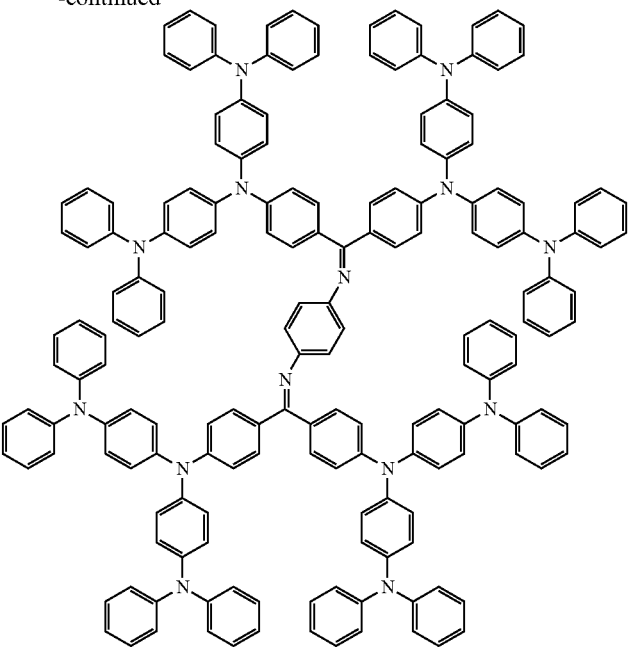
Preferred examples of a compound that may be used as the electron barrier material are shown below.
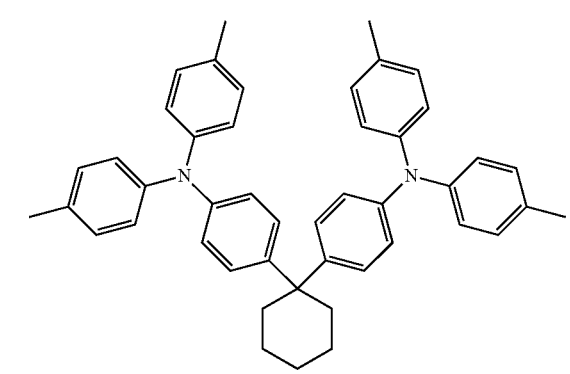
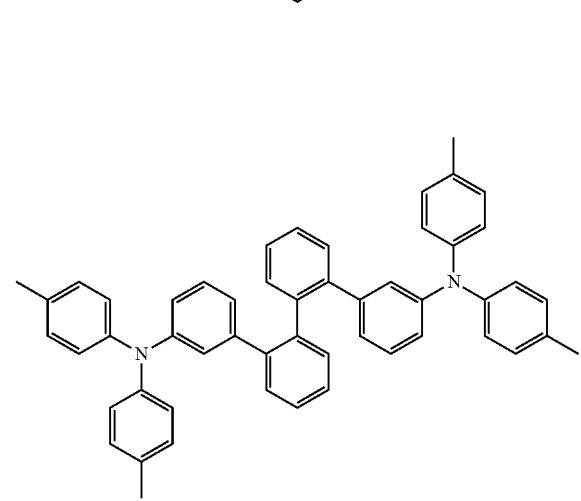
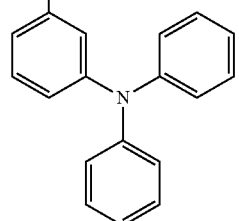
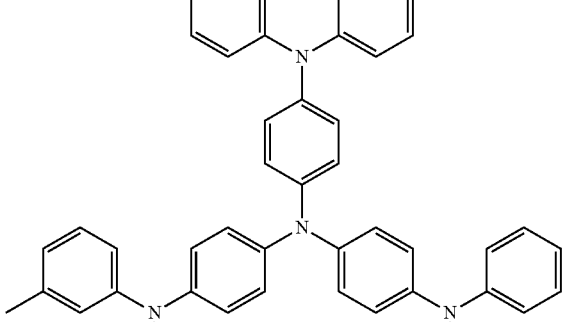
Preferred examples of a compound that may be used as the hole barrier material are shown below.

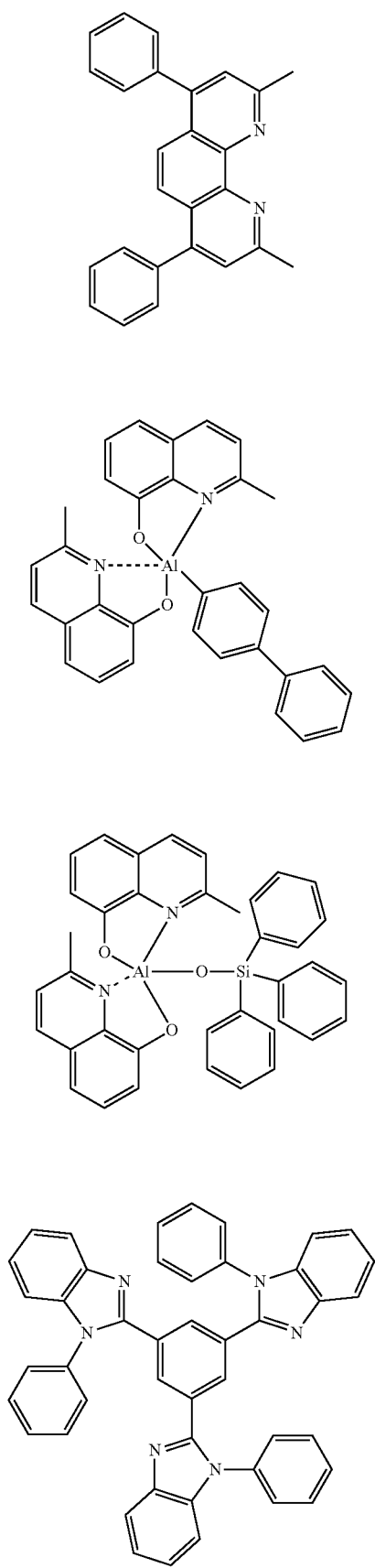
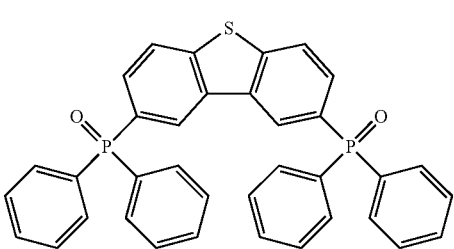

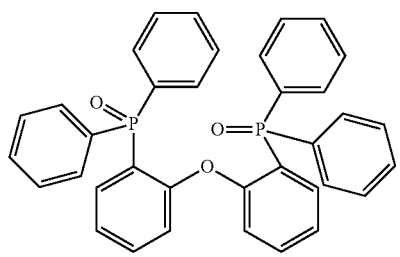
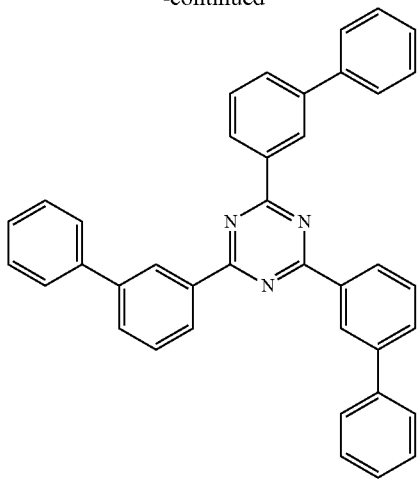
Preferred examples of a compound that may be used as the electron transporting material are shown below.
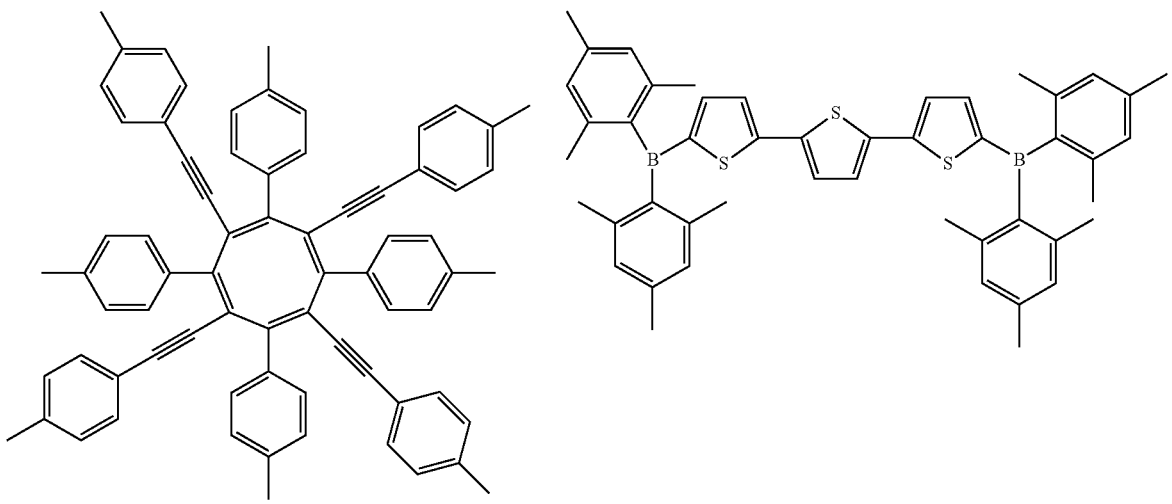
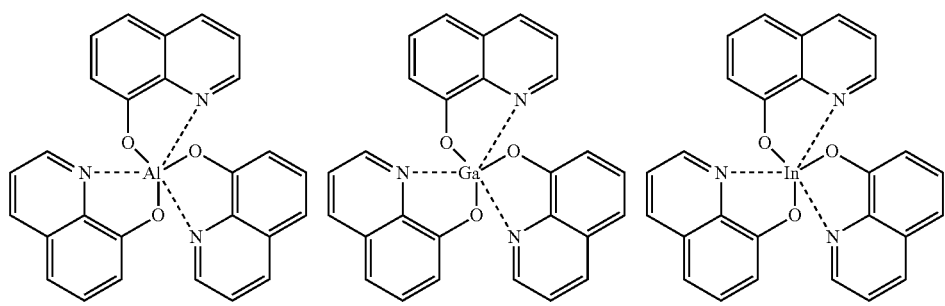

-continued
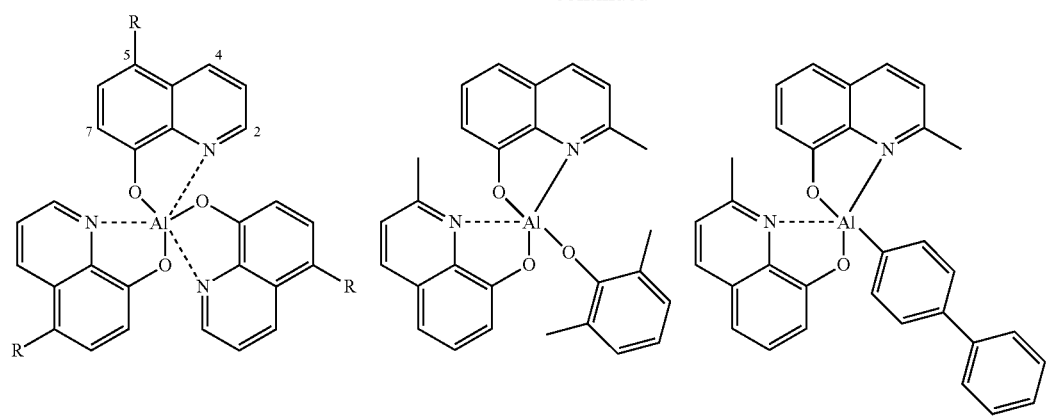
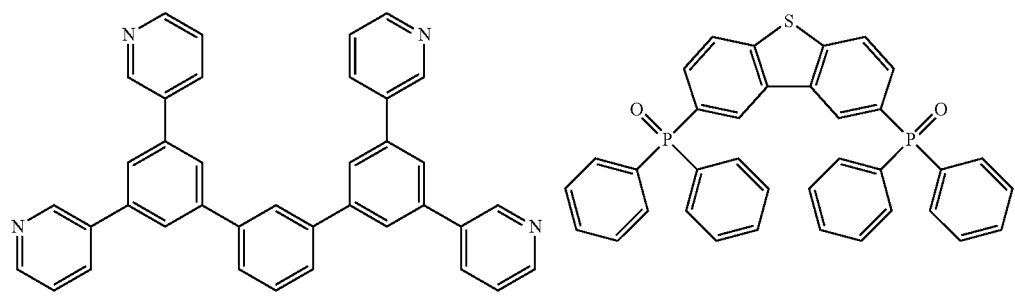
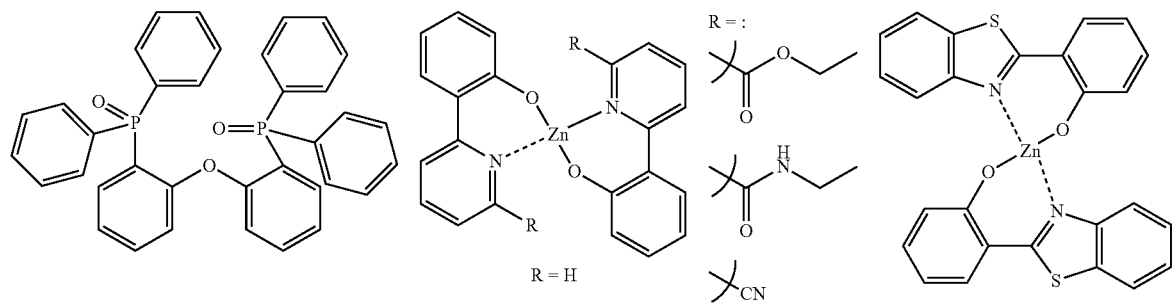
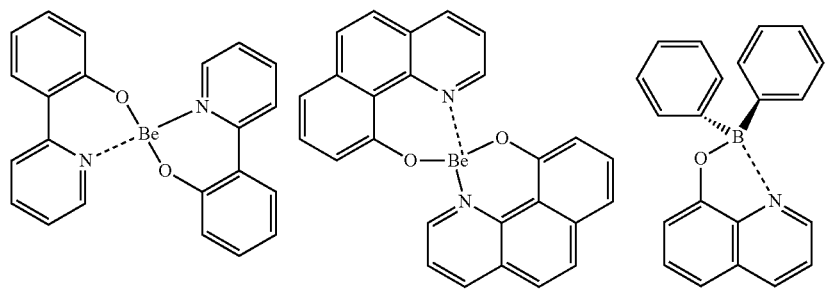

-continued
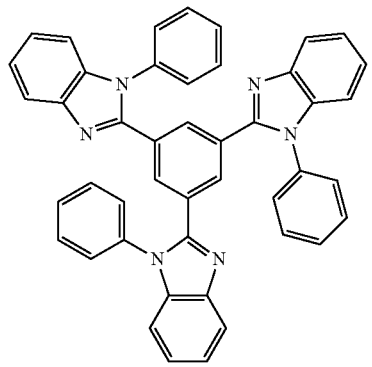
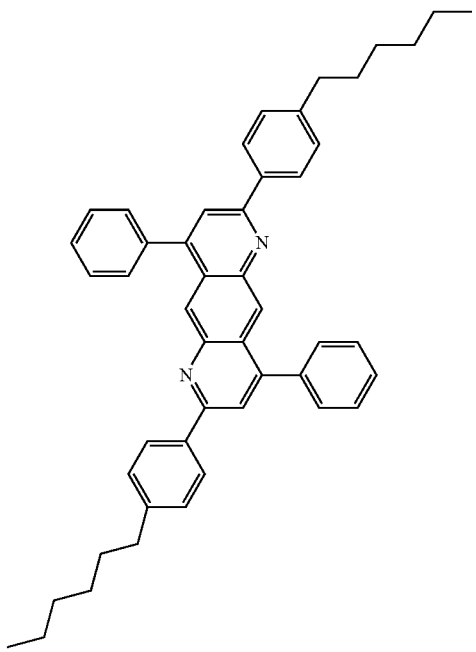
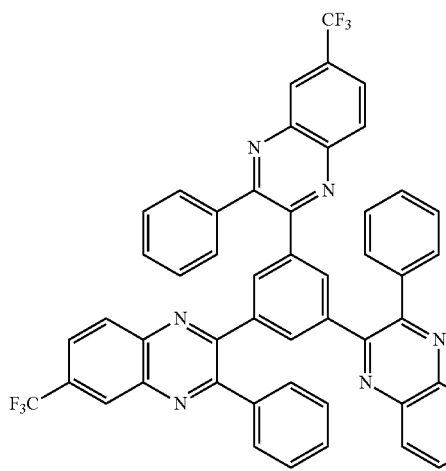
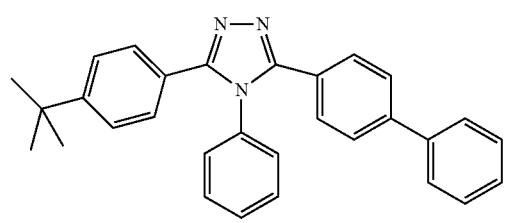
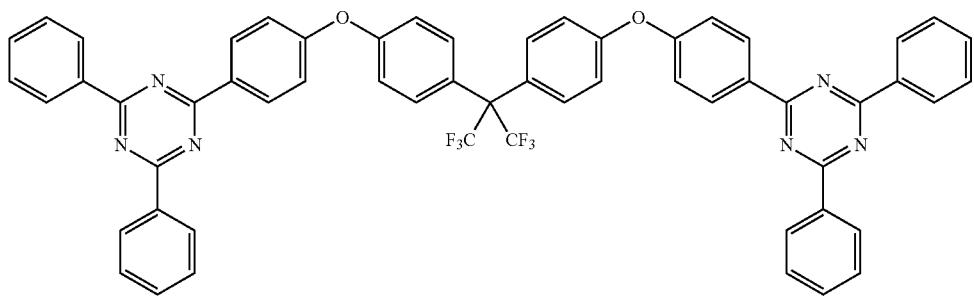

-continued
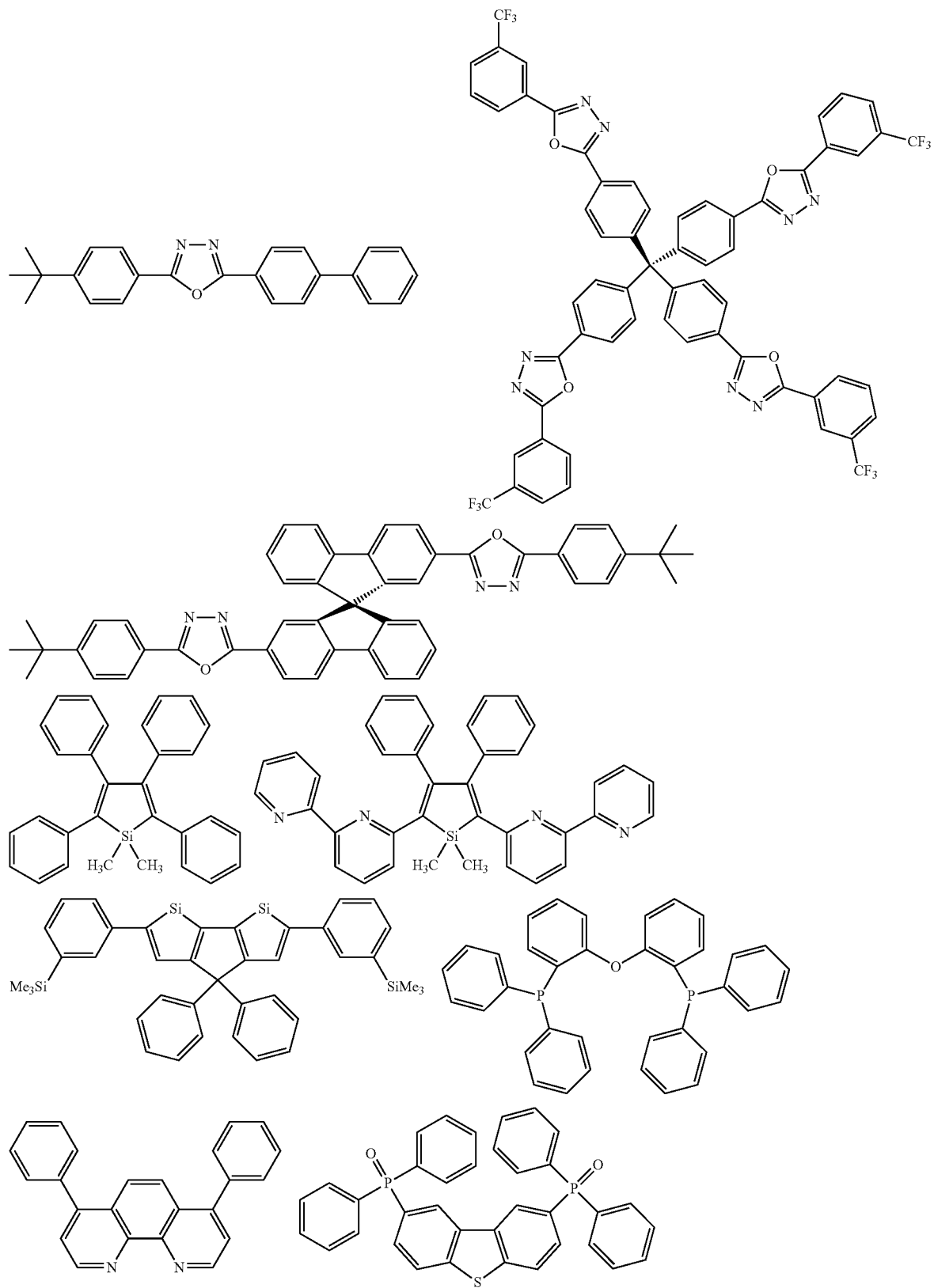

Preferred examples of a compound that may be used as the electron injection material are shown below.

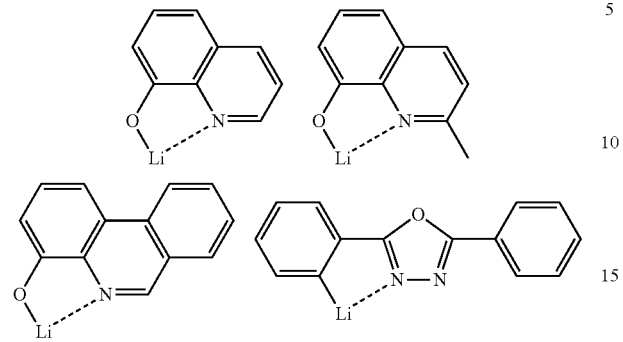

Preferred examples of a compound as a material that may be added are shown below. For example, the compound may be added as a stabilizing material.

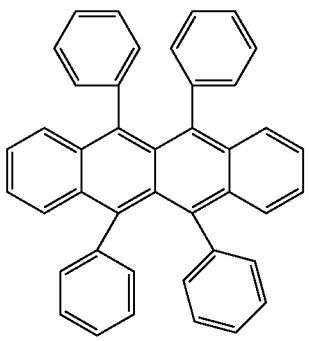

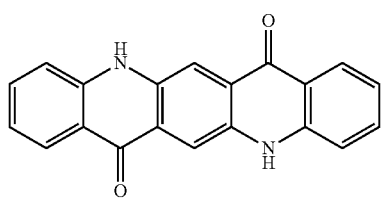

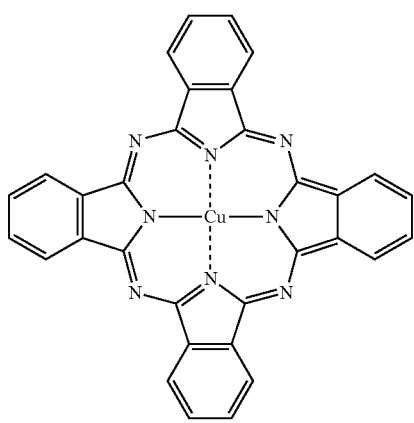

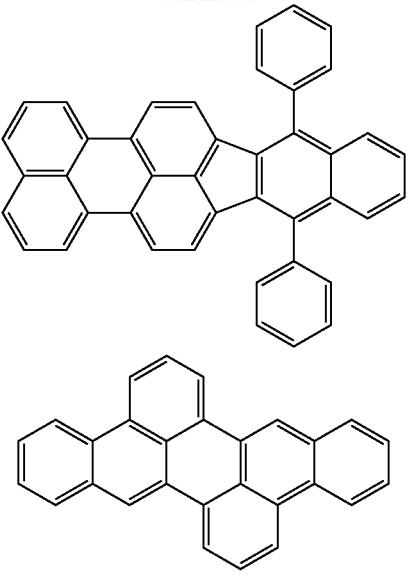

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light emitting device that is largely improved in light emission efficiency may be obtained by adding the compound represented by the general formula (1) in the light emitting layer. The organic light emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

Example

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below. The light emission characteristics were evaluated by using a high-performance UV/Vis/NIR spectrophotometer (Lambda 950, produced by PerkinElmer, Co., Ltd.), a fluorescence spectrophotometer (FluoroMax-4, produced by Horiba, Ltd.), an absolute PL quantum yield measurement system (C11347, produced by Hamamatsu Photonics K.K.), a source meter (2400 Series, produced by Keithley Instruments Inc.), a semiconductor parameter analyzer (E5273A, produced by Agilent Technologies, Inc.), an optical power meter (1930C, produced by Newport Corporation), an optical spectrometer (USB2000, produced by Ocean Optics, Inc.), a spectroradiometer (SR-3, produced by Topcon Corporation), and a streak camera (Model C4334, produced by Hamamatsu Photonics K.K.).

Synthesis Example 1

Synthesis of Compound 1

The compound 1 was synthesized according to the following procedures.

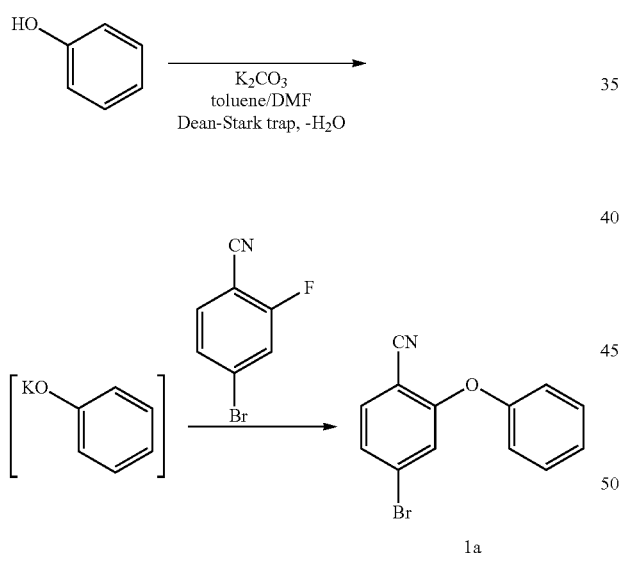

In a three-neck flask equipped with a Dean-Stark trap, phenol (12.35 g, 131.25 mmol), $K_2CO_3$ (34.55 g, 250 mmol), N,N-dimethylformamide (125 mL) and toluene (125 mL) were charged, and refluxed in a nitrogen atmosphere for 4 hours to perform dehydration until no further water was formed from the reaction system. Thereafter, 100 mL of toluene was removed with the Dean-Stark trap.

After returning to room temperature, 4-bromo-2-fluorobenzonitrile (25.0 g, 125 mmol) was added thereto, and the mixture was refluxed in a nitrogen atmosphere for 4 hours. After completing the reaction, the solution was diluted by adding toluene (200 mL) thereto, and then filtered with Celite. The solution was rinsed twice with water with a separating funnel, dried over anhydrous magnesium sulfate, and filtered. The product was purified by silica gel chromatography (mobile phase: toluene/ethyl acetate=9/1), and a specimen deposited through concentration of the solution was rinsed with 200 mL of hexane under application of ultrasonic wave for 5 minutes, and then filtered. The specimen was dried in vacuum (50° C. for 4 hours) to provide a white solid matter (yield amount: 31.2 g, yield: 91%). The product was identified by $^1$H-NMR and ESI-MS.

$^1$H NMR (500 MHz, CDCl$_3$, δ): 6.97 (s, 1H), 7.11 (d, 2H), 7.25-7.31 (m, 2H), 7.42-7.48 (m, 2H), 7.51 (d, 1H)

ESI-MS (m/z) (M$^+$) calcd. 272.98, found 273.09.

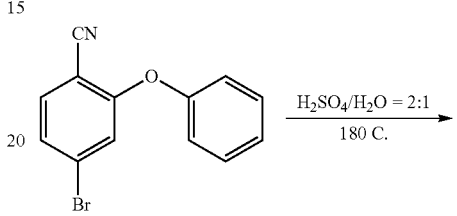

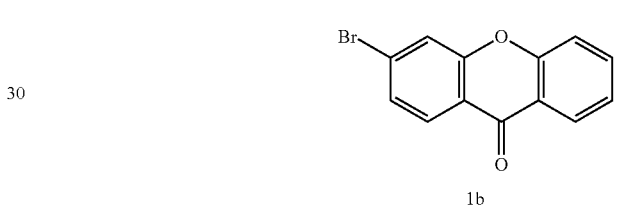

In a two-neck flask, the compound 1a (31.1 g, 113.5 mmol) water (50 ml) and sulfuric acid (100 ml) were charged, and heated under stirring in a nitrogen atmosphere at 180° C. for 12 hours. After completing the reaction, the reaction solution was cooled to room temperature, placed in water (500 mL), extracted with dichloromethane, and rinsed with water. The solution was dried over anhydrous magnesium sulfate, passed through a silica gel column to remove impurities, and then concentrated. A specimen thus deposited was rinsed under application, of ultrasonic wave in 100 ml of hexane, and filtered. The product was dried in vacuum (50° C. for 4 hours) to provide a white solid matter (yield. amount: 9.32 g, yield: 30%). The product was identified by $^1$H-NMR and ESI-MS.

$^1$H-NMR (500 MHz, CDCl$_3$, δ): 7.41 (t, 111) 7.46-7.54 (m, 2H), 7.71 (s, 1H), 7.75 (t, 1H), 8.20 (d, 1H), 8.33 (d, 1H)

ESI-MS (m/z) (M$^+$): calcd. 273.96, found 274.08.

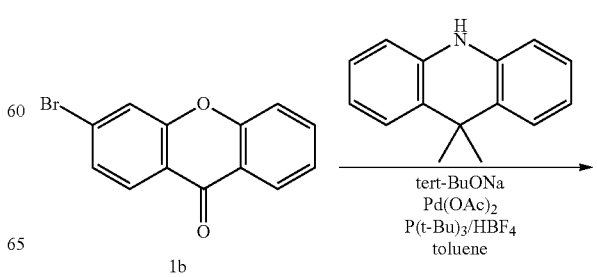

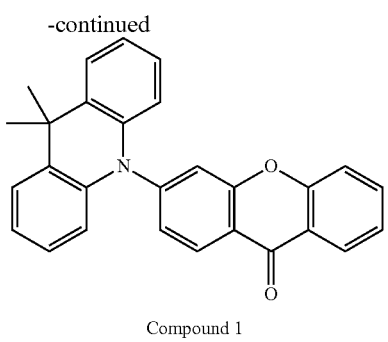

Compound 1

In a two-neck flask, the compound 1b (1.38 g, mmol) 9,9-dihydrodimethylacridine (1.15 g, 5.5 mmol), sodium tert-butexide (0.96 q, 10 mmol), palladium acetate (56 mg, 0.25 mmol) and tri-tert-butylphosphonium tetrafluoroborate (145 mg, 0.5 mmol) were charged, and after replacing the interior of the flask with nitrogen, 50 mL of dehydrated toluene was added thereto, followed by refluxing in a nitrogen atmosphere for 8 hours. After completing the reaction, the reaction. solution was cooled to room temperature, and filtered with Celite. The filtrate was concentrated, purified by silica gel 1.5 chromatography (mobile phase: dichloromethane), concentrated, and then recrystallized twice from hexane/ethyl acetate=9/1 mL/g, to provide a yellow solid matter (yield amount: 2.06 g, yield: 85%)

$^1$H-NMR (500 MHz, CDCl$_3$, δ): 1.68 (s, 6H), 6.53 (d, 2H), 6.96-7.08 (m, 4H), 7.38 (d, 1H), 7.42 (t, 1H), 7.46-7.52 (m, 3H), 7.53 (s, 1H), 7.74 (t, 1H), 8.38 (d, 1H), 8.53 (d, 1H)

EST-MS (m/z) (M$^+$) calcd. 403.16, found 403.23.

Synthesis Example 2

Synthesis of Compound 4

The compound 4 was synthesized according to the following procedures.

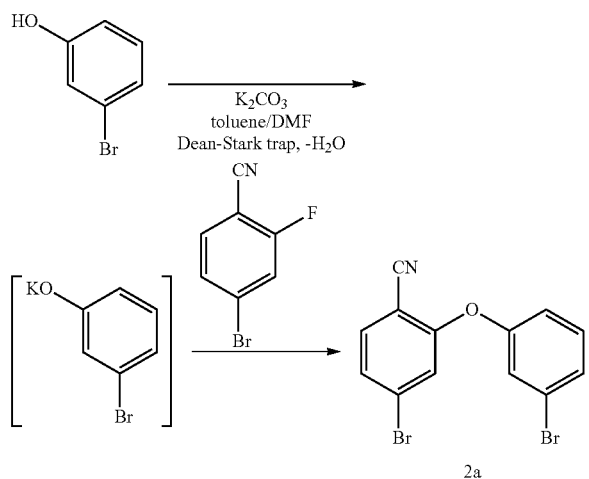

In a three-neck flask equipped with a Dean-Stark trap, 3-bromophenol (22.72 g, 131.3 mmol), K$_2$CO$_3$ (34.55 g, 250 mmol), N,N-dimethylformamide (130 mL) and toluene (130 mL) were charged, and refluxed in a nitrogen atmosphere for 4 hours to perform dehydration until no further water was formed from the reaction system. Thereafter, 100 mL of toluene was removed with the Dean-Stark trap.

After returning to room temperature, 4-bromo-2-fluorobenzonitrile (25.0 g, 125 mmol) was added thereto, and the mixture was refluxed in a nitrogen atmosphere for 4 hours. After completing the reaction, the solution was diluted by adding toluene (200 mL) thereto, and then filtered with Celite. The solution was rinsed twice with water with a separating funnel, dried over anhydrous magnesium sulfate, and filtered. The product was purified by silica gel chromatography (mobile phase: toluene/ethyl acetate=9/1), and a specimen deposited through concentration of the solution was rinsed with hexane (200 mL) under application of ultrasonic wave for 5 minutes, and then filtered. The specimen was dried in vacuum (50° C. for 4 hours) to provide a white solid matter (yield amount: 43.8 g, yield: 99%). The product was identified by $^1$H-NMR and ESI-MS.

$^1$H-NMR (500 MHz, CDCl$_3$, δ): 7.02 (d, 1H), 7.05 (d, 1H), 7.27 (t, 1H), 7.29-7.35 (m, 2H), 7.41 (d, 1H), 7.53 (d, 1H)

ESI-MS (m/z) (M$^+$): calcd. 350.89, found 351.04.

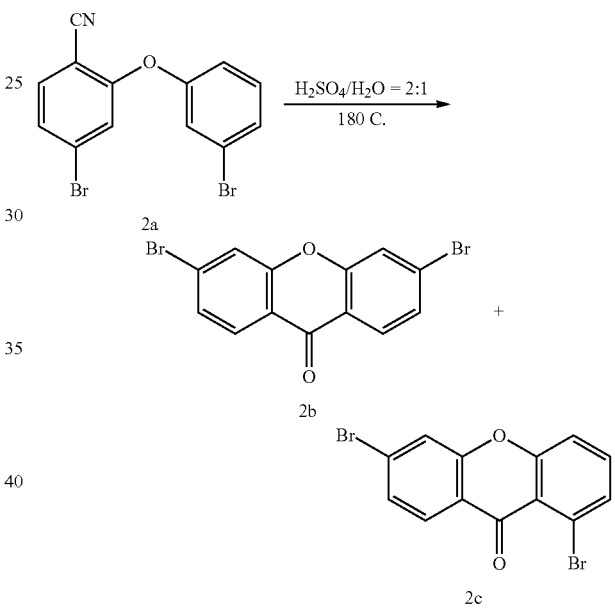

In a two-neck flask, the compound 2a (39.18 g, 111 mmol), water (55 mL) and sulfuric acid (111 mL) were charged, and heated under stirring in a nitrogen atmosphere at 180° C. for 18 hours. After completing the reaction, the reaction solution was cooled to room temperature, placed in water (500 mL), extracted with dichloromethane, rinsed twice with water, and rinsed with a sodium hydroxide aqueous solution. The solution was dried over anhydrous magnesium sulfate, passed through a silica gel column to remove impurities, and then concentrated. The product was separated into compounds 2b and 2c by silica gel chromatography (mobile phase: dichloromethane), and the compound 2b was recrystallized from approximately 10 mL/g of a toluene solution. For the compound 2c, approximately 5 mL/g of a toluene solution was prepared for the compound, to which approximately 5 mL/g of methanol was added to perform recrystallization. The products were dried in vacuum (50° C. for 4 hours) to provide a white solid matter (2b: yield amount: 13.08 g, yield: 33%; 2c: yield amount: 14.82 g, yield: 38%). The product was identified by $^1$H-NMR and ESI-MS.

Compound 2b

¹H-NMR (500 MHz, CDCl₃, δ): 7.52 (d, 2H), 7.69 (s, 2H), 8.07 (d, 2H)

ESI-MS (m/z) (M⁺): calcd. 351.87, found 351.53.

Compound 2c

¹H-NMR (500 MHz, CDCl₃, δ): 7.44-7.54 (m, 3H), 7.65 (dd, 2H), 8.17 (d, 1H)

ESI-MS (m/z) (M⁺): calcd. 351.87, found 351.53.

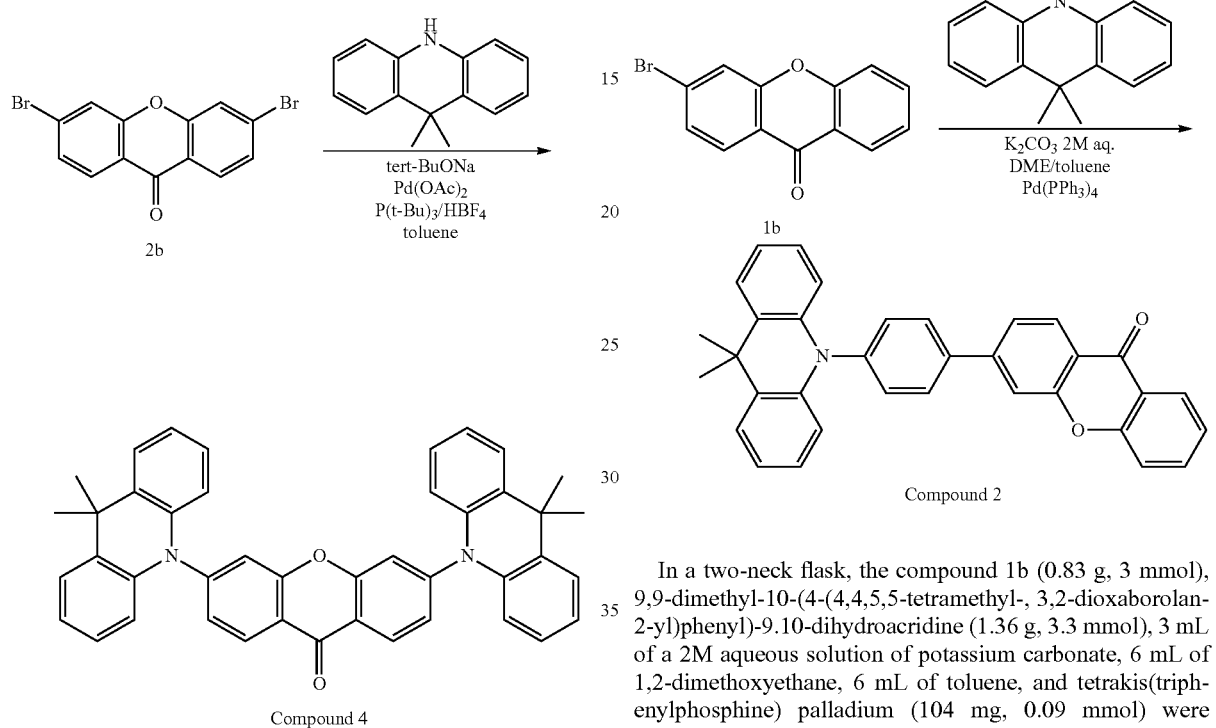

The synthesis was performed in the same manner as in the compound 1 in Synthesis Example 1 except that the raw material was changed to the compound 1b to the compound 2b (yield amount: 4.45 g, yield: 73%).

¹H-NMR (500 MHz, CDCl₃, δ) 1.69 (s, 12H), 6.57 (d, 4H), 6.98-7.11 (m, 8H), 7.4.1 (d, 2H), 7.47-7.55 (m, OH), 8.57 (d, 2H)

ESI-MS (m/z) (M⁺): calcd. 610.26, found 610.27.

Synthesis Example 3

Synthesis of Compound 2

The synthesis was performed according to the following reaction scheme in the same manner as is the compound 1 in Example 1 (yield: 97%).

In a two-neck flask, the compound 1b (0.83 g, 3 mmol), 9,9-dimethyl-10-(4-(4,4,5,5-tetramethyl-, 3,2-dioxaborolan-2-yl)phenyl)-9.10-dihydroacridine (1.36 g, 3.3 mmol), 3 mL of a 2M aqueous solution of potassium carbonate, 6 mL of 1,2-dimethoxyethane, 6 mL of toluene, and tetrakis(triphenylphosphine) palladium (104 mg, 0.09 mmol) were charged, and refluxed in a nitrogen atmosphere for 48 hours.

After completing the reaction, the reaction solution was extracted with dichloromethane with a separating funnel, dried over anhydrous magnesium sulfate, then filtered, and concentrated. The product was purified by silica gel chromatography (mobile phase: dichloromethane). The product was further rinsed with 30 mL of an ethyl acetate/n-hexane mixed solvent (1/1) under application of ultrasonic wave for 5 minutes, and then filtered. The product was dried in vacuum at 50° C. for 6 hours to provide a pale yellow solid matter (yield amount: 1.4 g, yield: 97%). The product was identified by ¹H-NMR and ESI-MS.

¹H-NMR (500 MHz, CDCl₃, δ): 1.72 (S, 6H), 6.36 (d, 2H), 6.92-7.05 (m, 4H), 7.43 (t, 1H), 7.43-7.52 (m, 4H), 7.56 (d, 1H), 7.72-7.81 (m, 2H), 7.83 (s, 1H), 7.97 (d, 2H), 8.39 (d, 1H), 8.47 (d, 1H)

ESI-MS (m/z) (M⁺): calcd. 479.19, found 479.34.

Synthesis Example 4

Synthesis of Compound 3

The synthesis was performed according to the following reaction scheme in the same manner as in the compound 1 in Example 1 (yield: 68%).

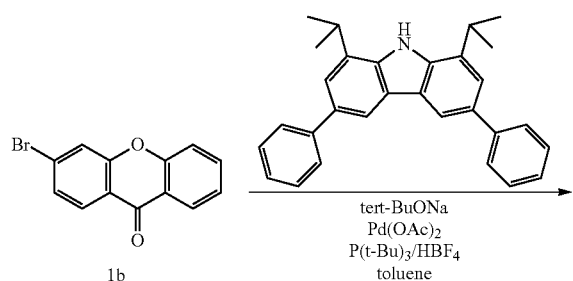

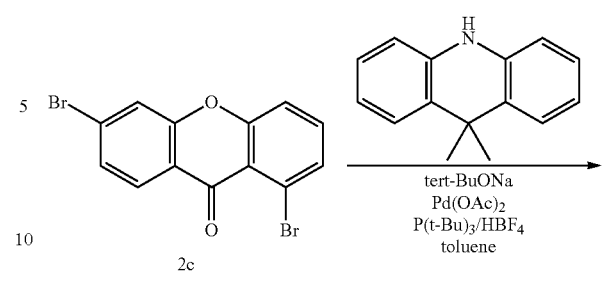

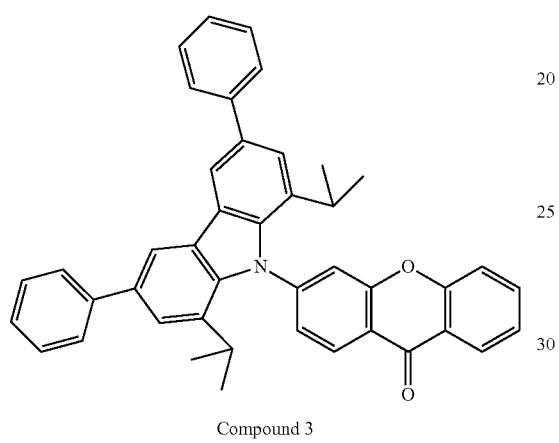

Compound 3

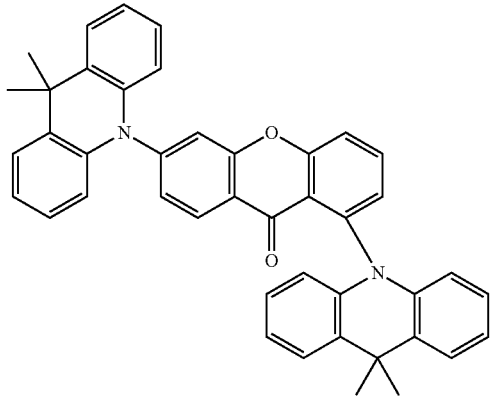

Compound 5

¹H-NMR (500 MHz, CDCl₃, δ): 1.67 (3, 6H), 1.77 (s, 3H), 1.96 (s, 3H), 6.05 (dd, 2H), 6.46 (d, 2H), 6.85-6.93 (m, 4H), 6.97-7.07 (m, 4H), 7.24 (d, 1H), 7.31 (d, 1H), 7.46-7.54 (m, 5H), 7.70 (d, 1H), 7.93 (t, 1H), 8.29 (d, 1H)

ESI-MS (m/z) (M⁺) calcd. 610.26, found 610.27.

Synthesis Example 5

Synthesis of Compound 5

The synthesis was performed according to the following reaction scheme in the same manner as in the compound 1 in Example 1 (yield: 34%)

Synthesis Example 6

Synthesis of Compound 6

The synthesis was performed according to the following reaction scheme in the same manner as in the compound 4 in Example 2 (yield: 19%).

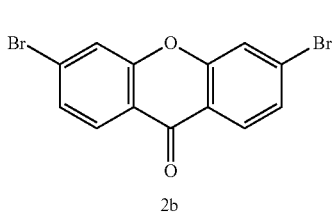

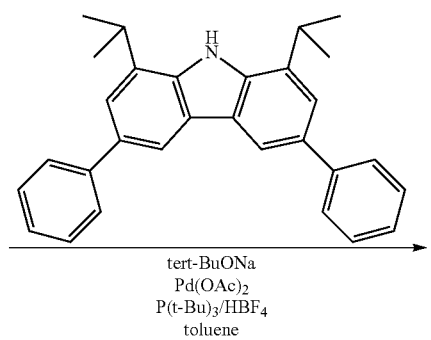

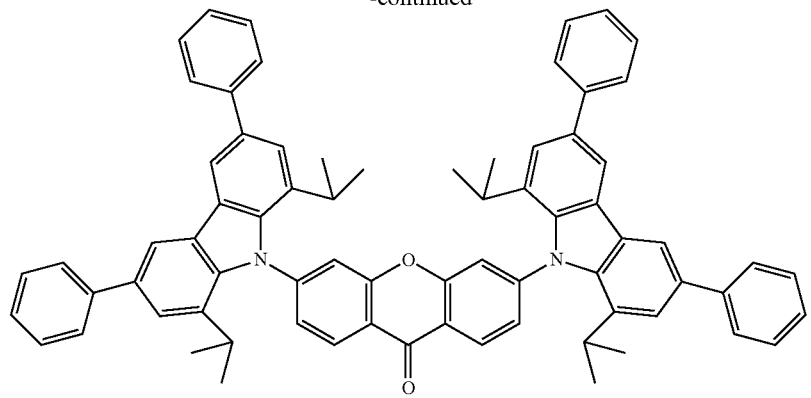

Compound 6

Synthesis Example 7

Synthesis of Compound 7

The synthesis was performed according to the following reaction scheme in the same manner as in the compound 1 in Example 1 (yield: 46%).

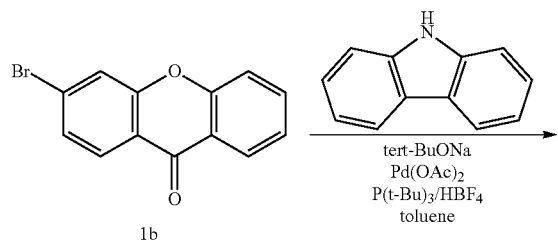

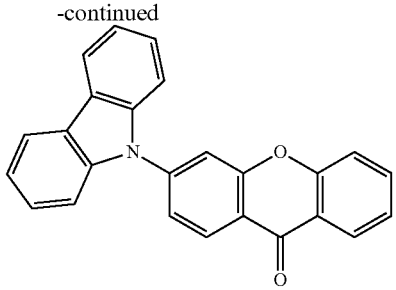

Compound 7

$^1$H-NMR (500 MHz, CDCl$_3$, δ): 7.36 (t, 2H), 7.42-7.51 (m, 3H) 7.54 (d, 1H), 7.61 (d, 2H), 7.67 (d, 1H), 7.75-7.81 (m, 2H), 8.17 (d, 2H), 8.41 (d, 1H), 8.58 (d, 1H)

ESI-MS (m/z) (M$^+$) calcd. 361.11, found 361.20.

Synthesis Example 8

Synthesis of Compound 9

The synthesis was performed according to the following reaction scheme in the same manner as in the compound 1 in Example 1 (yield: 99%).

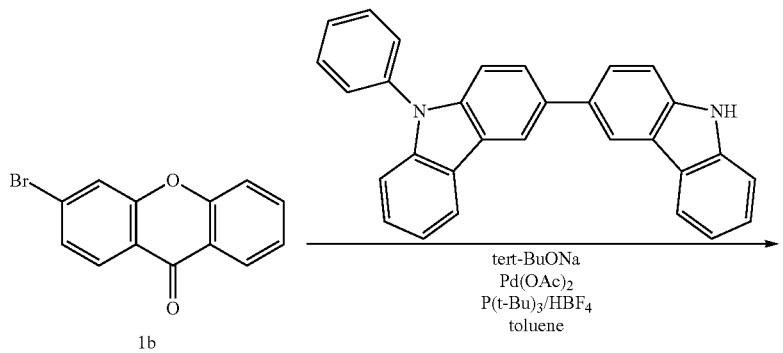

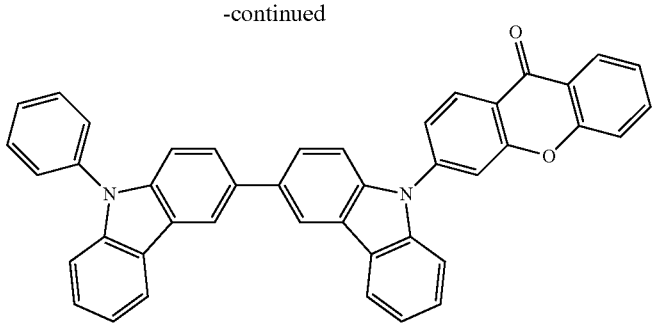

Compound 9

$^1$H-NMR (500 MHz, CDCl$_3$, δ): 7.33 (m, 1H), 7.38 (t, 1H), 7.41-7.58 (m, 7H), 7.60-7.68 (m, 5H), 7.72 (t, 2H), 7.75-7.86 (m, 4H), 8.26 (dd, 2H), 8.42 ((d, 1H), 8.47 (s, 2H), 8.61 (d, 1H)

ESI-MS (m/z) (M$^+$): calcd. 602.20, found 602.40.

Synthesis Example 9

Synthesis of Compound 10

The synthesis was performed according to the following reaction scheme in the same manner as in the compound 4 in Example 2 (yield: 63%)

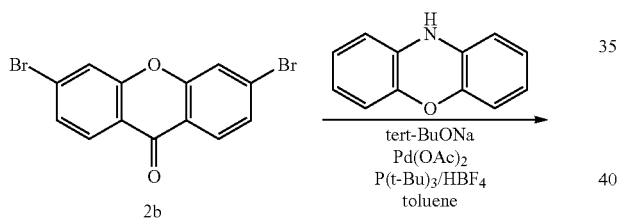

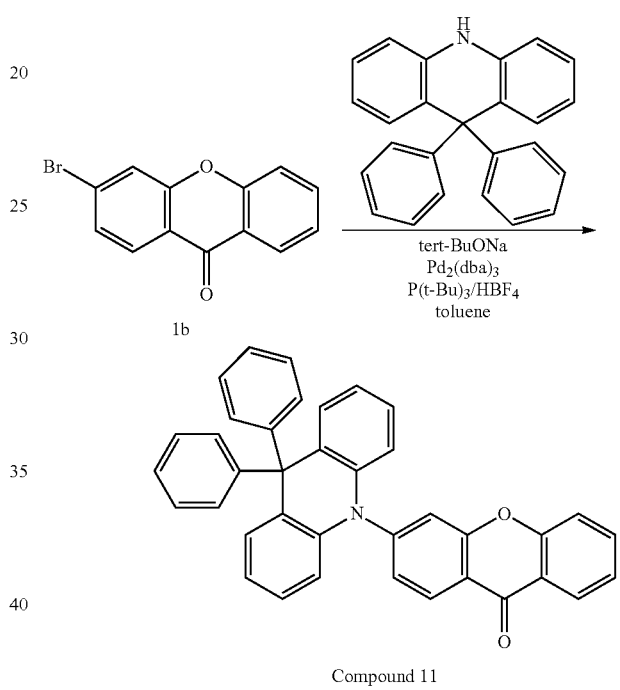

Compound 10

Synthesis Example 10

Synthesis of Compound 11

The synthesis was performed according to the following reaction scheme in the same manner as in the compound 1 in Example 1 (yield: 92%).

Compound 11

Example 1

Production of Organic Photoluminescent Device Using Compound 1 and Evaluation of Characteristics Thereof A toluene solution (concentration: 10$^{-5}$ mol/L) and a hexane solution (concentration: 10$^{-5}$ mol/L) of the compound 1 were prepared.

The compound 1 and mCBP were vapor-deposited from separate vapor deposition sources on a quartz substrate by a vacuum vapor deposition method under a condition of a vacuum degree of 10$^{-4}$ Pa or less, so as to form a vapor-co-deposited thin film having a thickness of 100 nm and a concentration of the compound 1 of 6.0% by weight.

Figure 2:
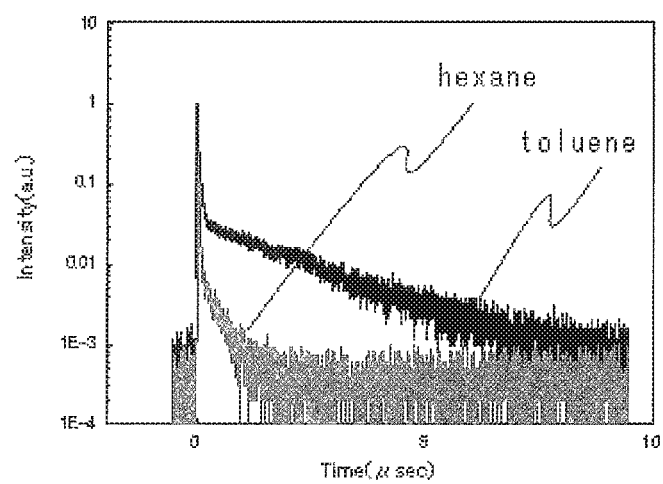
FIG. 2 is the transient decay curves of the toluene solution and the hexane solution of the compound 1 in Example 1.

FIG. 2 shows the transient decay curves of the toluene solution and the hexane solution of the compound 1. The toluene solution had a fluorescence decay time of τ1: 48 ns and τ2: 1,500 ns, and the hexane solution had a fluorescence decay time of τ1: 18 ns and τ2: 385 ns.

Figure 3:
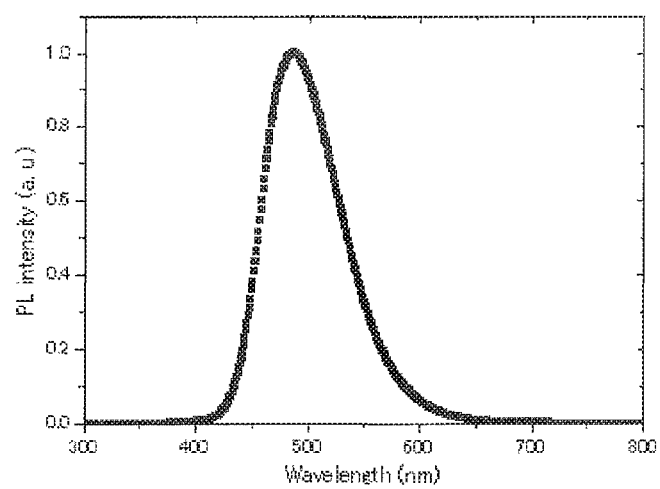
FIG. 3 is the light emission spectrum of the thin film organic photoluminescent device of the compound 1 in Example 1.

FIG. 3 shows the result of the measurement of the light emission spectrum of the vapor-co-deposited thin film of the compound 1 and mCBP by excitation light of 325 nm. The vapor-co-deposited thin film had a photoluminescence quantum efficiency of 89%.

Figure 4:
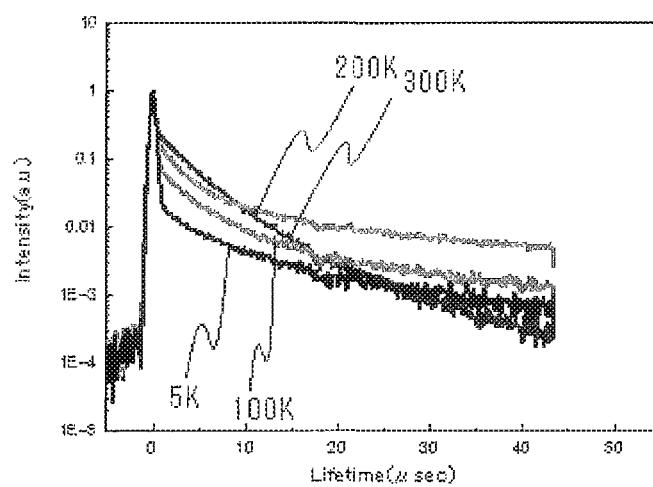
FIG. 4 is the transient decay curves of the thin film organic photoluminescent device of the compound 1 in Example 1.

FIG. 4 shows the transient decay curves of the vapor-co-deposited thin film at temperatures of 300 K, 200 K, 100 K and 5 K. FIG. 4 confirmed thermally activated delayed fluorescence, in which the delayed fluorescence component was increased according to the temperature rise.

Example 2

Production of Organic Photoluminescent Device Using Compound 2 and Evaluation of Characteristics Thereof Specimens were produced by changing the compound 1 to the compound 2. A toluene solution and a hexane solution were not produced, and in the production of the vapor-co-deposited thin film, mCP was used instead of mCBP.

Figure 5:
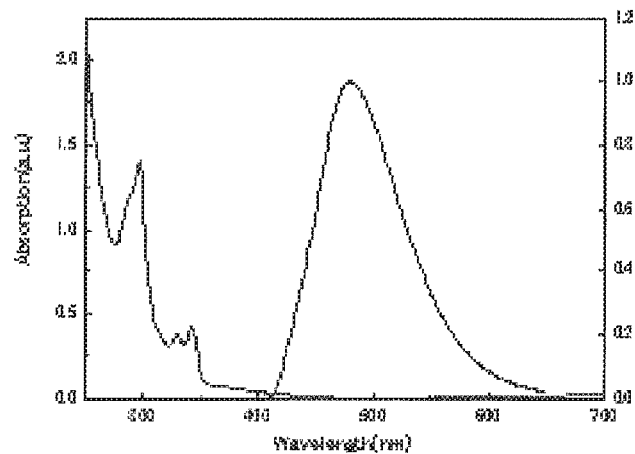
FIG. 5 is the light emission spectrum of the thin film organic photoluminescent device of the compound 2 in Example 2.

FIG. 5 shows the result of the measurement of the light emission spectrum of the vapor-co-deposited thin film of the compound 2 and mCP by excitation light of 345 nm. The vapor-co-deposited thin film had a photoluminescence quantum efficiency of 66%.

Figure 6:
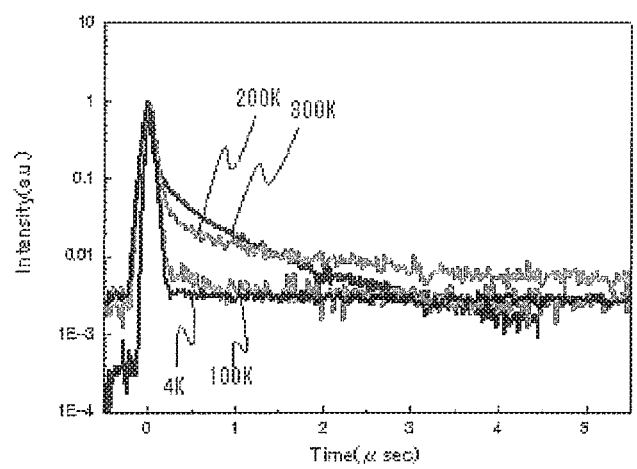
FIG. 6 is the transient decay curves of the thin film organic photoluminescent device of the compound 2 in Example 2.

FIG. 6 shows the transient decay curves of the vapor-co-deposited thin film at temperatures of 300 K, 200 K, 100 K and 5 K. FIG. 6 confirmed thermally activated delayed fluorescence, in which the delayed fluorescence component was increased according to the temperature rise.

Example 3

Production of Organic Photoluminescent Device Using Compound 3 and Evaluation of Characteristics Thereof Specimens were produced by changing the compound 1 to the compound 3. In the production of the vapor-co-deposited thin film, mCP was used instead of mCBP.

Figure 7:
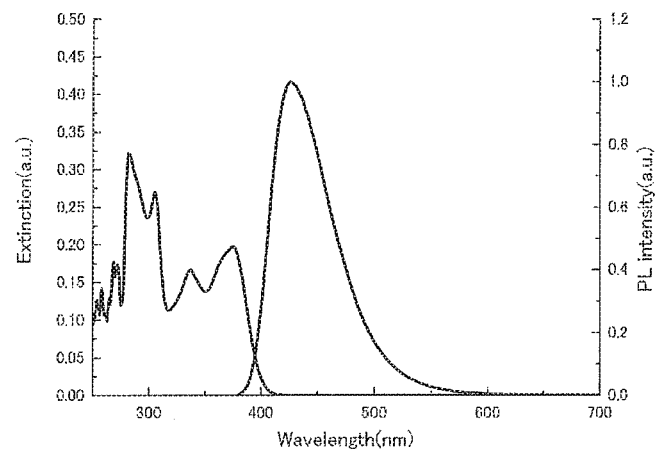
FIG. 7 is the light emission spectrum of the toluene solution of the compound 3 in Example 3.

FIG. 7 shows the result of the measurement of the light emission spectrum of the toluene solution of the compound 3 by excitation light of 370 nm. The photoluminescence quantum efficiency was 35% for the toluene solution with bubbling nitrogen.

Figure 8:
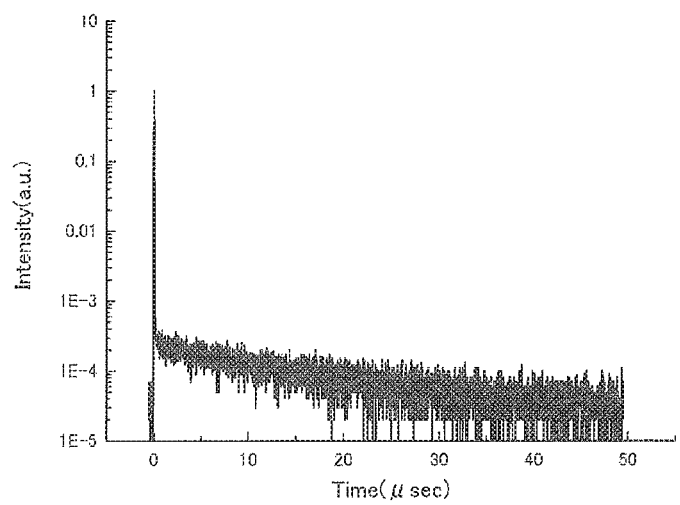
FIG. 8 is the transient decay curve of the toluene solution of the compound 3 in Example 3.

FIG. 8 shows the transient decay curve of the toluene solution. The toluene solution had a fluorescence decay time of $\tau 1$: 3.2 ns and $\tau 2$: 11 ns, which confirmed delayed fluorescence.

Figure 9:
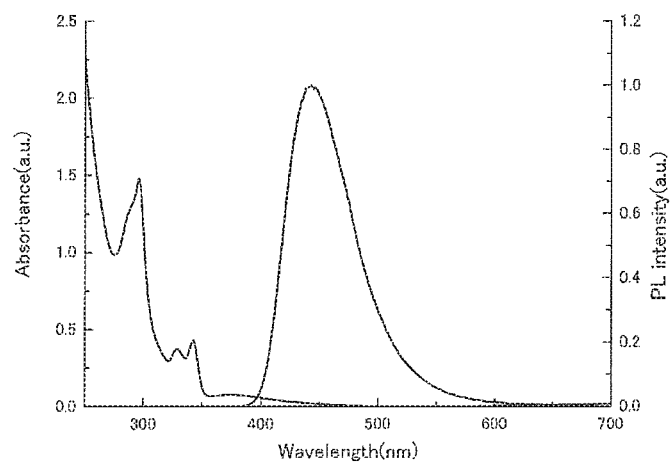
FIG. 9 is the light emission spectrum of the thin film organic photoluminescent device of the compound 3 in Example 3.

FIG. 9 shows the result of the measurement of the light emission spectrum of the vapor-co-deposited thin film of the compound 3 and mCP by excitation light of 300 nm. The vapor-co-deposited thin film had a photoluminescence quantum efficiency of 30%.

Figure 10:
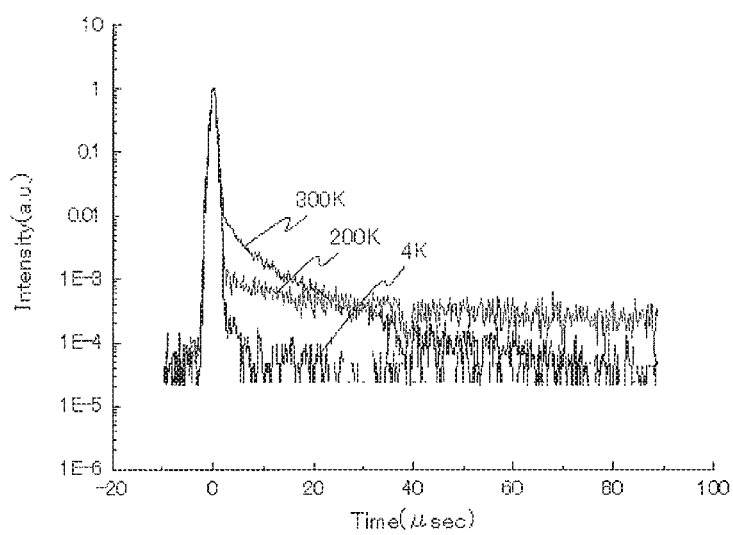
FIG. 10 is the transient decay curves of the thin film organic photoluminescent device of the compound 3 in Example 3.

FIG. 10 shows the transient decay curves of the vapor-co-deposited thin film at temperatures of 300 K, 200 K and 4 K. FIG. 10 confirmed thermally activated delayed fluorescence, in which the delayed fluorescence component was increased according to the temperature rise.

Example 4

Production of Organic Photoluminescent Device Using Compound 4 and Evaluation of Characteristics Thereof Specimens were produced by changing the compound 1 to the compound 4. In the production of the vapor-co-deposited thin film, mCP was used instead of mCBP.

Figure 12:
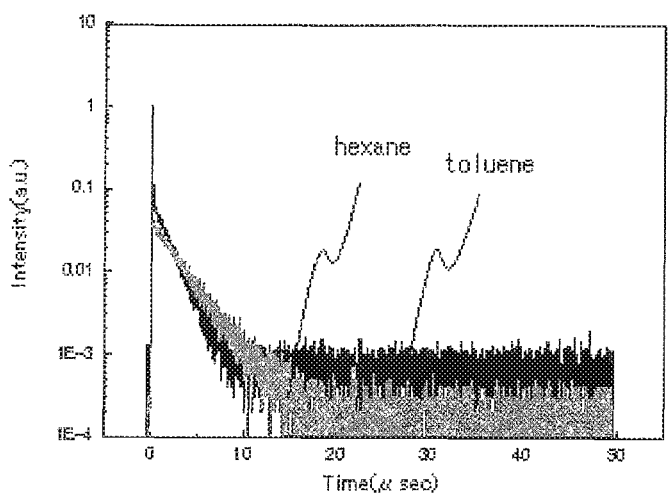
FIG. 12 is the transient decay curves of the toluene solution and the hexane solution of the compound 4 in Example 4.

FIG. 12 shows the transient decay curves of the toluene solution and the hexane solution of the compound 4. The toluene solution had a fluorescence decay time of $\tau 1$: 47 ns and $\tau 2$: 1.7 µs, and the hexane solution had a fluorescence decay time of $\tau 1$: 15 ns and $\tau 2$: 2.5 µs.

Figure 11:
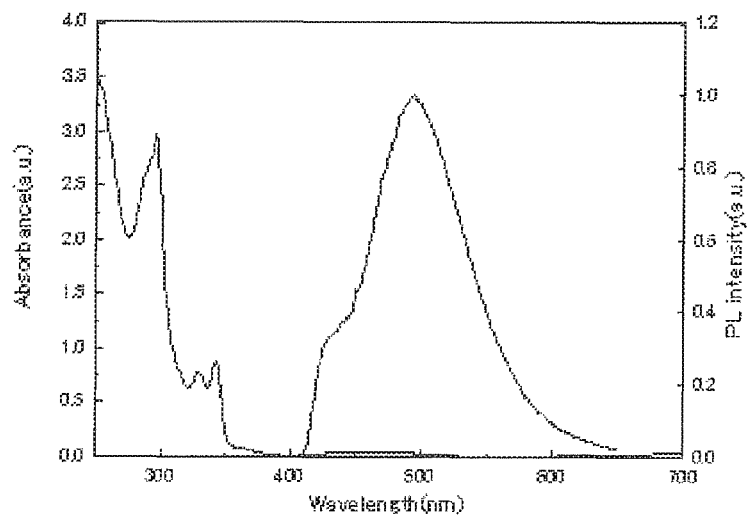
FIG. 11 is the light emission spectrum of the thin film organic photoluminescent device of the compound 4 in Example 4.

FIG. 11 shows the result of the measurement of the light emission spectrum of the vapor-co-deposited thin film of the compound 4 and mCP by excitation light of 325 nm. The vapor-co-deposited thin film had a photoluminescence quantum efficiency of 89%.

Figure 13:
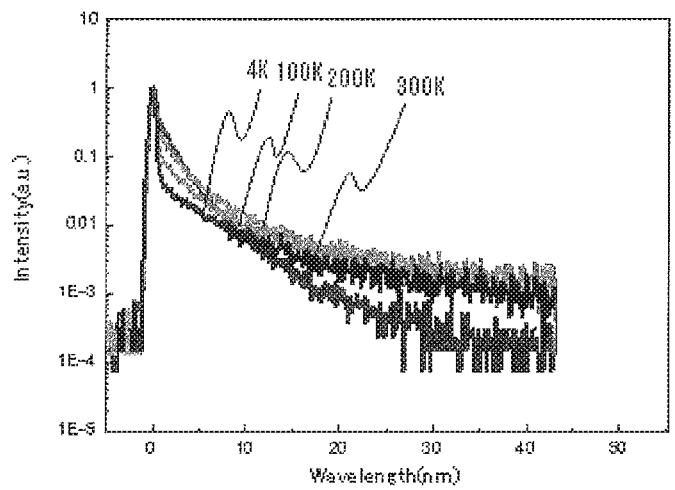
FIG. 13 is the transient decay curves of the thin film organic photoluminescent device of the compound 4 in Example 4.

FIG. 13 shows the transient decay curves of the vapor-co-deposited thin film at temperatures of 300 K, 200 K, 100 K and 4 K. FIG. 13 confirmed thermally activated delayed fluorescence, in which the delayed fluorescence component was increased according to the temperature rise.

Example 5

Production of Organic Photoluminescent Device Using Compound and Evaluation of Characteristics Thereof A toluene solution was prepared by changing the compound 1 to the compound 5.

Figure 14:
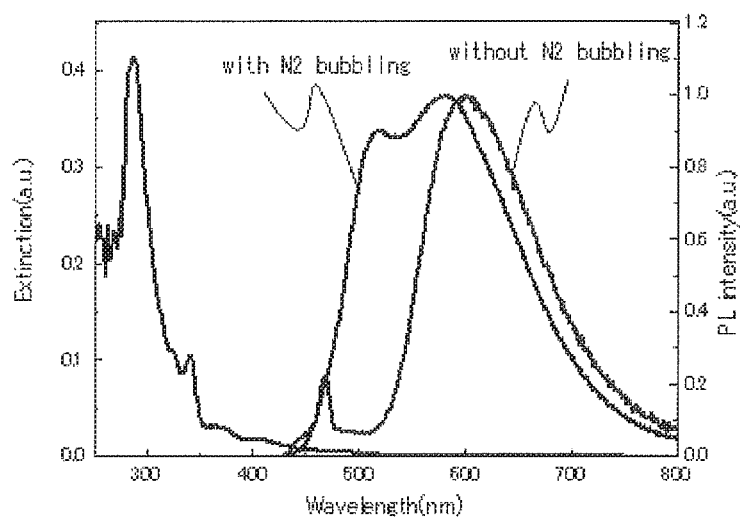
FIG. 14 is the light emission spectra of the toluene solution of the compound 5 in Example 5.

FIG. 14 shows the result of the measurement of the light emission spectrum of the toluene solution of the compound 5 by excitation light of 380 nm. The toluene solution had a photoluminescence quantum efficiency of 0.6% without bubbling nitrogen and 25% with bubbling nitrogen.

Figure 15:
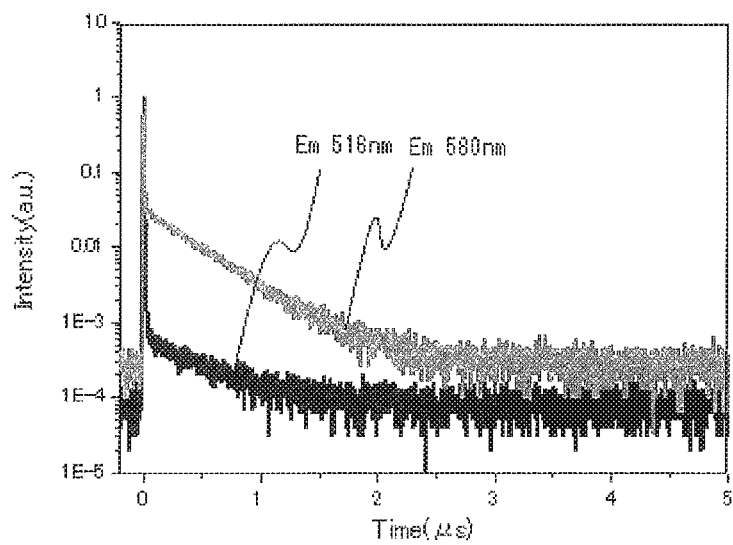
FIG. 15 is the transient decay curves of the toluene solution of the compound 5 in Example 5.

FIG. 15 shows the transient decay curves of the toluene solution of the compound 5. The toluene solution had a fluorescence decay time of $\tau 1$: 3.9 ns and $\tau 2$: 419 ns for fluorescent light of 516 nm and $\tau 1$: 4.1 ns and $\tau 2$: 415 ns for fluorescent light of 580 nm, and delayed fluorescence was confirmed.

Example 6

Production of Organic Photoluminescent Device Using Compound 6 and Evaluation of Characteristics Thereof A toluene solution was prepared by changing the compound 1 to the compound 6.

Figure 16:
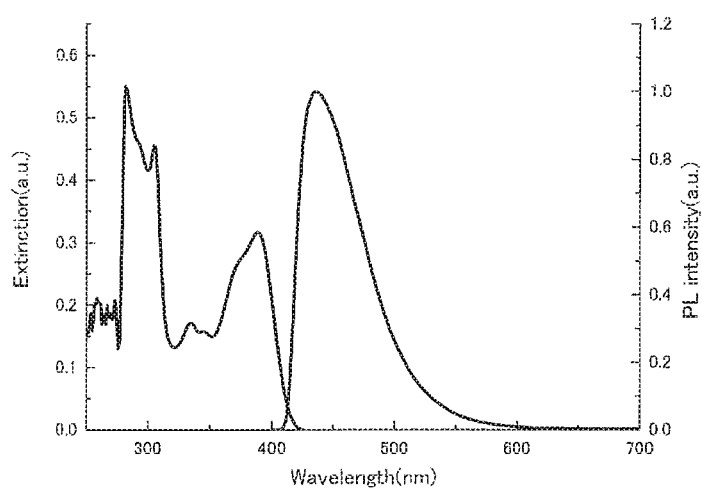
FIG. 16 is the light emission spectrum of the toluene solution of the compound 6 in Example 6.

FIG. 16 shows the result of the measurement of the light emission spectrum of the toluene solution of the compound 6 by excitation light of 370 nm. The toluene solution had a photoluminescence quantum efficiency of 32% with bubbling nitrogen.

Figure 17:
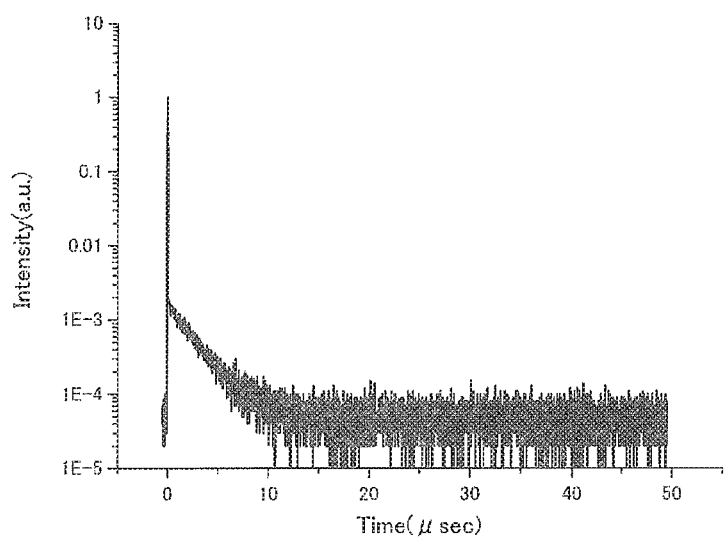
FIG. 17 is the transient decay curve of the toluene solution of the compound 6 in Example 6.

FIG. 17 shows the transient decay curve of the toluene solution of the compound 6. The toluene solution had a fluorescence decay time of $\tau 1$: 2.2 ns and $\tau 2$: 2.4 µs, and delayed fluorescence was confirmed.

Figure 18:
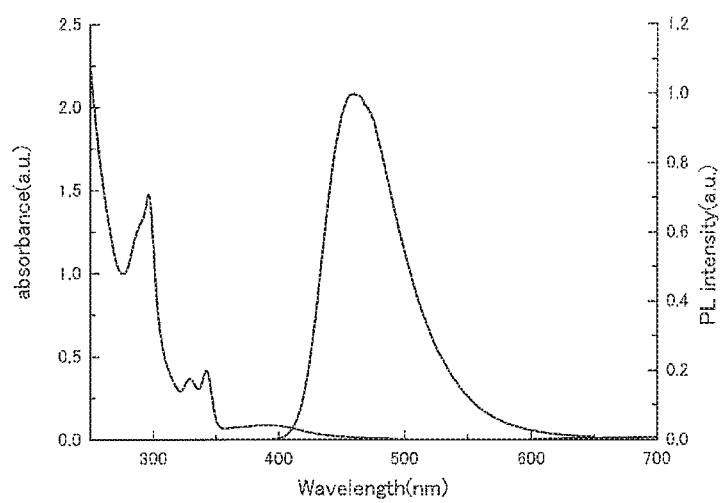
FIG. 18 is the light emission spectrum of the thin film organic photoluminescent device of the compound 6 in Example 6.

FIG. 18 shows the result of the measurement of the light emission spectrum of the vapor-co-deposited thin film of the compound 6 and mCP by excitation light of 370 nm. The vapor-co-deposited thin film had a photoluminescence quantum efficiency of 60%.

Figure 19:
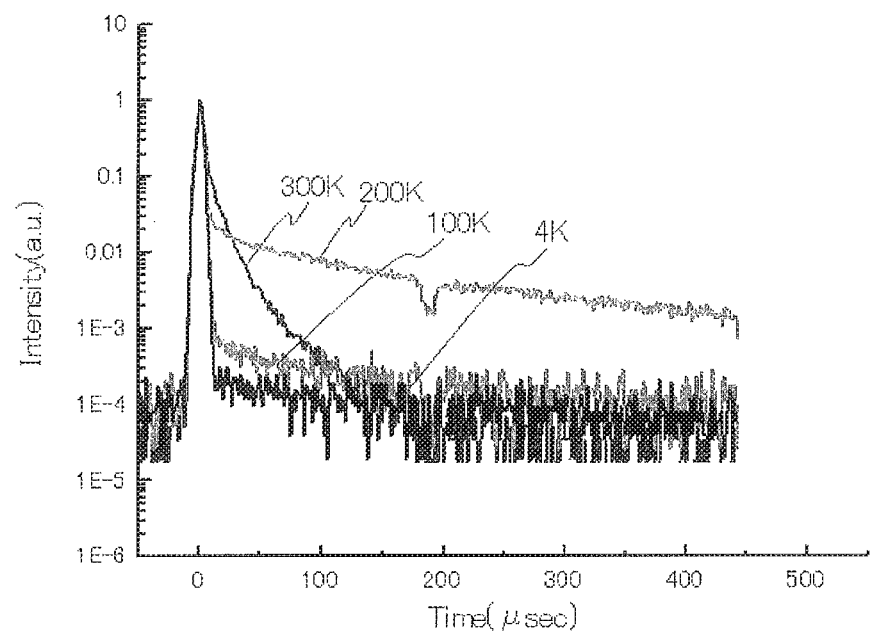
FIG. 19 is the transient decay curves of the thin film organic photoluminescent device of the compound 6 in Example 6.

FIG. 19 shows the transient decay curves of the vapor-co-deposited thin film at temperatures of 300 K, 200 K, 100 K and 4 K. FIG. 19 confirmed thermally activated delayed fluorescence, in which the delayed fluorescence component was increased according to the temperature rise.

Example 7

Production of Organic Photoluminescent Device Using Compound 9 and Evaluation of Characteristics Thereof A toluene solution was prepared by changing the compound 1 to the compound 9.

Figure 20:
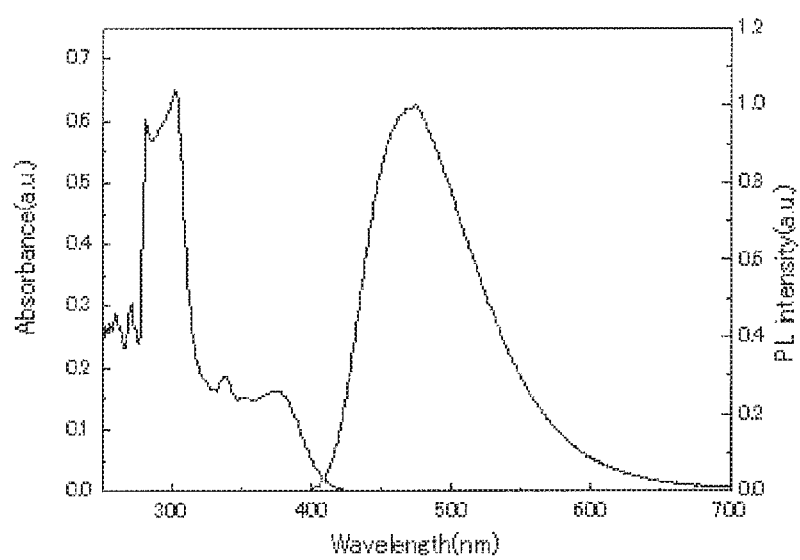
FIG. 20 is the light emission spectrum of the thin film organic photoluminescent device of the compound 9 in Example 7.
Figure 21:
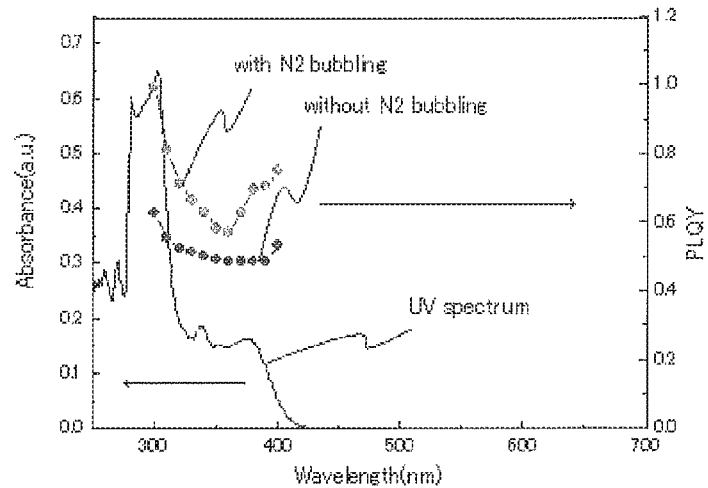
FIG. 21 is a graph of the photoluminescence quantum efficiency of the compound 9 in Example 7 plotted against the wavelength.

FIG. 20 shows the result of the measurement of the light emission spectrum of the toluene solution of the compound 9 by excitation light of 375 nm, and FIG. 21 shows the photoluminescence quantum efficiency thereof plotted against the wavelength. As shown in FIG. 21, the photoluminescence quantum efficiency was a lower value for the toluene solution without bubbling nitrogen than the toluene solution with bubbling nitrogen. It is expected that this is because the compound 9 is a fluorescent substance showing delayed fluorescence, and in the toluene solution of the compound 9 without bubbling nitrogen, oxygen inhibits the reverse intersystem crossing of the exciton in the excited triplet state to the excited singlet state.

Example 8

Production of Organic Photoluminescent Device Using Compound and Evaluation of Characteristics Thereof A toluene solution was prepared by changing the compound 1 to the compound 10.

Figure 22:
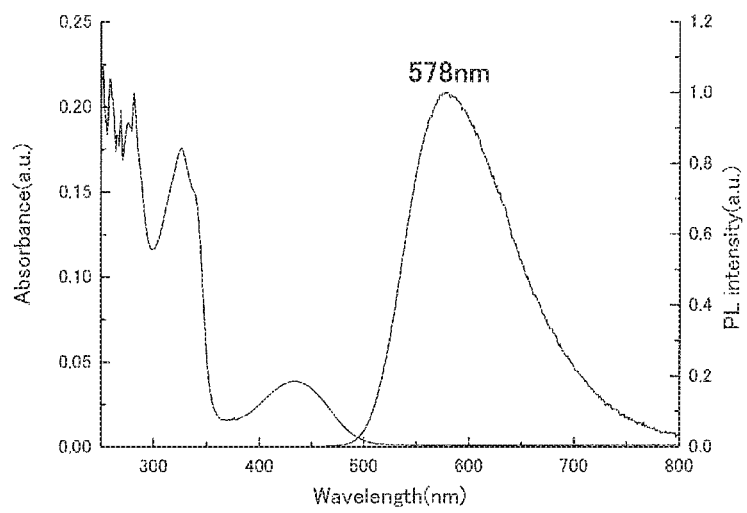
FIG. 22 is the light emission spectrum of the toluene solution of the compound 10 in Example 8.

FIG. 22 shows the result of the measurement of the light emission spectrum of the toluene solution of the compound 10 by excitation light of 420 nm. The toluene solution had a photoluminescence quantum efficiency of 44% with bubbling nitrogen.

Figure 23:
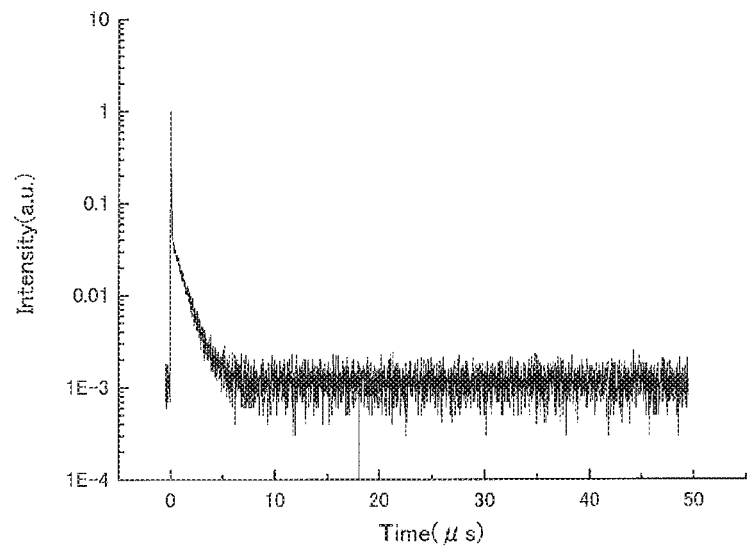
FIG. 23 is the transient decay curve of the toluene solution of the compound 10 in Example 8.

FIG. 23 shows the transient decay curve of the toluene solution of the compound 10. The toluene solution had a fluorescence decay time of $\tau 1$: 32 ns and $\tau 2$: 1.1 μs, and delayed fluorescence was confirmed.

Example 9

Production of Organic Photoluminescent Device Using Compound 11 and Evaluation of Characteristics Thereof A toluene solution was prepared by changing the compound 1 to the compound 11.

Figure 24:
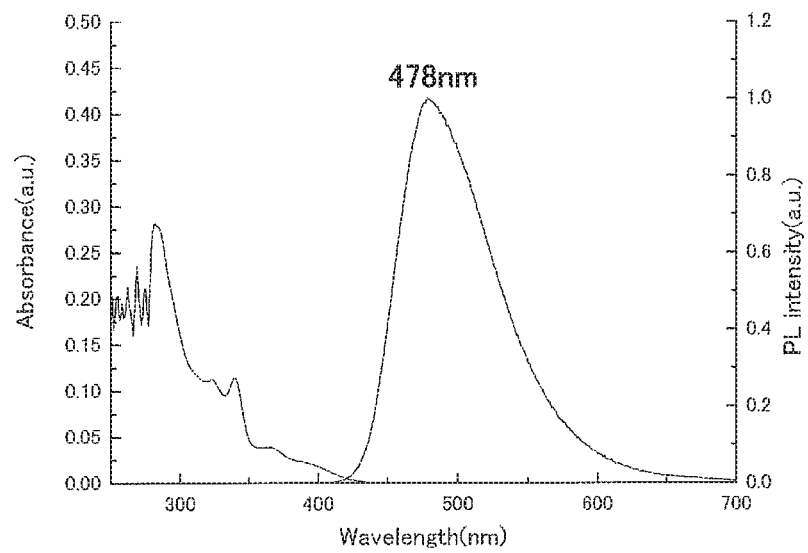
FIG. 24 is the light emission spectrum of the toluene solution of the compound 11 in Example 9.

FIG. 24 shows the result of the measurement of the light emission spectrum of the toluene solution of the compound 11 by excitation light of 400 nm. The toluene solution had a photoluminescence quantum efficiency of 97% with bubbling nitrogen.

Figure 25:
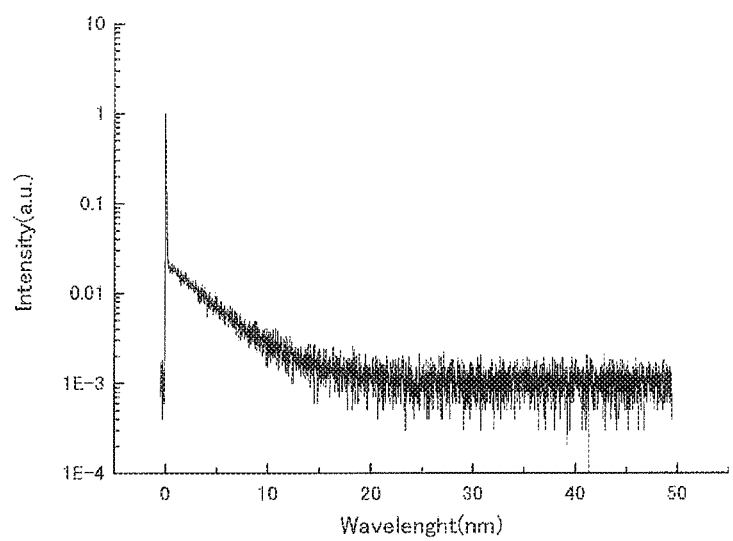
FIG. 25 is the transient decay curve of the toluene solution of the compound 11 in Example 9.

FIG. 25 shows the transient decay curve of the toluene solution of the compound 11. The toluene solution had a fluorescence decay time of $\tau 1$: 37 ns and $\tau 2$: 3.8 s, and delayed fluorescence was confirmed.

Example 10

Production of Organic Electroluminescent Devices Using Compound 1 and Compound 4 and Evaluation of Characteristics Thereof Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, α-NPD was formed to a thickness of 40 nm on ITO. Subsequently, the compound 1 and mCP were co-deposited thereon from separate vapor deposition sources to form a layer having a thickness of 20 nm, which was designated as a light emitting layer. At this time, the concentration of the compound 1 was 6.0% by weight. TPBi was then formed to a thickness of 40 nm, then lithium fluoride (LiF) was vacuum vapor-deposited to a thickness of 0.8 nm, and then aluminum (Al) was vapor-deposited to a thickness of 80 nm to form a cathode, thereby producing an organic electroluminescent device.

An organic electroluminescent device was produced in the same manner except that the compound 4 was used instead of the compound 1.

Figure 26:
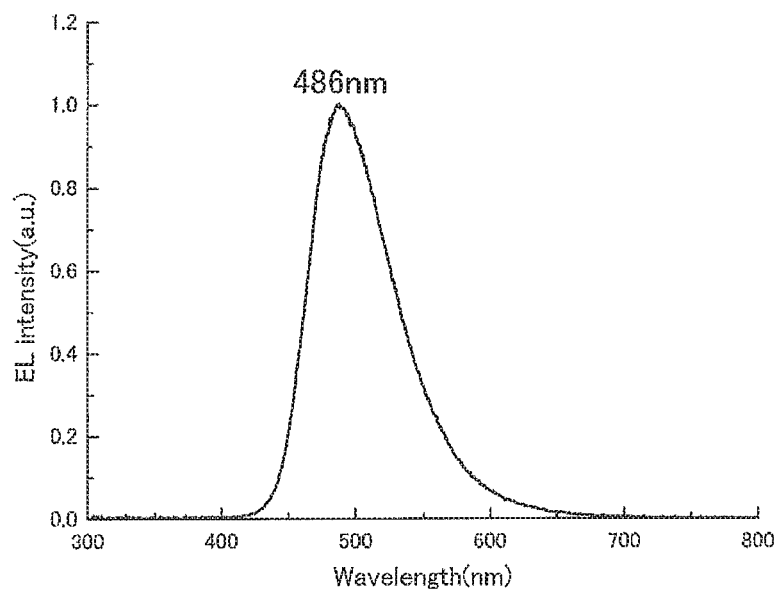
FIG. 26 is the light emission spectrum of the organic electroluminescent device of the compound 1 in Example 10.
Figure 27:
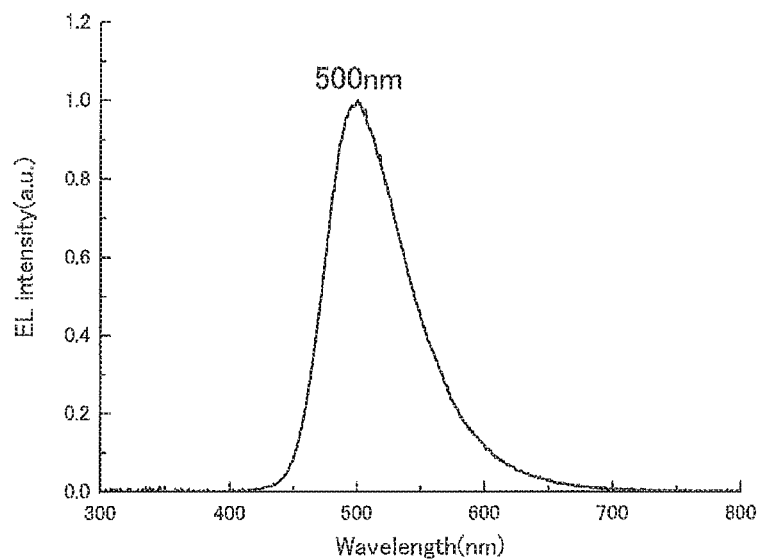
FIG. 27 is the light emission spectrum of the organic electroluminescent device of the compound 4 in Example 10.
Figure 28:
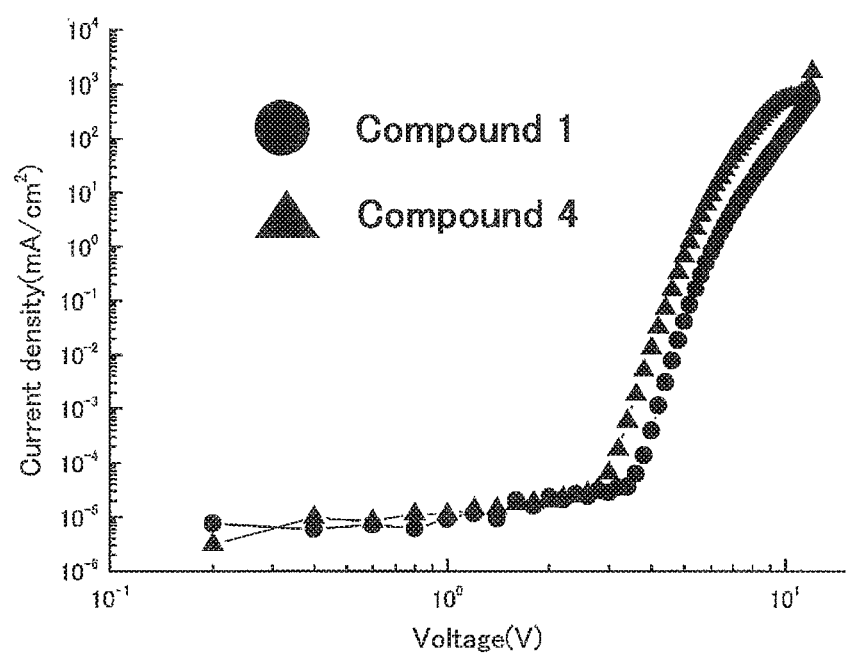
FIG. 28 is a graph showing the voltage-electric current density characteristics of the organic electroluminescent devices of the compound 1 and the compound 4 in Example 10.
Figure 29:
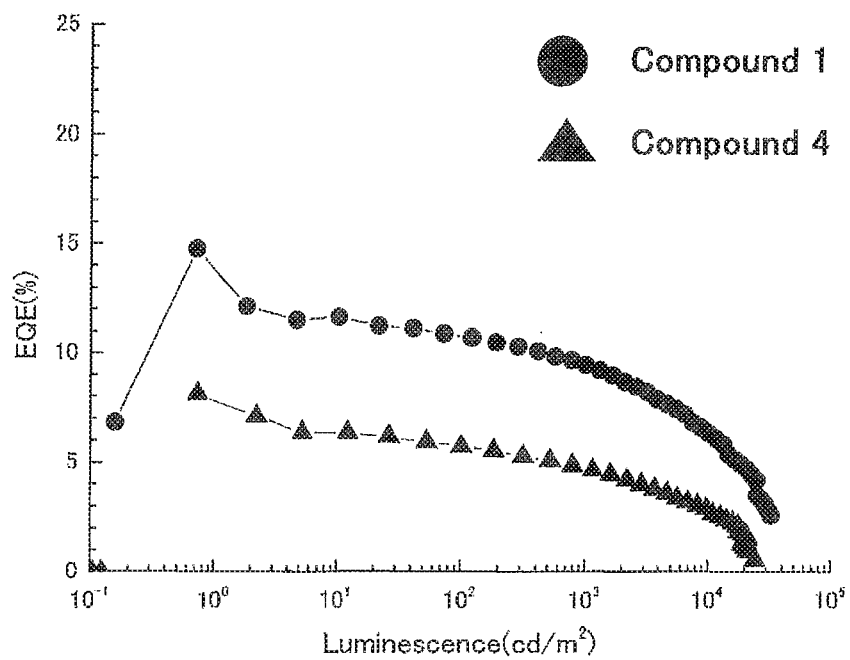
FIG. 29 is a graph showing the light emission intensity-external quantum efficiency characteristics of the organic electroluminescent devices of the compound 1 and the compound 4 in Example 10.
Figure 30:
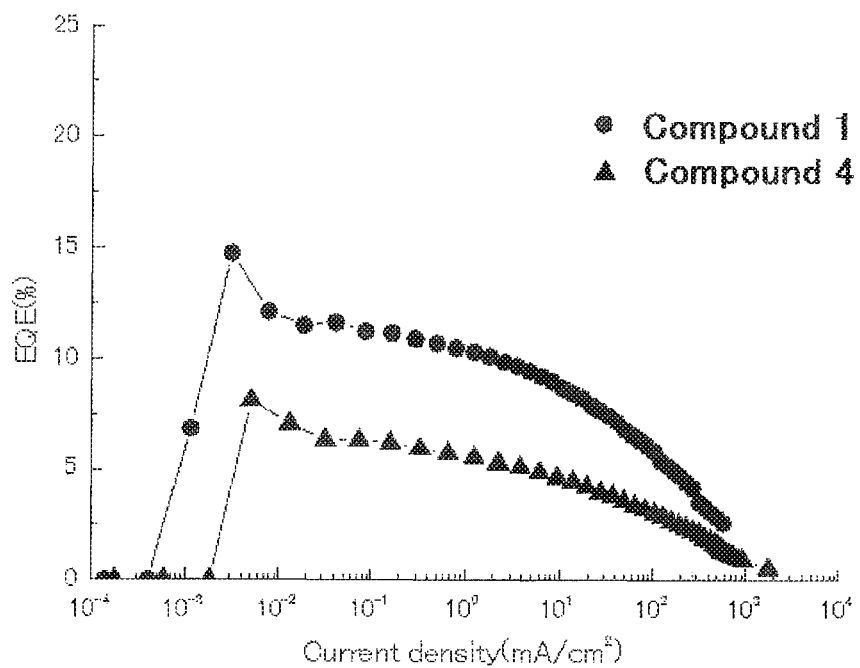
FIG. 30 is a graph showing the electric current density-external quantum efficiency characteristics of the organic electroluminescent devices of the compound 1 and the compound 4 in Example 10.

FIG. 26 shows the light emission spectrum of the organic electroluminescent device produced by using the compound 1, and FIG. 27 shows the light emission spectrum of the organic electroluminescent device produced by using the compound 4. FIG. 28 shows the voltage-electric current density characteristics of the two organic electroluminescent devices thus produced, FIG. 29 shows the light emission intensity-external quantum efficiency characteristics thereof, and FIG. 30 shows a graph showing the electric current density-external quantum efficiency characteristics thereof. Both the organic electroluminescent devices each achieved a high external quantum efficiency that exceeded an external quantum efficiency in the case where an ordinary fluorescent material showing no delayed fluorescence was used as a light emitting material. In particular, the organic electroluminescent device using the compound 1 achieved a considerably high external quantum efficiency.

The similar high external quantum efficiency was achieved also in the case where CzDBF was used instead of mCP, and PPT was used instead of TPBi.

Example 11

Production of Organic Electroluminescent Devices Using Compound 1 and Evaluation of Characteristics Thereof Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, HAT-CN was formed to a thickness of 10 nm on ITO, and thereon Tris-PCz was formed to a thickness of 30 nm. Subsequently, the compound 1 and mCBP were co-deposited thereon from separate vapor deposition sources to form a layer having a thickness of 30 nm, which was designated as a light emitting layer. At this time, the concentration of the compound 1 was 10% by weight or 20% by weight. Instead of the vapor co-deposition, furthermore, only the compound 1 was used as a vapor deposition source and formed to a thickness of 30 nm, which was designated as a light emitting layer having a concentration of the compound 1 of 100% by weight. T2T was then formed to a thickness of 10 nm, and thereon Bpy-TP2 was formed to a thickness of 40 nm. Subsequently, lithium fluoride (LiF) was vacuum vapor-deposited to a thickness of 0.8 nm, and then aluminum (Al) was vapor-deposited to a thickness of 100 nm to form a cathode. According to the procedures, three organic electroluminescent devices having different concentrations of the compound 1 in the light emitting layer.

Figure 31:
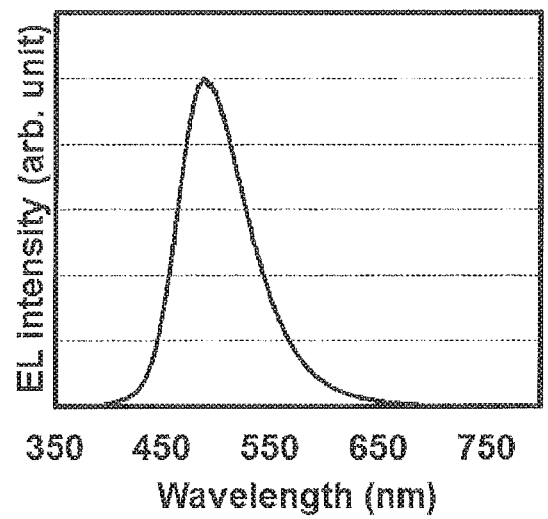
FIG. 31 is the light emission spectrum of the organic electroluminescent device of the compound 1 in a concentration of 10% by weight in Example 11.
Figure 32:
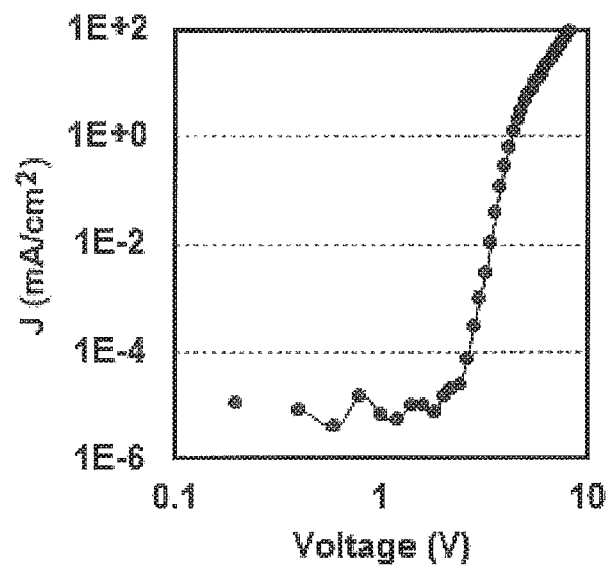
FIG. 32 is a graph showing the voltage-electric current density characteristics of the organic electroluminescent device of the compound 1 in a concentration of 10% by weight in Example 11.
Figure 33:
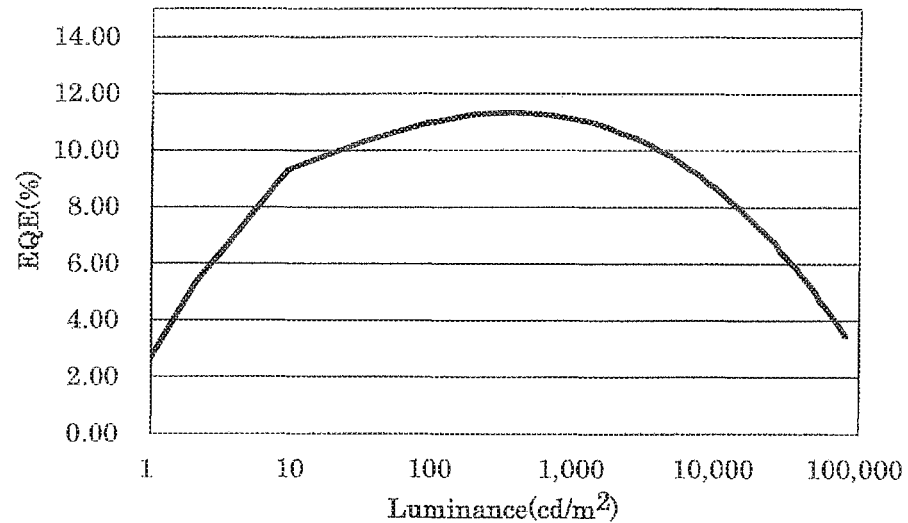
FIG. 33 is a graph showing the light emission intensity-external quantum efficiency characteristics of the organic electroluminescent device of the compound 1 in a concentration of 10% by weight in Example 11.
Figure 34:
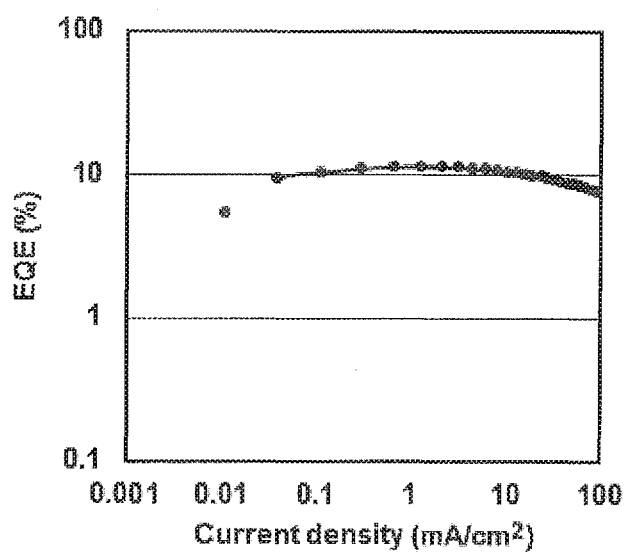
FIG. 34 is a graph showing the electric current density-external quantum efficiency characteristics of the organic electroluminescent device of the compound 1 in a concentration of 10% by weight in Example 11.
Figure 35:
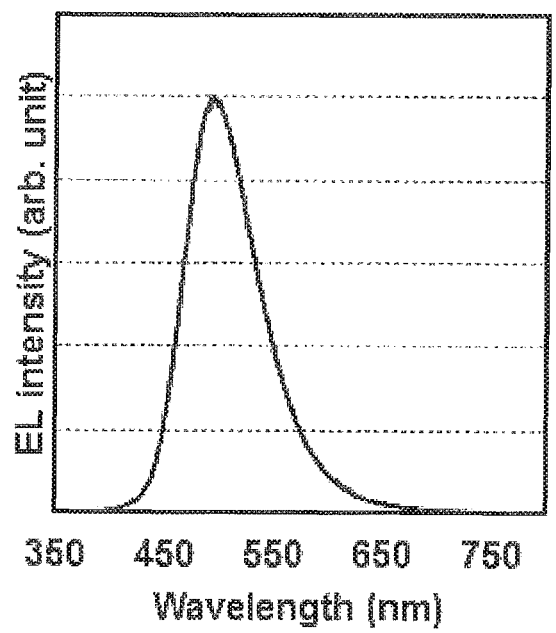
FIG. 35 is the light emission spectrum of the organic electroluminescent device of the compound 1 in a concentration of 20% by weight in Example 11.
Figure 36:
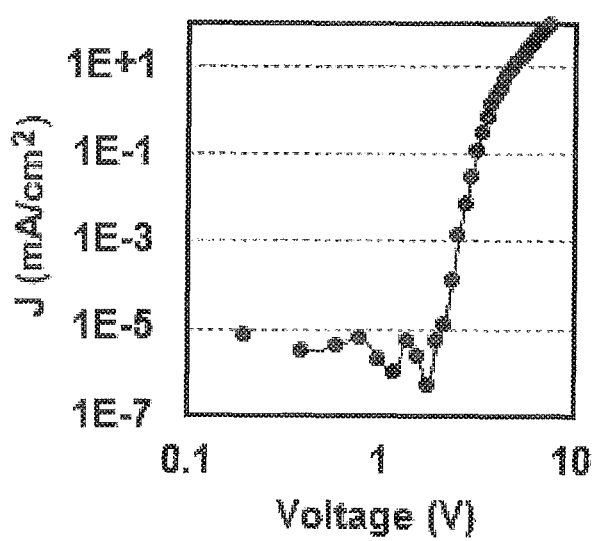
FIG. 36 is a graph showing the voltage-electric current density characteristics of the organic electroluminescent device of the compound 1 in a concentration of 20% by weight in Example 11.
Figure 37:
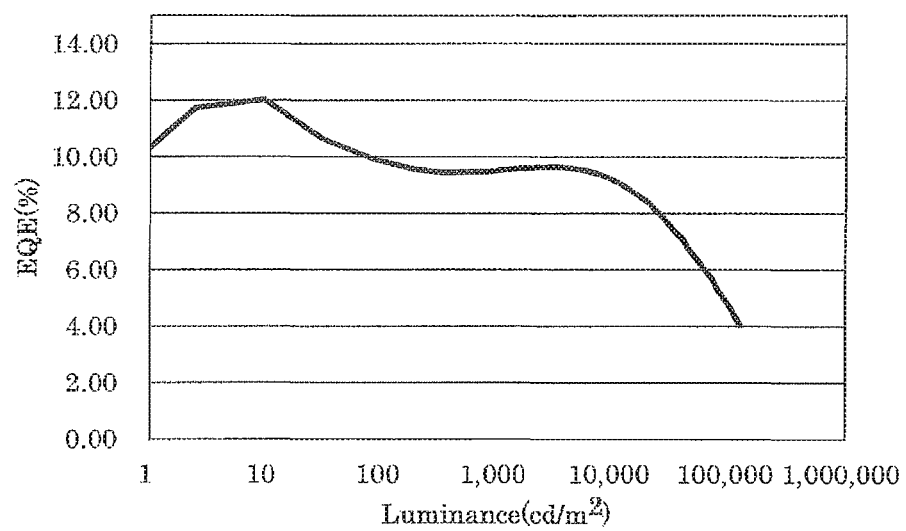
FIG. 37 is a graph showing the light emission intensity-external quantum efficiency characteristics of the organic electroluminescent device of the compound 1 in a concentration of 20% by weight in Example 11.
Figure 38:
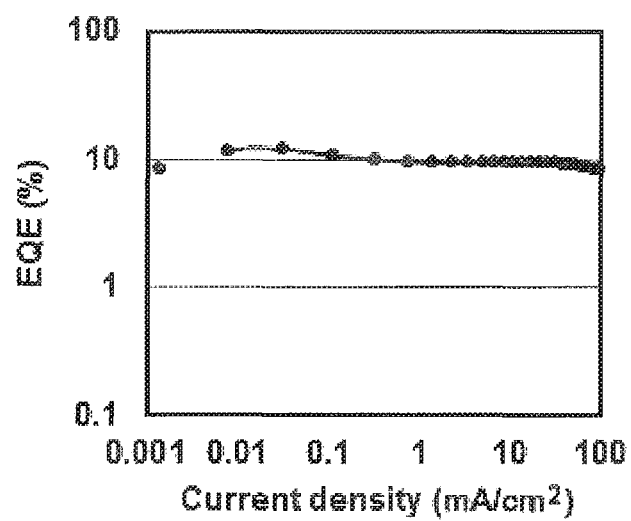
FIG. 38 is a graph showing the electric current density-external quantum efficiency characteristics of the organic electroluminescent device of the compound 1 in a concentration of 20% by weight in Example 11.
Figure 39:
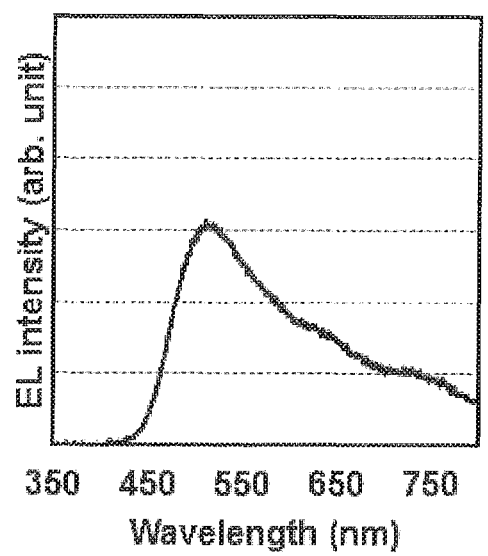
FIG. 39 is the light emission spectrum of the organic electroluminescent device of the compound 1 in a concentration of 100% by weight in Example 11.
Figure 40:
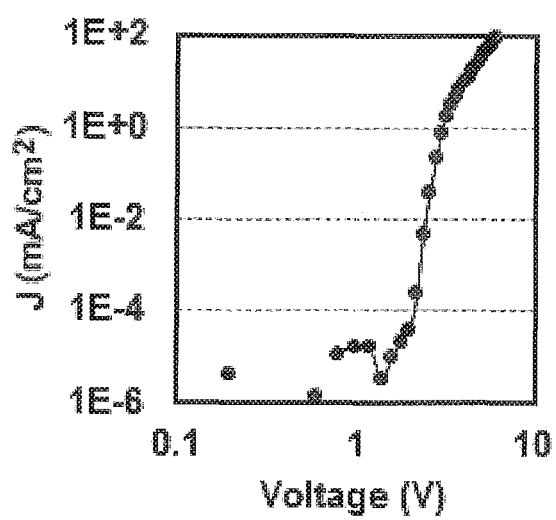
FIG. 40 is a graph showing the voltage-electric current density characteristics of the organic electroluminescent device of the compound 1 in a concentration of 100% by weight in Example 11.
Figure 41:
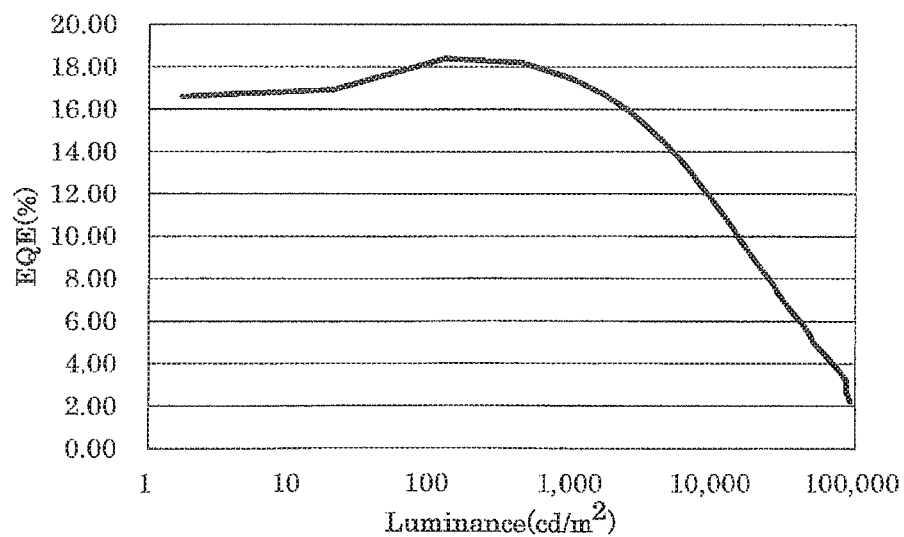
FIG. 41 is a graph showing the light emission intensity-external quantum efficiency characteristics of the organic electroluminescent device of the compound 1 in a concentration of 100% by weight in Example 11.
Figure 42:
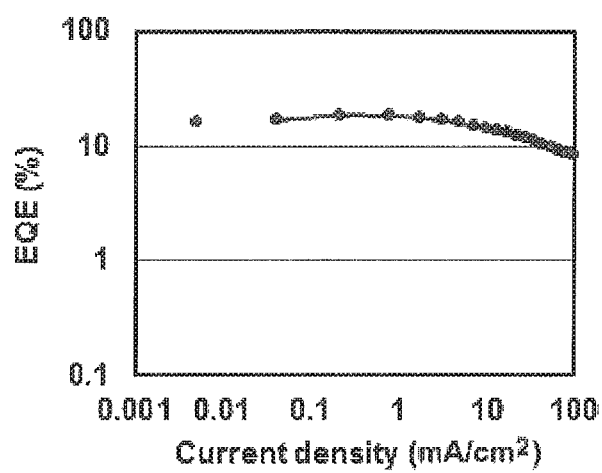
FIG. 42 is a graph showing the electric current density-external quantum efficiency characteristics of the organic electroluminescent device of the compound 1 in a concentration of 100% by weight in Example 11.

FIG. 31 shows the light emission spectrum of the organic electroluminescent device having a concentration of the compound 1 of 10% by weight, FIG. 32 shows the voltage-electric current density characteristics thereof, FIG. 33 shows the light emission intensity-external quantum efficiency characteristics thereof, and FIG. 34 shows the electric current density-external quantum efficiency characteristics thereof. FIG. 35 shows the light emission spectrum of the organic electroluminescent device having a concentration of the compound 1 of 20% by weight, FIG. 36 shows the voltage-electric current density characteristics thereof, FIG. 37 shows the light emission intensity-external quantum efficiency characteristics thereof, and FIG. 38 shows the electric current density-external quantum efficiency characteristics thereof. FIG. 39 shows the light emission spectrum of the organic electroluminescent device having a concentration of the compound 1 of 100% by weight, FIG. 40 shows the voltage-electric current density characteristics thereof, FIG. 41 shows the light emission intensity-external quantum efficiency characteristics thereof, and FIG. 42 shows the electric current density-external quantum efficiency characteristics thereof. Table 1 below shows the device characteristics of the organic electroluminescent devices. All the organic electroluminescent devices each achieved a high external quantum efficiency that exceeded an external quantum efficiency in the case where an ordinary fluorescent material showing no delayed fluorescence was used as a light emitting material.

Example 12

Production of Organic Electroluminescent Device Using Compound 4 and Evaluation of Characteristics Thereof Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, HAT-CN was formed to a thickness of 10 nm on ITO, thereon Tris-PCz was formed to a thickness of 20 nm, and thereon CCP was formed to a thickness of 10 nm. Subsequently, the compound 4 and CO(mQPh)2 were co-deposited thereon from separate vapor deposition sources to form a layer having a thickness of 30 nm, which was designated as a light emitting layer. At this time, the concentration of the compound 4 was 20% by weight. CO(mQPh)2 was then formed to a thickness of 10 nm, and thereon Bpy-TP2 was formed to a thickness of 20 nm. Subsequently, lithium fluoride (LiF) was vacuum vapor-deposited to a thickness of 0.8 nm, and then aluminum (Al) was vapor-deposited to a thickness of 100 nm to form a cathode, thereby producing an organic electroluminescent device.

Figure 43:
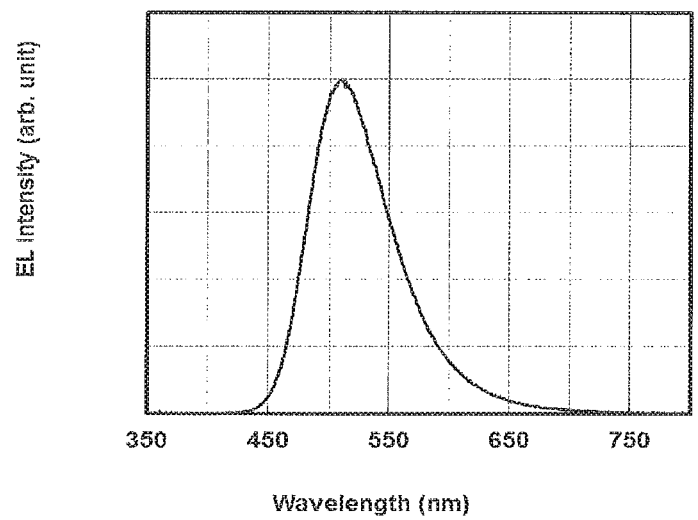
FIG. 43 is the light emission spectrum of the organic electroluminescent device of the compound 4 in Example 12.
Figure 44:
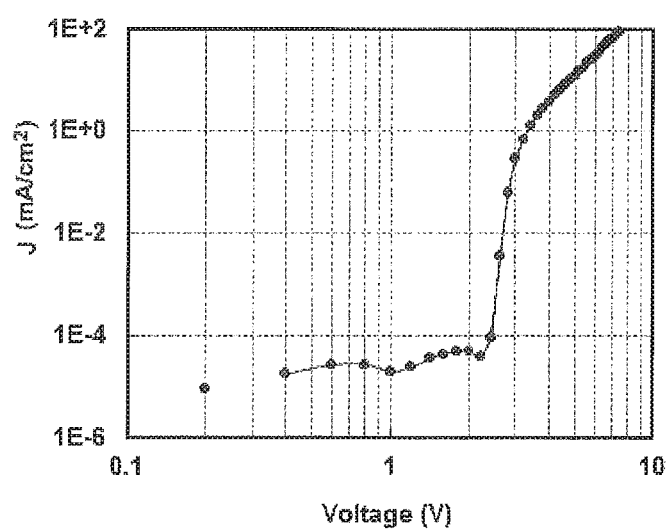
FIG. 44 is a graph showing the voltage-electric current density characteristics of the organic electroluminescent device of the compound 4 in Example 12.
Figure 45:
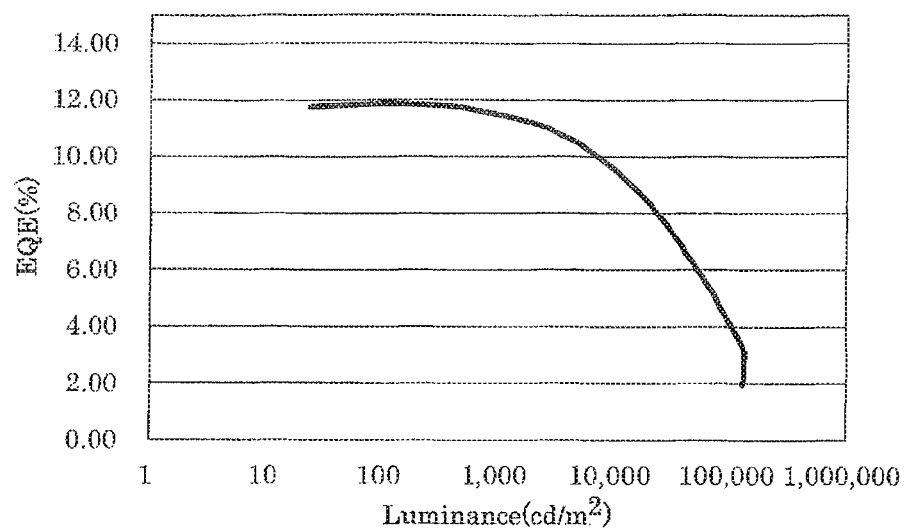
FIG. 45 is a graph showing the light emission intensity-external quantum efficiency characteristics of the organic electroluminescent device of the compound 4 in Example 12.
Figure 46:
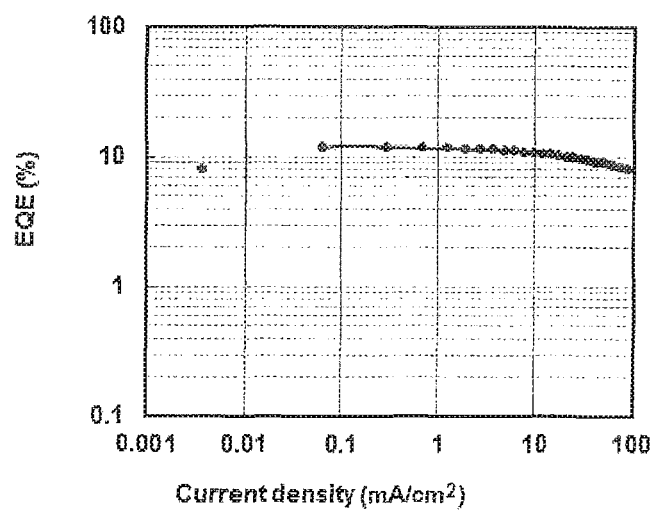
FIG. 46 is a graph showing the electric current density-external quantum efficiency characteristics of the organic electroluminescent device of the compound 4 in Example 12.

FIG. 43 shows the light emission spectrum of the organic electroluminescent device thus produced, FIG. 44 shows the voltage-electric current density characteristics thereof, FIG. 45 shows the light emission intensity-external quantum efficiency characteristics thereof, and FIG. 46 shows the electric current density-external quantum efficiency characteristics thereof. Table 1 below shows the device characteristics of the organic electroluminescent device thus produced. The organic electroluminescent device achieved a high external quantum efficiency that exceeded an external quantum efficiency in the case where an ordinary fluorescent material showing no delayed fluorescence was used as a light emitting material.

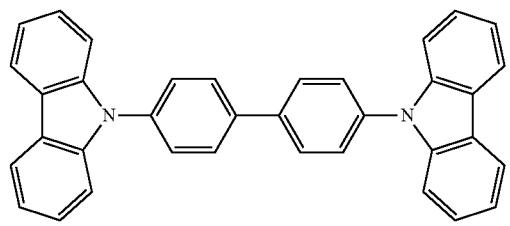

CBP

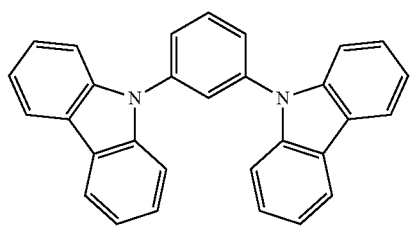

mCP

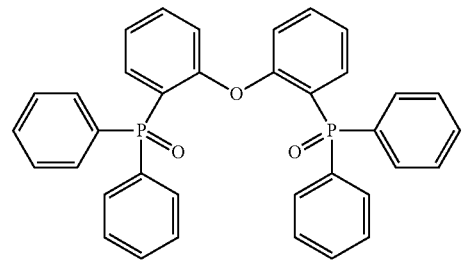

DPEPO

TABLE 1

|  | Compound (concentration) | External quantum efficiency EQE (%) | Electric current density J (mA/cm$^2$) | Driving voltage V (V) | Light emission efficiency (lm/W) | CIE (x, y) | Light emission peak (nm) |
|---|---|---|---|---|---|---|---|
|  |  | 1,000 cd/m$^2$ | | | | | |
| Example 11 | Compound 1 (10% by weight) | 11.1 | 3.68 | 4.87 | 17.55 | 0.1848, 0.4241 | 493.8 |
|  | Compound 1 (20% by weight) | 9.53 | 4.04 | 4.3 | 18.1 | 0.1978, 0.4619 | 499.8 |
|  | Compound 1 (100% by weight) | 17.43 | 1.89 | 3.22 | 51.84 | 0.25, 0.5619 | 506.5 |
| Example 12 | Compound 4 (20% by weight) | 11.5 | 2.76 | 3.8 | 29.93 | 0.2605, 0.5791 | 511.8 |
|  |  | 10 mA/cm$^2$ | | | | | |
| Example 11 | Compound 1 (10% by weight) | 10.49 | 10 | 5.58 | 14.31 | 0.1839, 0.4196 | 492.3 |
|  | Compound 1 (20% by weight) | 9.63 | 10 | 4.93 | 15.91 | 0.1968, 0.4608 | 495.3 |
|  | Compound 1 (100% by weight) | 14.48 | 10 | 4.01 | 34.39 | 0.2475, 0.5591 | 508 |
| Example 12 | Compound 4 (20% by weight) | 10.78 | 10 | 4.81 | 22.13 | 0.2589, 0.578 | 508.8 |

-continued
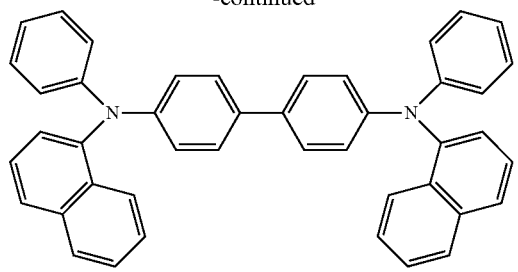
α-NPD
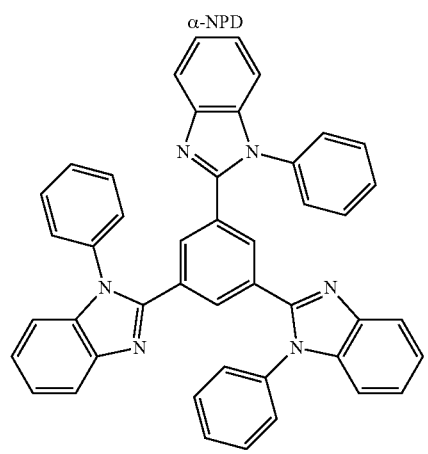
TPBi
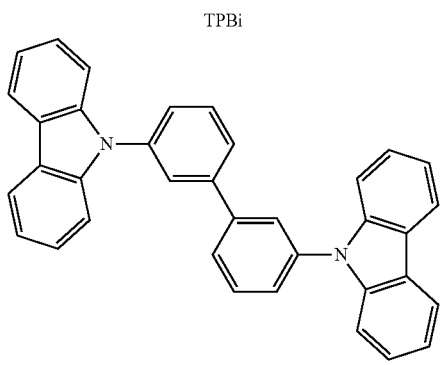
mCBP
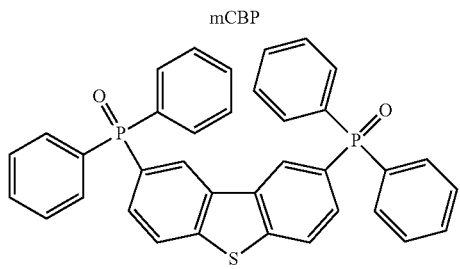
PPT
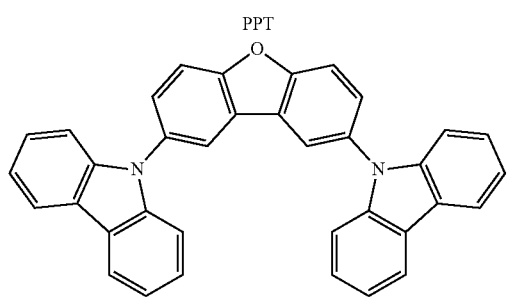
Cz2DBF
-continued
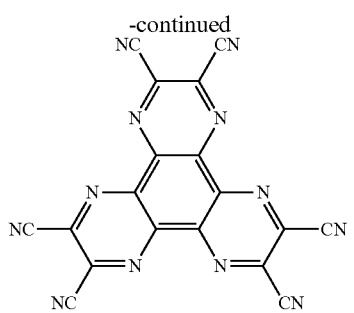
HAT-CN
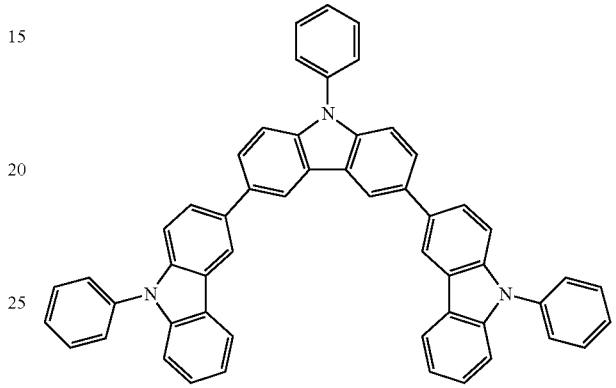
Tris-PCz
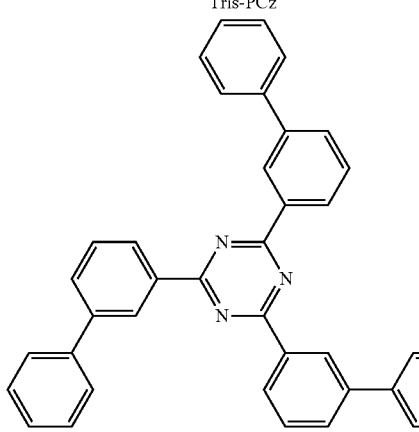
T2T
BPy-TP2
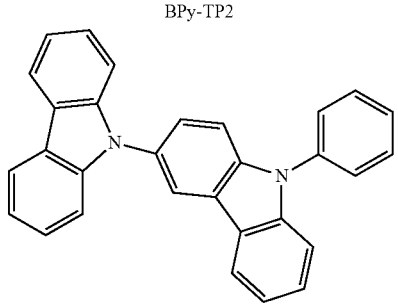
CCP -continued

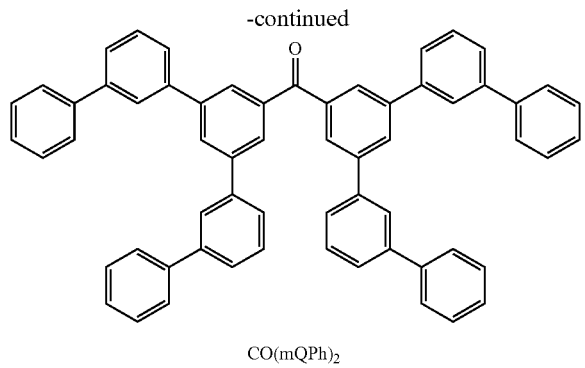

CO(mQPh)₂

INDUSTRIAL APPLICABILITY

The compound of the invention is useful as a light emitting material. Accordingly, the compound of the invention may be effectively used as a light sitting material of an organic light emitting device, such as an organic electroluminescent device. The compound. of the invention includes a compound that emits delayed fluorescent light, and thus may be capable of providing an organic light emitting device having a high light emission efficiency. Thus, the invention has high industrial applicability.

REFERENCE SIGNS LIST 1 substrate
2 anode
3 hole injection layer
4 hole transporting layer
5 light emitting layer
6 electron transporting layer
7 cathode

The invention claimed is:
1. A compound represented by the following formula (1'):

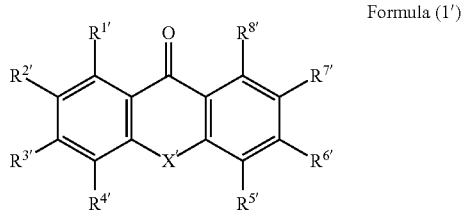

Formula (1')

wherein in the formula (1'), X' represents an oxygen atom or a sulfur atom; and $R^{1'}$ to $R^{8'}$ each independently represent a hydrogen atom, a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, a nitro group, or a group represented by any one of the following formulae (2') to (6'), provided that at least one of $R^{1'}$ to $R^{8'}$ each independently represent a group represented by any one of the following formulae (2') to (6'), and such a case is excluded that $R^{2'}$ and $R^{7'}$ each represent a group represented by the following formula (2'), and all $R^{21'}$ to $R^{28'}$ represent hydrogen atoms,

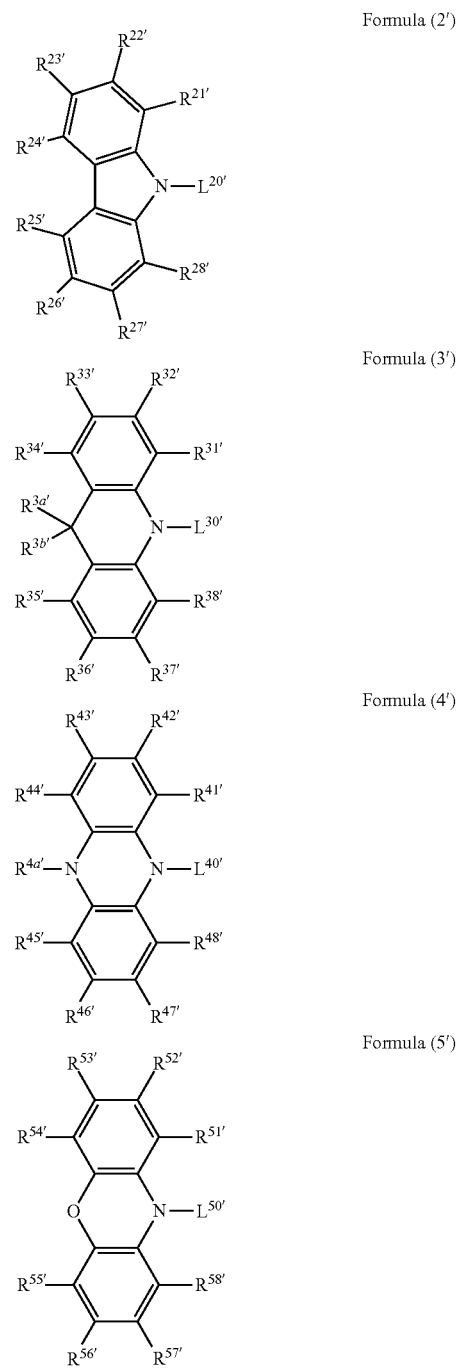

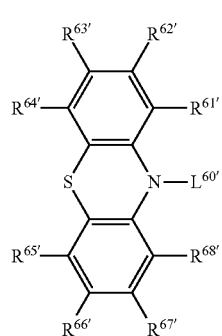

Formula (6')

wherein in the formulae (2') to (6'), $L^{20'}$, $L^{30'}$, $L^{40'}$, $L^{50'}$ and $L^{60'}$ each independently represent a single bond or a divalent linking group selected from an alkenylene group, an alkynylene group, an arvlene group, a thiophenediyl group, and a linking group formed of a combination of these groups, and the group represented by any one of the formulae (2') to (6') is bonded to the cyclic structure of the formula (1') through $L^{20'}$, $L^{30'}$, $L^{40'}$, $L^{50'}$ or $L^{60'}$; and $R^{21'}$ to $R^{28'}$, $R^{31'}$ to $R^{38'}$, $R^{3a'}$, $R^{3b'}$, $R^{41'}$ to $R^{48'}$, $R^{4a'}$, $R^{51'}$ to $R^{58'}$, and $R^{61'}$ to $R^{68'}$ each independently represent a hydrogen atom, a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, a nitro group, or a group represented by any one of the formulae (2') to (6'), provided that $R^{3a'}$ and $R^{3b'}$ may be bonded to each other to form a cyclic structure selected from a fluorene ring, a xanthene ring and a thioxanthene ring.

* * * * *